US011723919B2

(12) United States Patent
Zanzalari et al.

(10) Patent No.: US 11,723,919 B2
(45) Date of Patent: Aug. 15, 2023

(54) COMPOSITION OR COMBINATION COMPRISING ANIONIC DIETARY SUPPLEMENT AND 25-HYDROXY VITAMIN D

(71) Applicants: Kenneth P. Zanzalari, Teaneck, NJ (US); James D. Chapman, Teaneck, NJ (US); Glenn A. Holub, Teaneck, NJ (US); Scott S. Bascom, Teaneck, NJ (US); Timothy E. Costigan, Teaneck, NJ (US); Dean Warras, Teaneck, NJ (US)

(72) Inventors: Kenneth P. Zanzalari, Teaneck, NJ (US); James D. Chapman, Teaneck, NJ (US); Glenn A. Holub, Teaneck, NJ (US); Scott S. Bascom, Teaneck, NJ (US); Timothy E. Costigan, Teaneck, NJ (US); Dean Warras, Teaneck, NJ (US)

(73) Assignee: Phibro Animal Health Corporation, Teaneck, NJ (US)

( * ) Notice: Subject to any disclaimer, the term of this patent is extended or adjusted under 35 U.S.C. 154(b) by 40 days.

(21) Appl. No.: 17/345,255

(22) Filed: Jun. 11, 2021

(65) Prior Publication Data

US 2021/0386778 A1 Dec. 16, 2021

Related U.S. Application Data

(60) Provisional application No. 63/150,159, filed on Feb. 17, 2021, provisional application No. 63/038,500, filed on Jun. 12, 2020.

(51) Int. Cl.
*A61K 33/14* (2006.01)
*A23K 10/33* (2016.01)
(Continued)

(52) U.S. Cl.
CPC .............. *A61K 33/14* (2013.01); *A23K 10/33* (2016.05); *A23K 10/38* (2016.05); *A23K 20/174* (2016.05);
(Continued)

(58) Field of Classification Search
CPC .. A61K 31/105; A61K 31/198; A61K 31/593; A61K 31/7048; A61K 33/02;
(Continued)

(56) References Cited

U.S. PATENT DOCUMENTS 5,556,634 A 9/1996 Moore
6,120,815 A 9/2000 Moore
(Continued)

FOREIGN PATENT DOCUMENTS

EP 0 943 246 9/1999

OTHER PUBLICATIONS

"Animate—Anionic Mineral Supplement" Product Information Sheet, 2018, downloaded from https://www.phibropro.com/wp-content/uploads/2018/02/Phibro_PromoSheet.pdf on Sep. 16, 2021.
(Continued)

*Primary Examiner* — Trevor Love
(74) *Attorney, Agent, or Firm* — Klarquist Sparkman, LLP

(57) ABSTRACT

Embodiments of a composition and/or combination comprising an anionic dietary supplement and 25-hydroxy vitamin D are disclosed. The anionic dietary supplement may be a negative dietary cation anion difference (DCAD) supplement and/or may comprise magnesium chloride, magnesium sulfate, ammonium chloride, ammonium sulfate, and calcium sulfate, and/or complexes thereof. Also disclosed are embodiments of a method for administrating the combination and/or composition to an animal, such as a ruminant. In certain embodiments, the animal is a dairy cow, and the
(Continued)

method may be a method for increasing milk yield, and/or improving the health of the animal.

25 Claims, 7 Drawing Sheets

(51) Int. Cl.

| | |
|---|---|
| A23K 10/38 | (2016.01) |
| A23K 20/174 | (2016.01) |
| A23K 20/24 | (2016.01) |
| A23K 20/26 | (2016.01) |
| A23K 20/28 | (2016.01) |
| A23K 50/10 | (2016.01) |
| A61K 31/105 | (2006.01) |
| A61K 31/198 | (2006.01) |
| A61K 31/593 | (2006.01) |
| A61K 31/7048 | (2006.01) |
| A61K 33/02 | (2006.01) |
| A61K 33/06 | (2006.01) |
| A61K 33/08 | (2006.01) |
| A61K 33/34 | (2006.01) |
| A61K 36/06 | (2006.01) |
| A61K 36/185 | (2006.01) |
| A61K 36/896 | (2006.01) |
| A61K 38/47 | (2006.01) |
| A61K 38/51 | (2006.01) |
| A61K 45/06 | (2006.01) |
| A61K 47/02 | (2006.01) |
| A61K 47/46 | (2006.01) |
| A61P 3/02 | (2006.01) |
| A61P 3/14 | (2006.01) |
| A23K 20/111 | (2016.01) |
| A23K 20/163 | (2016.01) |
| A23K 40/25 | (2016.01) |
| A23K 50/42 | (2016.01) |

(52) U.S. Cl.
CPC ............ *A23K 20/24* (2016.05); *A23K 20/26* (2016.05); *A23K 20/28* (2016.05); *A23K 50/10* (2016.05); *A61K 31/105* (2013.01); *A61K 31/198* (2013.01); *A61K 31/593* (2013.01); *A61K 31/7048* (2013.01); *A61K 33/02* (2013.01); *A61K 33/06* (2013.01); *A61K 33/08* (2013.01); *A61K 33/34* (2013.01); *A61K 36/06* (2013.01); *A61K 36/185* (2013.01); *A61K 36/896* (2013.01); *A61K 38/47* (2013.01); *A61K 38/51* (2013.01); *A61K 45/06* (2013.01); *A61K 47/02* (2013.01); *A61K 47/46* (2013.01); *A61P 3/02* (2018.01); *A61P 3/14* (2018.01)

(58) Field of Classification Search
CPC ........ A61K 33/06; A61K 33/08; A61K 33/14; A61K 33/34; A61K 36/06; A61K 36/185; A61K 36/896; A61K 38/47; A61K 38/51; A61K 45/06; A61K 47/02; A61K 47/46; A23K 10/30; A23K 10/33; A23K 10/38; A23K 20/111; A23K 20/163; A23K 20/174; A23K 20/24; A23K 20/26; A23K 20/28; A23K 40/25; A23K 50/10; A23K 50/42; A61P 3/02; A61P 3/14
See application file for complete search history.

(56) References Cited

U.S. PATENT DOCUMENTS

| | | |
|---|---|---|
| 10,197,581 B2* | 2/2019 | Zielinski .............. G01N 33/82 |
| 2002/0176883 A1 | 11/2002 | Block et al. |
| 2017/0000805 A1 | 1/2017 | Elliott et al. |

OTHER PUBLICATIONS

Cho et al., "Effects of 25-hydroxyvitamin D3 and manipulated dietary cation-anion difference on the tenderness of beef from cull native Korean cows," *Journal of Animal Science* 84(6):1481-1488, Jun. 2006.

DeGaris et al., "Milk fever in dairy cows: A review of pathophysiology and control principles," *Veterinary Journal* 176(1):58-69, 2009.

Guo et al., "Effect of dietary vitamin $D_3$ and 25-hydroxyvitamin $D_3$ supplementation on plasma and milk 25-hydroxyvitamin D3 concentration in dairy cows," *Journal of Diary Science* 101(4):3545-3553, Apr. 2018.

International Search Report and Written Opinion dated Sep. 10, 2021 from International Application No. PCT/US2021/036990 (15 pages).

Martinez et al., "Effects of prepartum dietary cation-anion difference and source of vitamin D in dairy cows: Health and reproductive responses," *Journal of Dairy Science* 101(3):2563-2578, 2018.

Martinez et al., "Effects of prepartum dietary cation-anion difference and source of vitamin D in dairy cows: Lactation performance and energy metabolism," *Journal of Dairy Science* 101(3):2544-2562, Mar. 2018.

McGrath et al., "Anionic salt supplementation and intra-rumen administration of 25 hydroxycholcalciferol increase urinary calcium excretion," *Recent Advances in Animal Nutrition—Australia*, pp. 139-140, Jul. 2011.

McGrath et al., "Anionic salts and dietary 25-hydroxyvitamin D stimulate calcium availability in steers," *Animal* 7(3):404-409, Mar. 2013.

Rodney et al., "Associations between bone and energy metabolism in cows fed diets differing in level of dietary cation-anion difference and supplemented with cholecalciferol or calcidiol," *Journal of Dairy Science* 101(7):6581-6601, Jul. 2018.

Rodney et al., "Effects of prepartum dietary cation-anion difference and source of vitamin D in dairy cows: Vitamin D, mineral, and bone metabolism," *Journal of Dairy Science* 101(3):2519-2543, Mar. 2018.

Weiss et al., "Effect of feeding 25-hydroxyvitamin $D_3$ with negative cation-anion difference diet on calcium and vitamin D status of periparturient cows and their calves," *Journal of Dairy Science* 98(8):5588-5600, Aug. 2015.

\* cited by examiner

| Measured Parameters | Ionized Ca | Plasma Ca, P, Mg | Plasma 25-OH | Plasma NEFA, BHBA, Glu | Serum Creatinine | Urine Creatinine, Ca, Mg |
|---|---|---|---|---|---|---|
| Coagulant | | Heparin | Heparin | | | |
| Task or Sample | | | | | | |
| Dry Period Collection Times | | | | | | |
| Day -28 DRP Entry CU pen | x | x | x | x | x | x |
| Day -21 DRP | | | | | | |
| Day -14 DRP | | | | | | |
| Day -7 DRP | x | x | | | x | x |
| Day -3 DRP | x | x | x | x | x | x |
| Calving (d 0) | x | x | x | x | | |
| Lactation Period Collection Times | | | | | | |
| Day +1 DRP | x | x | | | x | x |
| Day +2 DRP | x | x | | | x | x |
| Day +3 DRP | x | x | | | x | x |
| Day +4 DRP | x | x | x* | x | x | x |
| Day +7 DRP | | | | x | | |
| Day +14 DRP | | | | x | | |
| Day +21 DRP | | | | | | |
| Day +28 DRP | x | x | x | x | x | x |

FIG. 2

| Measured Parameters | For Bone Markers | | | 
|---|---|---|---|
| | Serum Creatinine, Serotonin, CTX-1 | Plasma PTH, uOc, cOC | For Urine DPD |
| | Dry Period Collection Times | | |
| Day -28 DRP Entry CU pen | X* | X* | X* |
| Day -21 DRP | | | |
| Day -14 DRP | | | |
| Day -7 DRP | | | |
| Day -3 DRP | X* | X* | X* |
| Calving (d 0) | X* | X* | X* |
| | Lactation Period Collection Times | | |
| Day +1 DRP | | | |
| Day +2 DRP | | | |
| Day +3 DRP | X* | X* | X* |
| Day +4 DRP | | | |
| Day +7 DRP | X* | X* | X* |
| Day +14 DRP | | | |
| Day +21 DRP | | | |
| Day +28 DRP | X* | X* | X* |

FIG. 3

| Day | Control | HyD 1 mg | HyD 2 mg | P value |
|---|---|---|---|---|
| -9 | 1.28 | 1.32 | 1.35 | 0.195 |
| -5 | 1.29b | 1.34a | 1.34a | 0.037 |
| -3 | 1.30 | 1.27 | 1.32 | 0.213 |
| +1 | 1.13ab | 1.10b | 1.20a | 0.038 |
| +2 | 1.12 | 1.10 | 1.18 | 0.108 |

FIG. 5

| Day | Control | HyD 1 mg | HyD 2 mg | P value |
|---|---|---|---|---|
| -3 | 10.09 | 10.19 | 10.33 | 0.127 |
| +1 | 8.87e | 9.26de | 9.57d | 0.074 |
| +2 | 9.08 | 9.16 | 9.49 | 0.372 |
| +3 | 9.34 | 9.42 | 9.56 | 0.691 |
| +4 | 9.60 | 9.54 | 9.72 | 0.724 |

FIG. 7

COMPOSITION OR COMBINATION COMPRISING ANIONIC DIETARY SUPPLEMENT AND 25-HYDROXY VITAMIN D

CROSS REFERENCE TO RELATED APPLICATION

This application claims the benefit of the earlier filing dates of U.S. provisional patent application No. 63/038,500, filed Jun. 12, 2020, and U.S. provisional application No. 63/150,159, filed on Feb. 17, 2021, both of which are incorporated herein by reference in their entireties.

FIELD

The present disclosure concerns a combination and/or composition comprising an anionic dietary supplement and 25 hydroxy vitamin D species for administration to an animal.

BACKGROUND

The transition period from the dry period to lactation is an important time for dairy cows. Management of cows during the transition period can have a substantial effect on how well the dairy cows perform during the subsequent lactation period, particularly with respect to milk yield.

SUMMARY

Disclosed herein is a combination and/or composition comprising an anionic dietary supplement and a vitamin D species, such as a 25-hydroxy vitamin D species. In some embodiments, the combination and/or composition comprises magnesium chloride, magnesium sulfate, ammonium chloride, ammonium sulfate, and calcium sulfate, and/or complexes thereof, and a 25-hydroxy vitamin D species. The 25-hydroxy vitamin D species may be 25-hydroxy vitamin $D_3$.

The combination and/or composition may further comprise magnesium oxide, phosphoric acid, molasses or silica (for example, diatomaceous earth), dried distillers grains and solubles (DDGS), corn gluten feed, mineral clay (for example, bentonite), water, or a combination thereof. In some embodiments, the combination and/or composition comprises one or more of magnesium oxide, phosphoric acid, molasses or silica, and/or may comprise one or more of dried distillers grains and solubles (DDGS), corn gluten feed, mineral clay, or water.

In any embodiments, the combination and/or composition may comprise from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, and/or complexes thereof. The combination and/or composition may further comprise from greater than zero to 1% w/w phosphoric acid, and/or from greater than zero to 5% w/w molasses, from greater than zero to 1% w/w silica, from greater than zero to 10% water, or a combination thereof. Additionally or alternatively, the combination and/or composition may comprise from 20% to 60% or more of w/w dried distillers grains and solubles (DDGS), corn gluten feed, mineral clay, or a combination thereof.

In an exemplary embodiment, the combination and/or composition comprises magnesium chloride, magnesium sulfate, ammonium chloride, ammonium sulfate, and calcium sulfate, or complexes thereof, and further comprises phosphoric acid, silica, molasses, DDGS, and water. In some examples, the combination and/or composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 1% w/w silica, from greater than zero to 50% w/w molasses, from 30% to 60% w/w DDGS, and from greater than zero to 10% water.

In another exemplary embodiment, the combination and/or composition comprises magnesium chloride, magnesium sulfate, ammonium chloride, ammonium sulfate, and calcium sulfate, or complexes thereof, and further comprises phosphoric acid, magnesium oxide, mineral clay, and water. In some examples, the combination and/or composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from 1% to 50% w/w magnesium oxide, from 20% to 40% w/w mineral clay, and from greater than zero to 10% water.

In a further exemplary embodiment, the combination and/or composition comprises magnesium chloride, magnesium sulfate, ammonium chloride, ammonium sulfate, and calcium sulfate, or complexes thereof, and further comprises phosphoric acid, molasses, corn gluten feed, and water. In some examples, the combination and/or composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 5% w/w molasses, from 30% to 60% w/w corn gluten feed, and from greater than zero to 10% water.

In any embodiments, the combination and/or composition may comprise a first composition comprising magnesium chloride, magnesium sulfate, ammonium chloride, ammonium sulfate, and calcium sulfate, and/or complexes thereof and optionally one or more of magnesium oxide, phosphoric acid, molasses or silica, dried distillers grains and solubles (DDGS), corn gluten feed, mineral clay, or water, and a second composition comprising the 25 hydroxy vitamin D species. The combination and/or composition may be an admixture of the first and second compositions. In other embodiments, the first and second compositions are formulated together to form single particles, where each particle comprises both the first and second compositions. In such embodiments, the combination and/or composition may comprise particles of the first composition that are at least partially coated with the second composition. The combination and/or composition may comprise a carrier, such as an oil, for example, a mineral oil, that facilitates the second composition at least partially coating particles of the first composition. Alternatively, the second composition may be an emulsion.

In any embodiments, the combination and/or composition may comprise from 20,000 IU to 200,000 IU of the 25-hydroxy vitamin D species, such as from 50,000 IU to 120,000 IU of the 25-hydroxy vitamin D species.

In any embodiments, the combination and/or composition may further comprise a feed, and/or a calcium source. The calcium source may be calcium carbonate, bone ash, bone meal, calcite, limestone, calcium gluconate, calcium hydroxide, calcium sulfate, calcium chloride, calcium butyrate, chalk, clam shells, oyster shells, dolemite, calcium chelates, monocalcium phosphate, dicalcium phosphate, calcium propionate, or any combination thereof. The calcium source may be admixed with the combination and/or composition, and in some embodiments, the admixture comprises at least 1.6% dietary calcium.

Additionally, or alternatively, the combination and/or composition may further comprise one or more of yucca, quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride (DFA) III, or combinations thereof.

In some embodiments, the combination and/or composition further comprises silica, mineral clay, glucan, mannans, and an endoglucanohydrolase. Additionally, or alternatively, the combination and/or composition may further comprise a direct fed microbial, such as *Bacillus coagulans, Bacillus subtilis, Bacillus licheniformis, Bacillus amyloliquefaciens*, or a combination thereof. And/or the combination and/or composition may comprise yucca and/or quillaja, and/or a chromium compound, a metal chelate, a copper species, or a combination thereof.

In any embodiments, the combination and/or composition may comprise from 20,000 IU or less to 200,000 IU or more, such as from 50,000 IU to 120,000 IU of the 25-hydroxy vitamin D species.

In certain embodiments, the combination and/or composition is a composition comprising the anionic dietary supplement and the vitamin D species, but in other embodiments, the combination and/or composition is a combination.

Also disclosed herein are embodiments of a method for administering a combination and/or composition as disclosed herein. The method may comprise administering to an animal, such as a ruminant, a combination and/or composition comprising magnesium chloride, magnesium sulfate, ammonium chloride, ammonium sulfate, and calcium sulfate, and/or complexes thereof, and a 25-hydroxy vitamin D species. The ruminant may be a bovine, sheep, goat, deer, elk, alpaca, camel or llama. In some embodiments, the bovine is a cow, bull, steer, heifer, calf, bison, or buffalo, and may be a dairy cow. The combination and/or composition may further comprise magnesium oxide, phosphoric acid, molasses or silica, dried distillers grains and solubles (DDGS), corn gluten feed, mineral clay, water, or a combination thereof.

In some embodiments, the method comprises administering a combination and/or composition comprising a first composition comprising the magnesium chloride, magnesium sulfate, ammonium chloride, ammonium sulfate, and calcium sulfate, and/or complexes thereof, and a second composition comprising the 25-hydroxy vitamin D species. The first composition may comprise from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, and/or complexes thereof. The first composition may comprise from greater than zero to 1% w/w phosphoric acid, and/or may comprise from greater than zero to 5% w/w molasses, from greater than zero to 1% w/w silica, from greater than zero to 10% water, or a combination thereof. Additionally or alternatively, the first composition may comprise from 20% to 60% or more w/w of dried distillers grains and solubles (DDGS), corn gluten feed, mineral clay, or a combination thereof.

In an exemplary embodiments, the first composition comprises magnesium chloride, magnesium sulfate, ammonium chloride, ammonium sulfate, and calcium sulfate, or complexes thereof, and further comprises phosphoric acid, silica, molasses, DDGS, and water. Some embodiments of the first composition comprise from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 1% w/w silica, from greater than zero to 5% w/w molasses, from 30% to 60% w/w DDGS, and from greater than zero to 10% water. In another exemplary embodiment, the first composition comprises magnesium chloride, magnesium sulfate, ammonium chloride, ammonium sulfate, and calcium sulfate, or complexes thereof, and further comprises phosphoric acid, magnesium oxide, mineral clay, and water. Some embodiments of the first composition comprise from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from 1% to 5% w/w magnesium oxide, from 20% to 40% w/w mineral clay, and from greater than zero to 10% water. And in a further exemplary embodiment, the first composition comprises magnesium chloride, magnesium sulfate, ammonium chloride, ammonium sulfate, and calcium sulfate, or complexes thereof, and further comprises phosphoric acid, molasses, corn gluten feed, and water. Some embodiments of the first composition comprise from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 5% w/w molasses, from 30% to 60% w/w corn gluten feed, and from greater than zero to 10% water.

In any embodiments of the disclosed method, the combination and/or composition may comprise from 20,000 IU or less to 200,000 IU or more, such as from 50,000 IU to 120,000 IU, of the 25-hydroxy vitamin D species, and/or the 25-hydroxy vitamin D species may be 25-hydroxy vitamin $D_3$.

The first composition and the second composition may be administered substantially sequentially, or they may be administered sequentially in any order. Administering sequentially may comprise a first administration comprising administering one of the first and second compositions, and a second administration subsequent to the first administration, the second administration comprising administering the other of the first and second compositions, such that a time period between the first and second administrations is sufficient for the animal to receive an overlapping benefit from the first and second administrations.

In some embodiments of the disclosed method, the combination and/or composition may be admixed with a feed. And/or the combination and/or composition may further comprise yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride III, or combinations thereof. In some embodiments, the method further comprises administering silica, mineral clay, glucan, mannans, and an endoglucanohydrolase; a direct fed microbial, such as *Bacillus coagulans, Bacillus subtilis, Bacillus licheniformis, Bacillus amyloliquefaciens*, or a combination thereof, yucca and/or quillaja; a chromium compound; a metal chelate; a copper species; or a combination thereof.

The combination and/or composition may be administered to a female ruminant, such as a dairy cow, for a time period of from the start of the dry period to up to 150 days post calving. In other embodiments, the combination and/or composition is administered to the dairy cow for a time period of from 65 days prior to calving to up to 150 days or more post calving. In any embodiments, the time period may be from 56 days prior to calving, such as from 28 days or 21 days prior to calving. And/or the time period may be up to 100 days post calving, such as up to 75 days, 48 days, or 28 days post calving.

In any embodiments, the combination and/or composition may be administered in an amount sufficient to provide from 0.5 pounds per day to 2 pounds per day of the first composition, such as from 1.2 pounds per day to 1.5 pounds per day of the first composition. Additionally, or alternatively, the combination and/or composition may be administered in an amount sufficient to provide from 20,000 IU or less to 240,000 IU or more, such as from 50,000 IU to 120,000 IU, of the 25-hydroxy vitamin D species. In some embodiments, the combination and/or composition is administered in an amount sufficient to provide from 0.5 mg per head per day to 5 mg per head per day, such as 1 mg per head per day to 3 mgs per head per day, of the 25-hydroxy vitamin D species.

Also disclosed herein are embodiments of a method of increasing milk yield in a dairy cow, the method comprising administering to the dairy cow a combination and/or composition disclosed herein. In some embodiments, the combination and/or composition is administered during the dairy cow's transition period.

The foregoing and other objects, features, and advantages of the invention will become more apparent from the following detailed description, which proceeds with reference to the accompanying figure.

BRIEF DESCRIPTION OF THE DRAWINGS

FIG. 2 is a table providing the sample collection schedule and illustrating which variables are measured at each time point during the trial described in Example 4.

FIG. 3 is a table illustrating which bone marker variables are measured are different time points during the trial described in Example 4.

FIG. 5 is a table illustrating certain results from the graph in FIG. 4.

FIG. 7 is a table illustrating certain results from the graph in FIG. 6.

DETAILED DESCRIPTION

I. Introduction and Definitions

Figure 1:
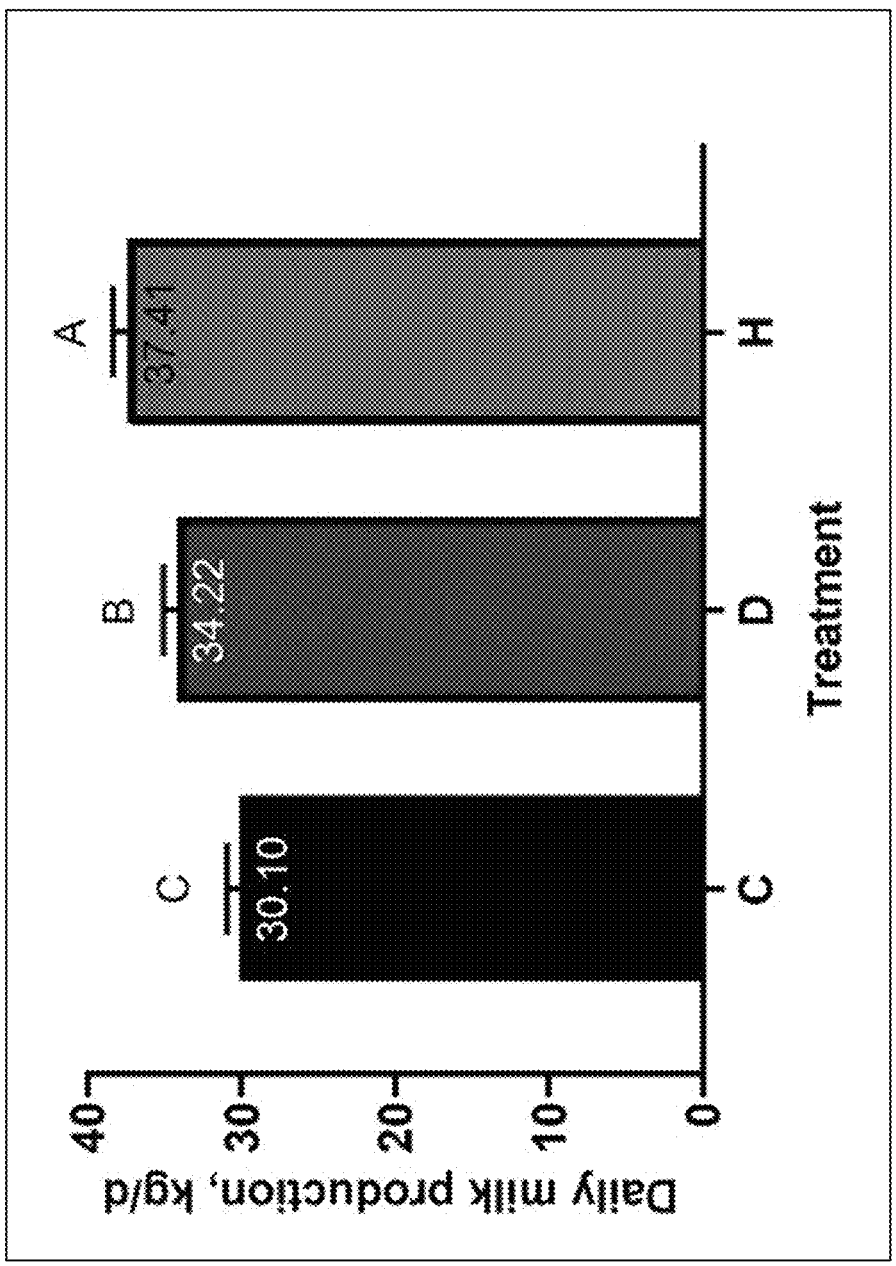
FIG. 1 is a graph of daily milk production versus treatment, illustrating the milk yield of cows in the control group (feed+vitamin D supplement; C), anionic dietary supplement+vitamin D group (D), and anionic dietary supplement+25-hydroxy vitamin D group (H).

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

When chemical structures are depicted or described, unless explicitly stated otherwise, all carbons are assumed to include sufficient hydrogen moieties in addition to any other moieties present, so that each carbon conforms to a valence of four.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and consequently can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that, unless otherwise specified, the disclosed compounds encompass any tautomeric, conformational isomeric, optical isomeric, and/or geometric isomeric forms of the compounds described herein, as well as mixtures of these various different isomeric forms. In cases of limited rotation, e.g. around an amide bond, atropisomers are also possible and are also specifically included in the compounds of the invention.

Administering: Administration by any route to a subject. As used herein, administration typically but not necessarily refers to oral administration.

Co-administration: Administering two or more agents simultaneously or sequentially in any order to a subject to provide overlapping periods of time in which the subject is experiencing effects, beneficial and/or deleterious, from each agent. For example, if administration of a first agent results in deleterious side effects, as second agent may be administered to reduce and/or substantially prevent or inhibit those side effects. One or both of the agents may be a therapeutic agent. The agents may be combined into a single composition or dosage form, or they may be administered simultaneously or sequentially in any order as separate agents.

Combination: A combination includes two or more components that are administered such that the effective time period of at least one component overlaps with the effective time period of at least one other component. A combination, or a component thereof, may be a composition. In some embodiments, effective time periods of all components administered overlap with each other. In an exemplary embodiment of a combination comprising three components, the effective time period of the first component administered may overlap with the effective time periods of the second and third components, but the effective time periods of the second and third components independently may or may not overlap with one another. In another exemplary embodiment of a combination comprising three components, the effective time period of the first component administered overlaps with the effective time period of the second component, but not that of the third component; and the effective time period of the second component overlaps with those of the first and third components. A combination may be a composition comprising the components, a composition comprising one or more components and another separate component (or components) or composition(s) comprising the remaining component(s), or the combination may be two or more individual components. In some embodiments, the two or more components may comprise the same component administered at two or more different times, two or more different components administered substantially simultaneously or sequentially in any order, or a combination thereof.

Excipient or carrier: A physiologically inert substance that is used as an additive in (or with) a combination, composition, or component as disclosed herein. As used herein, an excipient or carrier may be incorporated within particles of a combination, composition, or component, or it may be physically mixed with particles of a combination, composition, or component. An excipient or carrier can be used, for example, to dilute an active agent and/or to modify properties of a combination or composition, such as flowability, stability during storage, exposure to moisture, etc. Examples of excipients and carriers include, but are not limited to, calcium carbonate, polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Effective amount: A quantity or concentration of a specified compound, composition or combination sufficient to achieve an effect.

Feed efficiency: A measure of an animal's efficiency in converting feed mass into the desired output, e.g., weight gain, milk production. Feed efficiency also may be referred to as feed conversion ratio, feed conversion rate, or feed conversion efficiency. The feed efficiency is also known in the art as the feed conversion ratio, or feed conversion rate.

Ruminant: Examples of animals that can be fed and/or administered the disclosed combination include, but are not limited to, ruminant species, such as cattle, bovines, sheep, goat, cow, deer, bison, buffalo, elk, alpaca, camel or llama.

Therapeutic agent: An agent that is capable of providing a therapeutic effect, e.g., preventing a disorder, inhibiting a disorder, such as by arresting the development of the disorder or its clinical symptoms, or relieving a disorder by causing regression of the disorder or ameliorating its clinical symptoms.

Therapeutically effective amount: A quantity or concentration of a specified compound, composition or combination sufficient to achieve an effect in a subject.

Transition: The process of a cow not producing milk (dry cow), calving, and then producing milk. A transition period may be approximately three weeks before calving and three weeks following calving.

Additional information concerning various aspects of the present invention can be found in: PCT application Nos. PCT/US2015/053439, PCT/US2016/051080 and PCT/US2018/014978; U.S. application Ser. Nos. 15/359,342, 14/699,740, 14/606,862, 13/566,433, 13/872,935, and 62/621,196, and U.S. Patent Publication No. 2013/0017211, U.S. Patent Publication No. 2012/0156248, U.S. Patent Publication No. 2007/0253983, U.S. Patent Publication No. 2007/0202092, U.S. Patent Publication No. 2007/0238120, U.S. Patent Publication No. 2006/0239992, U.S. Patent Publication No. 2005/0220846, U.S. Patent Publication No. 2005/0180964, and Australian Patent Application No. 2011/201420. Each of these prior applications is incorporated herein by reference in its entirety.

II. Primary Composition

Disclosed herein is a primary composition and/or combination comprising an anionic dietary supplement, such as a negative dietary cation anion difference (DCAD) supplement, and a vitamin D species. The vitamin D species may be 25-hydroxy vitamin D, such as 25-hydroxy vitamin $D_3$. The anionic dietary supplement may comprise minerals useful for feeding to an animal, such as a ruminant. In some embodiments, the anionic dietary supplement comprises cations of magnesium, calcium and ammonium, and/or anions such as halides, for example, chloride, bromide or iodide, sulfates and/or oxides. In some embodiments, the anionic dietary supplement comprises a sulfate salt and one or more of a halide salt and an oxide salt, and in certain embodiments, the first composition comprises at least a sulfate salt and a halide salt. And in some embodiments, the anionic dietary supplement comprises three or more of magnesium chloride, magnesium oxide, magnesium sulfate, ammonium chloride, ammonium sulfate, or calcium sulfate.

The primary combination and/or composition may comprise a first composition comprising the anionic dietary supplement, and a second composition comprising the vitamin D species. In some embodiments, the primary combination and/or composition is a composition comprising the first and second compositions. The composition may be an intimate mixture of the first and second composition, optionally with a feed. Alternatively, the first and second compositions may be formulated together to form single particles, such as pellets or granules, where each particle comprises both the first and second compositions.

In other embodiments, the primary combination and/or composition is a combination of the first and second compositions. The combination may be in the form of a mixture of the first and second compositions, or the first and second compositions may be separate but administered in combination. For example, the primary combination and/or composition may be administered in combination such that one of the first and second compositions is administered as a first administration at a first time point and the other of the first and second compositions is administered as a second administration at a second time point subsequent to the first time point, such that the animal is still receiving a benefit from the first administration, and therefore receives the benefit of the combination. In some embodiments, the first composition is administered first, but in other embodiments, the second composition is administered first.

A. First Composition

The first composition may comprise salts of magnesium, calcium and ammonium, and may comprise halide salt, such as chloride, bromide or iodide, sulfate salt and/or oxide salt. In some embodiments, the first composition comprises a sulfate salt and one or more of a halide salt and an oxide salt, and in certain embodiments, the first composition comprises at least a sulfate salt and a halide salt.

In some embodiments, the first composition comprises magnesium chloride, magnesium sulfate, ammonium chloride, ammonium sulfate, and calcium sulfate, and/or complexes thereof. For example, the first composition may comprise ammonium chloride, magnesium chloride, a complex of ammonium chloride and magnesium chloride, or a combination thereof. And/or the first composition may comprise ammonium sulfate, magnesium sulfate, a complex of ammonium sulfate and magnesium sulfate, or a combination thereof.

The first composition may further comprise one or more additional components. The additional component(s) may be magnesium oxide, phosphoric acid, molasses or silica (for example, diatomaceous earth), dried distillers grains and solubles (DDGS), corn gluten feed, mineral clay (for example, bentonite), water, or a combination thereof. A person of ordinary skill in the art understands that any water present in the composition may be affirmatively added water, water that is provided by one or more of the other components (such as, solely by way of example, as a hydrate of one or more of the salts), or a combination thereof.

In some embodiments, the first composition may comprise one or more of magnesium oxide, phosphoric acid, molasses or silica (for example, diatomaceous earth). Additionally, or alternatively, the first composition may comprise dried distillers grains and solubles (DDGS), corn gluten feed, mineral clay (for example, bentonite), water, or a combination thereof.

In some embodiments, the first composition comprises from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, or complexes thereof.

In some embodiments, the first composition further comprises from greater than zero to 1% w/w phosphoric acid. And/or the first composition may comprise from greater than zero to 5% w/w molasses, from greater than zero to 1% w/w silica, and/or from greater than zero to 10% water.

Additionally, or alternatively, the first composition may comprise from 20% to 60% or more w/w dried distillers grains and solubles (DDGS), corn gluten feed, mineral clay (for example, bentonite), or a combination thereof.

In an exemplary embodiment, the first composition comprises, consists essentially of, or consists of, magnesium chloride, magnesium sulfate, ammonium chloride, ammonium sulfate, and calcium sulfate, or complexes thereof, and phosphoric acid, silica, molasses, DDGS, and water, and may comprise, consist essentially of, or consist of, from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and from greater than zero to 1% w/w phosphoric acid, from greater than zero to 1% w/w silica, from greater than zero to 5% w/w molasses, from 30% to 60% w/w DDGS, and from greater than zero to 10% water.

In another exemplary embodiment, the first composition comprises, consists essentially of, or consists of, magnesium chloride, magnesium sulfate, ammonium chloride, ammonium sulfate, and calcium sulfate, or complexes thereof, and phosphoric acid, magnesium oxide, mineral clay, and water, and may comprise, consist essentially of, or consist of, from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and from greater than zero to 1% w/w phosphoric acid, from 1% to 5% w/w magnesium oxide, from 20% to 40% w/w mineral clay, and from greater than zero to 10% water.

In a further exemplary embodiment, the first composition comprises, consists essentially of, or consists of, magnesium chloride, magnesium sulfate, ammonium chloride, ammonium sulfate, and calcium sulfate, or complexes thereof, and phosphoric acid, molasses, corn gluten feed, and water, may comprise, consist essentially of, or consist of, from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and from greater than zero to 1% w/w phosphoric acid, from greater than zero to 5% w/w molasses, from 30% to 60% w/w corn gluten feed, and from greater than zero to 10% water.

One commercial source of an embodiment of the first composition, is Animate®, which is provided by Phibro Animal Health Corporation.

B. Second Composition

The second composition comprises a vitamin D species, such as 25-hydroxy vitamin D, particularly 25-hydroxy vitamin $D_3$. One commercial source of 25-hydroxy vitamin $D_3$ is Hy-Do, which is available from DSM Animal Nutrition & Health. The chemical structure of 25-hydroxy vitamin $D_3$ is provided below.

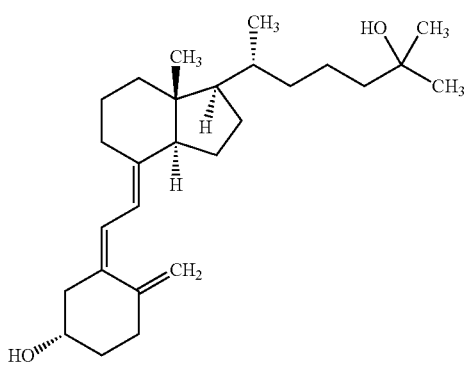

25-hydroxy vitamin D₃ may be formulated with other materials, as disclosed by U.S. Pat. No. 10,517,316, which is incorporated herein by reference. For example, certain compositions comprise a) 25-hydroxy vitamin D, b) a carotenoid selected from the group consisting of: lycopene, astaxanthin, cryptoxanthin, beta-carotene, lutein, zeaxanthin and canthaxanthin, c) vitamin E, d) ascorbic acid, and e) optionally may further comprise at least one further bio-active ingredient selected from the group consisting of: Vitamin D, Vitamin B2, Biotin, Vitamin B6, Niacin, Zinc, Copper, Manganese, and Selenium. Preferably at least Vitamin D is a further bio-active ingredient. Sometimes a further bio-active ingredient includes at least Vitamin D and Selenium. In some cases, all such additional ingredients are included.

A further aspect is the combination of 25-hydroxy vitamin D, with one or more carotenoids, vitamin E and ascorbic acid, and may optionally further comprise at least one further bio-active ingredient selected from the group consisting of Vitamin D, Vitamin B2, Vitamin B6, Niacin, Pantothenic Acid, Folic Acid, Biotin, Zinc, Copper, Manganese, Selenium, and combinations thereof, for the addition to a bovine diet to enhance ovarian health. Preferably the 25-hydroxy vitamin D is 25-hydroxy vitamin D₃. Sometimes, the further bio-active ingredient includes biotin. Sometimes the further bio-active ingredient includes Vitamin D and biotin. Sometimes the further bio-active ingredient includes all the aforementioned optionally bio-active ingredients.

Premixes for bovine feed may comprise a combination of 25-hydroxy vitamin D, vitamin E, ascorbic acid and one or more of the aforementioned carotenoids. Preferably, the 25-hydroxy vitamin D is 25-hydroxy vitamin D₃. In some embodiments the premix also comprises at least one further bio-active ingredient selected from the group consisting of: Vitamin D, Vitamin B2, Vitamin B6, Niacin, Zinc, Copper, Manganese, Selenium and combinations thereof. Sometimes the further bio-active ingredients include at least Vitamin D and Selenium. In some cases, all the further bio-active ingredients are added.

C. Administration

The primary combination and/or composition, or a combination and/or composition comprising the primary combination and/or composition, may be administered in a sufficient amount and at suitable time intervals to provide the first composition and the second composition in amounts and at time intervals believed or determined to be effective for achieving a beneficial result. In some embodiments, the primary combination and/or composition is administered in a sufficient amount to provide the first composition in an amount of from 0.5 pound or less per head per day to 2 pounds or more per head per day, such as from 0.75 pounds to 2 pounds, from 0.85 pounds to 2 pounds, or from 1.2 pounds per head per day to 1.5 pounds per head per day. In some embodiments, the primary combination and/or composition is administered in an amount sufficient to provide from 0.9 to 1 pound per head per day, such as about 0.93 pounds, of the first composition.

In other embodiments, the primary combination and/or composition is administered in an amount sufficient to provide the second composition in an amount of from 0.5 mgs per head per day or less to 6 mgs/head/day or more, such as from 0.5 mgs/head/day to 5 mgs/head/day, from 1 mg/head/day to 5 mgs/head/day, from 1 mg/head/day to 4 mgs/head/day, from 1 mgs/head/day to 3 mgs/head/day, from 1.5 mgs/head/day to 2.5 mgs/head/day, from 1.75 mgs/head/day to 2.25 mgs/head/day, from 0.5 mgs/head/day to 3 mgs/head/day, from 0.5 mgs/head/day to 2.5 mgs/head/day or from 0.5 mgs/head/day to 2 mgs/head/day. In some embodiments, the primary combination and/or composition is administered in an amount sufficient to provide the second composition in an amount of about 2 mg/head/day.

In some embodiments, the primary combination and/or composition is administered in an amount sufficient to provide the second composition in an amount sufficient to provide from 20,000 IU or less to 240,000 IU or more, such as from 20,000 IU to 200,000 IU, or from 50,000 IU to 120,000 IU, of 25-hydroxy vitamin D. And in any embodiments, the 25-hydroxy vitamin D may be 25-hydroxy vitamin D3.

In some embodiments, the primary combination and/or composition is administered in an amount sufficient to provide the second composition in an amount of from 20,000 IU per head per day or less to 240,000 IU/head/day or more, such as from 20,000 IU/head/day to 200,000 IU/head/day, from 40,000 IU/head/day to 200,000 IU/head/day, from 40,000 IU/head/day to 160,000 IU/head/day, from 40,000 IU/head/day to 120,000 IU/head/day, from 60,000 IU/head/day to 100,000 IU/head/day, from 70,000 IU/head/day to 90,000 IU/head/day, from 20,000 IU/head/day to 120,000 IU/head/day, from 20,000 IU/head/day to 100,000 IU/head/day or from 20,000 IU/head/day to 80,000 IU/head/day. In some embodiments, the primary combination and/or composition is administered in an amount sufficient to provide the second composition in an amount of about 80,000 IU/head/day.

In certain embodiments, the same amount of the primary combination and/or composition is administered prepartum and postpartum, but in other embodiments, different amounts of the primary combination and/or composition are administered pre- and postpartum. In some embodiments, the primary combination and/or composition is administered to a prepartum animal in an amount sufficient to provide the second composition in an amount of from 0.5 mgs per head per day or less to 6 mgs/head/day or more, such as from 0.5 mgs/head/day to 5 mgs/head/day, from 1 mg/head/day to 5 mg/head/day, from 1 mg/head/day to 4 mg/head/day, from 1 mg/head/day to 3 mg/head/day, from 1.5 mg/head/day to 2.5 mg/head/day, from 1.75 mg/head/day to 2.25 mg/head/day, or about 2 mgs/head/day. And in some embodiments, the primary combination and/or composition is administered to a postpartum animal in an amount sufficient to provide the second composition in an amount of from 0.5 mgs per head per day or less to 6 mgs/head/day or more, such as from 0.5 mgs/head/day to 5 mgs/head/day, 0.5 mgs/head/day to 3 mgs/head/day, from 0.5 mgs/head/day to 2.5 mgs/head/day or from 0.5 mgs/head/day to 2 mgs/head/day.

And in some embodiments, the primary combination and/or composition is administered to a prepartum animal in an amount sufficient to provide the second composition in an amount of from 20,000 IU per head per day or less to 240,000 IU/head/day or more, such as from 20,000 IU/head/day to 200,000 IU/head/day, from 40,000 IU/head/day to 200,000 IU/head/day, from 40,000 IU/head/day to 160,000 IU/head/day, from 40,000 IU/head/day to 120,000 IU/head/day, from 60,000 IU/head/day to 100,000 IU/head/day, from 70,000 IU/head/day to 90,000 IU/head/day, or about 80,000 IU/head/day. And in some embodiments, the primary combination and/or composition is administered to a postpartum animal in an amount sufficient to provide the second composition in an amount of from 0.5 mgs per head per day or less to 6 mgs/head/day or more, such as from 20,000 IU/head/day to 120,000 IU/head/day, from 20,000 IU/head/day to 100,000 IU/head/day or from 20,000 IU/head/day to 80,000 IU/head/day.

In some embodiments, the primary combination and/or composition is administered in an amount sufficient to raise the blood level of 25-hydroxy vitamin D in the animal to which the primary combination and/or composition is administered to above a blood level of 25-hydroxy vitamin D in an animal that is not administered the primary combination and/or composition. The 25-hydroxy vitamin D blood level in the animal that is administered the primary combination and/or composition may be from greater than zero to 5% or more higher than the 25-hydroxy vitamin D blood level in the animal that is not administered the primary combination and/or composition, such as from greater than zero to 10% or more higher, from greater than zero to 20% or more higher, from greater than zero to 25% or more higher, from greater than zero to 50% or more higher, from greater than zero to 75% or more higher, from greater than zero to 100% or more higher, from greater than zero to 150% or more higher, from greater than zero to 200% or more higher, from greater than zero to 300% or more higher, from greater than zero to 400% or more higher, or from greater than zero to 500% or more higher than an animal that is not administered the primary combination and/or composition.

In certain embodiments, the primary combination and/or composition is administered in an amount sufficient to provide a blood level of 25-hydroxy vitamin D of up to 200 ng/mL or more. In some embodiments, the blood level of 25-hydroxy vitamin D is from greater than zero to 200 ng/mL, such as from 25 ng/mL to 200 ng/mL, from 50 ng/mL to 200 ng/mL, from 60 ng/mL to 200 ng/mL, from 70 ng/mL to 200 ng/mL, from 80 ng/mL to 200 ng/mL, from 90 ng/mL to 200 ng/mL, from 100 ng/mL to 200 ng/mL, from 150 ng/mL to 200 ng/mL or from 175 ng/mL to 200 ng/mL. In certain embodiments, the primary composition is administered in an amount sufficient to provide a blood level of 25-hydroxy vitamin D of about 200 ng/mL. And in particular embodiments, the primary composition is administered in an amount sufficient to provide a blood level of 25-hydroxy vitamin D that does not exceed about 200 ng/mL.

In some embodiments, the primary combination and/or composition is a single composition comprising both the first composition and second composition. In such embodiments, the first and second compositions are administered simultaneously. Such a composition optionally may further comprise one or more additional components, such as the additional components disclosed herein. And/or the composition may be administered in combination with one or more additional components, substantially simultaneously or sequentially in any order.

In other embodiments, the primary combination and/or composition is a combination comprising the first composition and the second composition. In such embodiments, the first composition and the second composition may be administered substantially simultaneously or they may be administered sequentially in any order. Such a combination optionally may further comprise one or more additional components, such as the additional components disclosed herein. And/or the combination may be administered in combination with one or more additional components. The additional component(s) may be administered substantially simultaneously or sequentially in any order with either the first composition, the second composition, or both.

In some embodiments, the primary combination and/or composition is administered to cows, such as dairy cows. In some embodiments, the primary combination and/or composition is administered from 65 days prior to calving or earlier, such as from 60 days, 56 days, 45 days, 30 days, 28 days, or 21 days prior to calving. The primary combination and/or composition may be administered from the start of the dry period. And administration may continue until calving, or until 150 days or more post calving, such as 100 days, 75 days, 50 days, 42 days, 35 days, 28 days, 21 days, 14 days, or 7 days post calving.

IV. Additional Agents

In addition to the first composition and second composition, the primary combination and/or composition may further comprise additional agents either formulated with the primary composition or administered in combination simultaneously, prior to or after the primary composition. Such secondary compositions may comprise, for example, yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor (such as IgF), a vaccine, difructose anhydride (DFA) III, and any and all combinations thereof.

1. Silica, Mineral Clay, Glucan, Mannans, and/or Endoglucanohydrolase

In some embodiments, the primary combination and/or composition further comprises one or more of silica, mineral clay, glucan, mannans, or endoglucanohydrolase. In some embodiments, the primary combination and/or composition and the silica, mineral clay, glucan, mannans and/or endoglucanohydrolase together form a composition, optionally with a feed. In certain embodiments, the primary combination and/or composition and the silica, mineral clay, glucan, mannans and/or endoglucanohydrolase are used in combination, and may be administered sequentially in any order, or substantially simultaneously.

Suitable sources of silica include, but are not limited to, sand, diatomaceous earth, and synthetic silica. Diatomaceous earth is available as a commercially-available product with from 70% to 95% silica ($SiO_2$) and with its remaining components not assayed but primarily ash (minerals) as defined by the Association of Analytical Chemists (AOAC, 2002). In one embodiment, quartz may be used.

The mineral clay (e.g., aluminosilicates) used in this feed supplement may be any of a variety of commercially-available clays including, but not limited to, montmorillonite clay, bentonite and zeolite.

Glucan (e.g., β-glucan, such as β-1,3 (4)glucan), mannans, and/or endoglucanohydrolase can be obtained from plant cell walls, yeast or yeast cell wall or an extract thereof (e.g., *Saccharomyces cerevisiae, Candida utilis*), certain fungi (e.g., mushrooms), algae, and bacteria. β-1,3 (4)-endoglucanohydrolase may be produced from submerged fermentation of a strain of *Trichoderma longibrachiatum*. The endoglucanohydrolase may be an affirmatively added ingredient, or alternatively, or additionally, the endoglucanohydrolase may be present endogenously. As used herein, weight % for endoglucanohydrolase is based on a 70,000 unit/gram endoglucanohydrolase product. The endoglucanohydrolase may be β-1,3 (4)-endoglucanohydrolase. In certain embodiments, the mannans comprise glucomannan. Yeast may be administered affirmatively to provide glucan, mannans and endoglucanohydrolase endogenously. Additionally, or alternatively, in any embodiments disclosed herein, the glucan and mannans may be provided, at least in part, by yeast cell wall or an extract thereof.

In one embodiment, a combination and/or composition comprising silica, mineral clay, glucan and mannans may comprises 1-40 wt % silica, 0.5-25 wt % glucan and mannans, and 40-92 wt % mineral clay, in amounts relative to each other. In another embodiment, such a combination and/or composition comprises 5-40 wt % silica, 0.5-15 wt % glucan and mannans, and 40-80 wt % mineral clay, in amounts relative to each other. In another embodiment, the combination and/or composition comprises 20-40 wt % silica, 0.5-10 wt % glucan and mannans, and 50-70 wt % mineral clay, in amounts relative to each other. In another embodiment, the combination and/or composition comprises 15-40 wt % silica, greater than zero to 15 wt % glucans, greater than zero to 10 wt % mannans, and 50-81 wt % mineral clay, in amounts relative to each other. In another embodiment, the combination and/or composition comprises 15-40 wt % silica, 0.5-5.0 wt % glucans, 0.5-8.0 wt % mannans, and 50-81 wt % mineral clay, in amounts relative to each other. In another embodiment, the combination and/or composition comprises 20-30 wt % silica, 0.5-3.5 wt % glucans, 0.5-6.0 wt % mannans, and 60-70 wt % mineral clay, in amounts relative to each other.

In some embodiments, β-glucans and mannans are obtained from yeast or yeast cell wall or an extract thereof. In such embodiments, a combination and/or composition comprising silica, mineral clay, glucan and mannans may comprise, consist essentially of, or consist of, 1-40 wt % silica, 1-30 wt % yeast cell wall or an extract thereof, and 40-92 wt % mineral clay, in amounts relative to each other. In one embodiment, such a combination and/or composition comprises 10-40 wt % silica, 5-20 wt % yeast cell wall or an extract thereof, and 40-80 wt % mineral clay, in amounts relative to each other. In another embodiment, the combination and/or composition comprises 15-30 wt % silica, 5-15 wt % yeast cell wall or an extract thereof, and 50-70 wt % mineral clay, in amounts relative to each other.

In any of the above embodiments, a combination and/or composition comprising silica, mineral clay, glucan and mannans may further comprise an endoglucanohydrolase, such as β-1,3 (4)-endoglucanohydrolase. Such a combination and/or composition may include from 0.025 wt % endoglucanohydrolase to 5 wt % endoglucanohydrolase or more, such as from 0.05 wt % to 3 wt % β-1,3 (4)-endoglucanohydrolase, relative to the amounts of silica, mineral clay, glucan, mannans, and/or yeast, yeast cell wall, or yeast cell wall extract present in the combination and/or composition. In one embodiment, the combination and/or composition comprises 0.1-3 wt % β-1,3 (4)-endoglucanohydrolase, 20-40 wt % silica, 0.5-20 wt % glucan and mannans, and 50-70 wt % mineral clay, in amounts relative to each other. In another embodiment, the combination and/or composition comprises 0.1-3 wt %, β-1,3 (4)-endoglucanohydrolase, 20-40 wt % silica, 0.5-10 wt % glucan and mannans, and 50-70 wt % mineral clay, in amounts relative to each other. Alternatively, in addition to the primary combination and/or composition, a combination and/or composition may comprise, consist essentially of, or consist of, 0.1-3 wt % β-1,3 (4)-endoglucanohydrolase, 1-40 wt % silica, 5-30 wt % yeast cell wall or an extract thereof, and 40-92 wt % mineral clay, in amounts relative to each other. In one embodiment, the combination and/or composition comprises 0.1-3 wt % β-1,3 (4)-endoglucanohydrolase, 10-40 wt % silica, 5-20 wt % yeast cell wall or an extract thereof, and 40-80 wt % mineral clay, in amounts relative to each other. In another embodiment, the combination and/or composition comprises 0.1-3 wt % β-1,3 (4)-endoglucanohydrolase, 15-30 wt % silica, 5-15 wt % yeast cell wall or an extract thereof, and 50-70 wt % mineral clay, in amounts relative to each other.

β-1,3 (4)-endoglucanohydrolase, diatomaceous earth, yeast cell wall or an extract thereof, and mineral clay may be combined at 0.05-3%, 1-40%, 1-20% and 40-92% by weight, respectively. Alternatively, β-1,3 (4)-endoglucanohydrolase, diatomaceous earth, yeast cell wall or an extract thereof, and mineral clay may be combined at 0.1-3%, 5-40%, 2-15% and 40-80% by weight, respectively, or at 0.1-3%, 30-40%, 4-15% and 50-65% by weight, respectively.

The glucan and mannans (or yeast or yeast cell wall or an extract thereof) can be prepared by a method known to a person of ordinary skill in the art. Yeast cell wall or an extract thereof may have a composition comprising 0-15% moisture and 85-100% dry matter. The dry matter may comprise 10-65% protein, 0-25% fats, 0-3% phosphorus, 5-30% β-glucan, 5-35% mannans, and 0-15% ash. In an independent embodiment, a commercial source of β-1,3 (4) glucan and glucomannan derived from primary inactivated yeast (such as *Saccharomyces cerevisiae*) with the following chemical feed supplement can be used: moisture 2-5%; proteins 40-50%; fats 3-8%; phosphorus 0-2%; mannans 10-16%; β-1,3-(4) glucan 10-20%; and ash 2-12%.

In another independent embodiment, the yeast cell wall or an extract thereof comprises moisture 1-7% and dry matter 93-99%, and the dry matter may comprise proteins 18-28%, fats 10-17%, phosphorus 0-2%, mannans 20-30%, β-1,3-(4) glucan 18-28%, and ash 2-5%.

In some embodiments, the combination and/or composition comprises the primary combination and/or composition, and a composition I that comprises, consists essentially of, or consists of, silica, mineral clay, glucan and mannans, and optionally further includes endoglucanohydrolase. In some embodiments, composition I comprises, consists essentially of, or consists of, silica, mineral clay, glucan, mannans, and optionally endoglucanohydrolase, in the relative amounts disclosed herein. And in certain embodiments of composition I, glucan and mannans is provided by yeast cell wall, or an extract thereof.

Composition I may further comprise one or more additional components. Additional components may be used for any desired purpose, such as a substantially biologically inert material added, for example, as a filler, or to provide a desired beneficial effect. For example, composition I may include a carbonate (including a metal carbonate such as calcium carbonate); a trace mineral, such as, but not limited to, chloride, fluoride, iodide, chromium, copper, zinc, iron, magnesium, manganese, molybdenum, phosphorus, potassium, sodium, sulfur, selenium, or a combination thereof, a bulking agent; a micro tracer, such as iron particles coated with a dye; yeast; allicin; alliin; allinase; algae; a polyphenol or plant material comprising polyphenol; a carrier; a colorant; a taste enhancer; a preservative; an oil; a vitamin; a sorbic acid or a salt thereof, or a combination thereof. The yeast may be yeast culture, active yeast, a live yeast, a dead yeast, yeast extract, or a combination thereof. The preservative may be benzoic acid or a salt thereof, e.g. sodium benzoate; lactic acid or a salt thereof, e.g. sodium lactate, potassium lactate or calcium lactate; propionic acid or a salt thereof, e.g. sodium propionate; ascorbic acid or a salt thereof, e.g. sodium ascorbate; gallic acid or a salt thereof e.g. sodium gallate; sulfur dioxide and/or sulfites; nitrites; nitrates; choline, or a salt thereof, such as an anion salt of choline, e.g. choline halide, such as chloride, bromide, iodide, fluoride, or choline hydroxide; or any combination thereof. The oil may be mineral oil, corn oil, soybean oil, or a combination thereof. The sorbic acid or salt thereof may be potassium sorbate, sodium sorbate, ammonium sorbate, or a combination thereof. The vitamin may be vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, or a combination thereof.

In some embodiments, composition I does not comprise additional components. In other embodiments, composition I comprises from greater than zero to 40% or more by weight additional components, such as from 0.10% to 40% by weight, or from 0.2% to 35% by weight additional components. In certain embodiments, composition I comprises from 0.1% to 5% by weight additional components, such as from 0.2% to 3% by weight. In other embodiments, composition I comprises from 5% to 20% by weight additional components, such as from 10% to 15% by weight. And in further embodiments, composition I comprises from 20% to 40% by weight additional components, such as from 30% to 35% by weight additional components.

In certain embodiments, composition I is a powdered composition. In other embodiments, composition I is a granulated composition. Such a granulated composition may comprise silica, mineral clay, glucan and/or mannans, and optionally endoglucanohydrolase as discussed above. Granulated composition I may have a bulk loose density of from 40 lb/ft$^3$ to 150 lb/ft$^3$; a bulk density difference between a bulk density of a loose packed sample and a bulk density of a tapped or agitated sample of less than 15 lb/ft$^3$; a dispersion value of 20% or less at 2 minutes; a dispersion value of 15% or less at 5 minutes; or a dispersion value of 10% or less at 10 minutes. And/or each granule in the composition may have a specific density of from 50 lb/ft$^3$ to 150 lb/ft$^3$. In some embodiments, each granule in the granular composition comprises silica, mineral clay, glucan and/or mannans, and optionally endoglucanohydrolase, in relative amounts substantially the same as a relative amount of each ingredient in the composition as whole. Each granule in the granular composition may comprise, consist essentially of, or consist of, silica, mineral clay, glucan, mannans and endoglucanohydrolase. Alternatively, or additionally, each granule may comprise a substantially homogenous blend of silica, mineral clay, glucan and mannans, and optionally endoglucanohydrolase. The granular composition may comprise greater than 40% by weight granules having at least one dimension between 0.149 mm (100 mesh, U.S. standard mesh size) and 4.76 mm (4 mesh), and in some embodiments, the granular composition comprises greater than 90% by weight granules having at least one dimension, and may be 1, 2 or 3 dimensions, between 0.149 mm (100 mesh) and 2 mm (10 mesh). And/or the granular composition may comprise from greater than 0% to 100% granules by weight and from 0% to no more than 60%, such as no more than 10%, particles by weight, the granules having at least one dimension, and may be 1, 2 or 3 dimensions, between 10 mesh (2.00 mm) and 100 mesh (0.149 mm), and the particles having at least one dimension, and may be 1, 2 or 3 dimensions, of less than (i.e., smaller than) 100 mesh (0.149 mm). In any embodiments, the granular composition comprises plural granules, each granule comprising silica, mineral clay, glucan and mannans, the granules having a size that when administered to an animal increases expression of interleukin 10 receptor β (IL10RB) for a time period subsequent to administration, such as subsequent to the onset of administration, relative to an animal that does not receive the composition. In some embodiments, the time period may be from the start of administration to from 28 days to at least 42 days. And/or the granular composition may have a mineral coefficient of variation of from 0% to 10%, or a proximate coefficient of variation of from 0% to 20%, or both. Additional information concerning the granular feed supplement can be found in U.S. application Ser. No. 15/878,761 which is incorporated herein by reference in its entirety.

In some embodiments, a combination and/or composition that comprises silica, mineral clay, glucan and mannans may comprise silica, mineral clay, glucan, mannans, and endoglucanohydrolase; silica, mineral clay, glucan, mannans, endoglucanohydrolase, micro tracers and mineral oil; silica, mineral clay, glucan, mannans, endoglucanohydrolase, micro tracers, mineral oil, and vitamins; silica, mineral clay, glucan, mannans, endoglucanohydrolase, micro tracers, mineral oil, vitamins, and potassium sorbate; silica, mineral clay, glucan, mannans, endoglucanohydrolase, vitamins, and active yeast; silica, mineral clay, glucan, mannans, endoglucanohydrolase, micro tracers, mineral oil, and active yeast; silica, mineral clay, glucan, mannans, endoglucanohydrolase, and mineral oil; silica, mineral clay, glucan, mannans, endoglucanohydrolase, vitamins, and calcium carbonate; silica, mineral clay, glucan, mannans, endoglucanohydrolase, micro tracers, and wheat fiber; or silica, mineral clay, glucan, mannans, endoglucanohydrolase, and micro tracers. In any of these embodiments, the glucan and mannans may be provided by yeast, yeast cell wall, or yeast cell wall extract.

In some embodiments, the disclosed combination and/or composition is administered to an animal in a sufficient amount and at suitable time intervals to provide the silica, mineral clay, glucan, mannans and optionally endoglucanohydrolase, optionally provided as composition I, in an amount and at a time interval believed or determined to be effective for achieving a beneficial result. The silica, mineral clay, glucan, mannans and optionally endoglucanohydrolase may be administered in a single dose daily or in divided doses throughout the day. The amount may be from greater than zero to 500 grams per animal per day, such as from 0.5 grams to 250 grams, from 5 grams to 200 grams, or from 10 grams to 70 grams per animal per day. Alternatively, the combination and/or composition is administered to provide the silica, mineral clay, glucan, mannans and optionally endoglucanohydrolase in an amount of from greater than zero to 1000 mgs or more per kilogram of the animal's body weight per day, such as from greater than zero to 500 mgs per kilogram body weight. In other embodiments, silica, mineral clay, glucan, mannans and optionally endoglucanohydrolase are fed or administered per weight of animal feed. The combination and/or composition may be administered to provide the silica, mineral clay, glucan, mannans and optionally endoglucanohydrolase in an amount of from greater than zero to 150 kg per ton (2000 pounds) of feed, such as from 0.1 kg to 100 kg per ton, from 0.1 kg to 50 kg per ton, from 0.1 kg to 25 kg per ton, from 0.1 kg to 10 kg per ton, from 0.1 kg to 5 kg per ton, from 0.5 kg to 5 kg per ton, from 0.5 kg to 2 kg per ton, or from 1 kg to 2 kg per ton of feed. Alternatively, the silica, mineral clay, glucan, mannans and optionally endoglucanohydrolase may be fed or administered in an amount of from greater than zero to 20 grams per kilogram of feed, such as from greater than zero to 10 grams per kilogram of feed, or from 0.1 grams to 5 grams per kilogram of feed.

Additionally, or alternatively, when expressed as a percentage of dry matter of feed, the disclosed composition and/or combination may be added to animal feed in an amount sufficient to provide silica, mineral clay, glucan, mannans, and optionally endoglucanohydrolase, in an amount of from greater than zero to 5% or more by weight of the combination and/or composition in the feed, such as from 0.01% to 2.5% by weight, from 0.0125% to 2% by weight, from 0.05 to 1.5% by weight, from 0.06% to 1% by weight, from 0.1 to 0.7% by weight, or from 0.125% to 0.5% by weight.

Alternatively, disclosed compositions and/or combinations may be administered such that the silica, mineral clay, glucan, mannans, and optionally endoglucanohydrolase, may be fed directly to animals as a supplement in amounts of from greater than 0.01 gram to 20 gram per kilogram of live body weight, such as from 0.01 gram to 10 gram per kilogram of live body weight, from 0.01 gram to 1 gram per kilogram of live body weight, from 0.01 gram to 0.5 gram per kilogram of live body weight, or from 0.02 gram to 0.4 gram per kilogram of live body weight per day. In some embodiments, the silica, mineral clay, glucan, mannans, and optionally endoglucanohydrolase, may be provided for use with many mammalian species, including non-human mammals, in amounts of from 0.05 grams to 0.20 grams per kilogram of live body weight per day.

By way of example, for cattle, disclosed compositions and/or combinations comprising one or more growth factors and the silica, mineral clay, glucan, mannans, and optionally endoglucanohydrolase, may be provided in a sufficient amount such that the silica, mineral clay, glucan, mannans, and optionally endoglucanohydrolase, is provided in the range of from 10 grams per head per day to 70 grams per head per day, such as from 45 grams per head per day to 70 grams per head per day, or from 50 grams per head per day to 60 grams per head per day. A person of ordinary skill in the art will appreciate that the amount that is fed can vary depending upon a number of factors, including the animal species, size of the animal and type of the feedstuff to which the combination and/or composition is added.

For some embodiments concerning aquatic animals, disclosed compositions and/or combinations comprising one or more growth factors and the silica, mineral clay, glucan, mannans, and optionally endoglucanohydrolase, may be administered based on body weight, such as grams of the combination/composition per pound or kilogram body weight of fish per day, or in milligrams of the combination/composition per pound or kilograms of body weight. In a particular example, when administered to fish, the disclosed composition and/or combination may be administered in an amount sufficient to provide from greater than zero to 500 mg of the silica, mineral clay, glucan, mannans, and optionally endoglucanohydrolase, per kilogram of body weight per day, such as from 10 mg to 350 mg per kilogram of body weight per day or from 50 mg to 250 mg per kilogram of body weight per day.

Alternatively, embodiments of the disclosed composition and/or combination may be administered based on the amount of feed provided to the aquatic animals. In some embodiments, the amount of the combination provides the silica, mineral clay, glucan, mannans, and optionally endoglucanohydrolase, to the aquatic animals in an amount of from greater than zero to 10,000 mg per kilogram of feed or more, such as from 500 mg to 7,500 mg per kilogram of feed, or from 1,000 mg to 5,000 mg per kilogram of feed.

2. Yucca and/or Quillaja, or Extracts Thereof

Additionally, or alternatively, embodiments of the disclosed combination and/or composition comprising the primary combination and/or composition also may comprise yucca and/or quillaja plant material, or extracts thereof. Examples of yucca include, but are not limited to, *Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca elata, Yucca endlichiana, Yucca faxoniana, Yucca flamentosa, Yucca filifera, Yucca flaccida, Yucca gigantean, Yucca glauca, Yucca gloriosa, Yucca grandiflora, Yucca harrimaniae, Yucca intermedia, Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis, Yucca valida* or combinations thereof. In certain embodiments, the yucca is or comprises *Yucca schidigera*.

Examples of quillaja include, but are not limited to, *Quillaja brasiliensis, Quillaja lanceolata, Quillaja lancifolia, Quillaja molinae, Quillaja petiolaris, Quillaja poeppigii, Quillaja saponaria, Quillaja sellowiana, Quillaja smegmadermos* or combinations thereof. In certain embodiments, the quillaja is or comprises *Quillaja saponaria*.

A person of ordinary skill in the art will appreciate that, as used herein, a plant name, such as yucca or quillaja, may refer to the plant as a whole, or to any part of the plant, such as the roots, stem or trunk, bark, leaves, flower, flower stems, seeds, or a combination thereof. These plant parts may be used fresh, or dried, and may be whole, pulverized, or comminuted. The plant name may also refer to extracts from any part or parts of the plant, such as chemical extracts, or extracts obtained by pressing, or any other methods of concentrating or extracting oils or other extracts known to those in the art or that are hereafter discovered. Plant extracts may include compounds that are saponins, triterpenoids, polyphenols, antioxidants or resveratrol, or combinations thereof.

In some embodiments, a composition and/or combination comprising the primary combination and/or composition and yucca and/or quillaja is a composition comprising the primary combination and/or composition, yucca and/or quillaja, and optionally further comprising a feed. In other embodiments, the composition and/or combination is a combination comprising the primary combination and/or composition and yucca and/or quillaja, and the combination may be administered sequentially or simultaneously in any order. The combination and/or composition may comprise a composition comprising yucca and/or quillaja that may also include carriers and binding agents suitable to formulate the yucca and/or quillaja for administration to an animal. In certain embodiments, such a composition can be a commercially available product, such as a composition comprising

*Yucca schidigera* and *Quillaja saponaria*, sold under the trademark NUTRAFITO PLUS by Desert King International and/or MAGNI-PHI by Phibro Animal Health Corporation.

Embodiments of the disclosed combination and/or composition that comprise both yucca and quillaja may comprise relative amounts of yucca and quillaja of from greater than zero to less than 100% yucca and from greater than zero to less than 100% quillaja. In some embodiments, the combination and/or composition comprises 50% yucca and 50% quillaja relative to each other, such as 40% yucca: 60% quillaja, 30% yucca: 70% quillaja, 20% yucca: 80% quillaja, 15% yucca: 85% quillaja, 10% yucca: 90% quillaja, 5% yucca: 95% quillaja, or less than 5% yucca: more than 95% quillaja. In other embodiments, the amount of quillaja relative to the total amount of yucca and quillaja, is from 50% to less than 100%, such as from 60% to less than 100%, from 70% to less than 100%, from 80% to less than 100%, from 85% to less than 100%, from 95% to less than 100%, or from 95% to less than 100%. Particular embodiments of the combination and/or composition comprise 85% *Quillaja saponaria* and 15% *Yucca schidigera*, or 90% *Quillaja saponaria* and 10% *Yucca schidigera*, relative to each other.

The disclosed combination and/or composition may be administered in combination with a feed. The combination and/or composition may be administered in an amount suitable to provide a desired amount of yucca and/or quillaja. In some embodiments, an amount of yucca administered to an animal is from 0 to greater than 20 ounces per ton of feed, such as from greater than 0 to 20 ounces, from 1 to 10 ounces per ton of feed, or from 1 to 5 ounces. In other embodiments the amount of quillaja administered to an animal is from 0 to greater than 20 ounces per ton of feed, such as from greater than 0 to 20 ounces, from 1 to 10 ounces or from 1 to 5 ounces. In certain embodiments, both yucca and quillaja are administered, and the combination and/or composition is administered in an amount sufficient to provide a combined amount of yucca and quillaja of from greater than 0 to greater than 20 ounces per ton of feed, preferably from greater than 0 to 18 ounces, from 2 to 18, from 2 to 15, from 2 to 10, from 2 to 8, or from 2 to 6 ounces. In other embodiments, the combination and/or composition is administered in an amount sufficient to provide a combined amount of yucca and quillaja of from greater than 0 to greater than 500 grams per ton of feed, such as from greater than zero to 500 grams/ton, or from greater than zero to 250 grams/ton of feed. In certain embodiments, the combination and/or composition is administered in an amount sufficient to administer yucca and/or quillaja at from greater than 0 ppm to 500 ppm, such as from 50 ppm to 400 ppm, or from 100 ppm to 300 ppm. In certain embodiments, the combination and/or composition is administered in an amount sufficient to administer yucca and quillaja at from greater than 0 ppm to less than 125 ppm, such as from greater than 0 ppm to 124 ppm or from greater than 0 ppm to 100 ppm. In other embodiments yucca and quillaja is administered at from greater than 125 ppm to 500 ppm, such as from 126 ppm to 400 ppm, or from 150 ppm to 300 ppm. Additional information concerning embodiments of a combination comprising *Yucca*, quillaja and *Bacillus* can be found in U.S. Pat. No. 9,999,648, which is incorporated herein by reference in its entirety.

3. Probiotic

Embodiments of the disclosed composition and/or combination comprising the primary combination and/or composition may also comprise a probiotic, such as a direct fed microbial (DFM). Exemplary DFMs include, but are not limited to, a *Bacillus* species or a Bacilli combination. In one example, the Bacilli combination is a probiotic combination or a composition comprising plural bacilli. In certain particular embodiments, the composition and/or combination comprises three or four DFMs selected from *Bacillus coagulans, Bacillus subtilis, Bacillus licheniformis* and *Bacillus amyloliquefaciens*. A combination or composition comprising the DFMs *Bacillus amyloliquefaciens, Bacillus subtilis* and *Bacillus licheniformis* is referred to herein as an ASL combination. In some embodiments, an ASL combination comprises, consists essentially of, or consists of *Bacillus amyloliquefaciens, Bacillus subtilis* and *Bacillus licheniformis* and no additional DFMs. As used with respect to a probiotic, such as a DFM, the term 'consists essentially of' precludes additional probiotics or DFMs being included in the combination/composition. A combination or composition comprising the DFMs *Bacillus coagulans, Bacillus subtilis* and *Bacillus licheniformis* is referred to herein as an CSL combination. In some embodiments, an CSL combination comprises, consists essentially of, or consists of *Bacillus coagulans, Bacillus subtilis* and *Bacillus licheniformis* and no additional DFMs. An ASLC combination is a combination or composition comprising the DFMs *Bacillus amyloliquefaciens, Bacillus subtilis, Bacillus licheniformis* and *Bacillus coagulans*. In some embodiments, an ASLC combination comprises, consists essentially of, or consists of *Bacillus amyloliquefaciens, Bacillus subtilis, Bacillus licheniformis* and *Bacillus coagulans*, but no other additional DFMs.

In some embodiments, a Bacilli composition and/or combination, such as a CSL composition and/or combination, an ASL composition and/or combination, or an ASLC composition and/or combination, when combined with the primary combination and/or composition, and optionally with other additional components disclosed herein, and administered to a subject may provide a substantial benefit to the subject compared to a subject that is not administered such compositions and/or combinations. With particular reference to poultry, a Bacilli combination provides a substantial benefit with respect to one or more of feed conversion rate, average body weight, average body weight gain, body weight coefficient of variation, bird mortality, lesion scores, *Salmonella/E. Coli/Clostridium* perfingens (CP) incidence, and/or oocysts in fecal matter relative to poultry fed none, one, or two of these bacilli in any combination.

A. *Bacillus coagulans, Bacillus subtilis, Bacillus licheniformis* and/or *Bacillus amyloliquefaciens*

A person of ordinary skill in the art will appreciate that any strain, or combinations of strains, of *Bacillus coagulans, Bacillus subtilis, Bacillus licheniformis* and/or *Bacillus amyloliquefaciens* can be used in the Bacilli combination. As used herein the terms "*Bacillus amyloliquefaciens,*" "*Bacillus coagulans,*" "*Bacillus subtilis*" and "*Bacillus licheniformis*" independently may refer to a single strain of the respective *Bacillus* species, or to multiple strains, such as 2, 3, 4, 5, 6, 7, 8, 9, 10 or more strains, of each respective *Bacillus* species. Solely by way of example and without limitation, certain acceptable exemplary strains of each *Bacillus* species are listed below.

i) *Bacillus coagulans* Strains

*Bacillus coagulans* Hammer ATCC® BAA-738™ strain LMG 17453, Logan B0934, NCTC 3992, Vitek #202384, *Bacillus coagulans* Hammer ATCC® 7050™ strain NRS 609, NCIB 9365, NCTC 10334, DSM 1, CCM 2013, WDCM 00002, *Bacillus coagulans* Hammer ATCC® 8038™ strain NCA 43P, NCIB 8080, NRS 770, DSM 2312 deposited with ATCC as *Bacillus thermoacidurans* by Berry,

*Bacillus coagulans* Hammer ATCC® 10545™ strain NRS 784, NCIB 8041, DSM 2311, CCM 1082, deposited with ATCC as *Bacillus dextrolacticus* by Andersen and Werkman, *Bacillus coagulans* Hammer ATCC® 11014™ strain NRS T27, 78G, DSM 2383, *Bacillus coagulans* Hammer ATCC® 11369™ strain C, DSM 2384 deposited with ATCC as *Bacillus dextrolacticus* by Andersen and Werkman, *Bacillus coagulans* Hammer ATCC® 12245™ strain NCA 308, DSM 2308, NCIB 8870, *Bacillus coagulans* Hammer ATCC® 15949™ strain NCA 4259, DSM 2385, *Bacillus coagulans* Hammer ATCC® 23498™ strain M-39, DSM 2314, NCIB 10276 deposited with ATCC as *Bacillus racemilacticus* by Nakayama and Yanoshi, *Bacillus coagulans* Hammer ATCC® 31284™ deposited with ATCC as *Lactobacillus sporogenes* by Horowitz-Wiassowa and Nowotelnow, Ganeden Biotech Inc.'s GBI-30 strain, ATCC Designation Number PTA-6086, *Bacillus coagulans* Hammer ATCC® 53595™ strain PM-1000, *Bacillus coagulans* Hammer strain DSM 2350, NRRL-NRS 2012, *Bacillus coagulans* Hammer strain DSM 2356, NCIB 8523, N.R. Smith (NRS) 798, B. Hammer Iowa State College 200, *Bacillus coagulans* Hammer strain DSM 30760, *Bacillus coagulans* Hammer strain ST109070 (IMET), 1032-005, *Bacillus coagulans* Hammer strain ST109076 (IMET), 1141-003, *Bacillus coagulans* Hammer strain ST109080 (IMET), 1136-014, *Bacillus coagulans* Hammer strain ST109208 (IMET), 491-25, *Bacillus coagulans* Hammer strain ST109210 (IMET), 485-59, *Bacillus coagulans* Hammer strain NCIB 700460, Thl, *Bacillus coagulans* Hammer strain NCIB 701099, BG5, TH27 (205), *Bacillus coagulans* Hammer strain NCIB 701159, 254, and *Bacillus coagulans* Hammer strain NCIB 701164, 259.

ii) *Bacillus licheniformis* Strains

*Bacillus licheniformis* (Weigmann) Chester ATCC® 6598™ strain NRS 745 deposited with ATCC as *Bacillus subtilis* by (Ehrenberg) Cohn, *Bacillus licheniformis* (Weigmann) Chester ATCC® 6634™ strain NRS 304, *Bacillus licheniformis* (Weigmann) Chester ATCC® 8480™ strain NRS 1128, *Bacillus licheniformis* (Weigmann) Chester ATCC® 9259™, *Bacillus licheniformis* (Weigmann) Chester ATCC® 9789™ strain AMNH 723, ATCC 102, ATCC 4527, ATCC 8243, ATCC 9800, NCTC 2586, NCTC 6346, NRS 243, NRS 978, W. Ford 1, DSM 8785, DSM 46308, BU 171, CCDB b-30, CCEB 631, CCM 2205, CN 1060, HNCMB 101012, IFO 12195, IFO 12196, IMET 11025, NBRC 12195, NBRC 12196, NCDO 735, NCDO 835, NCIB 6346, NCIB 8059, NCIB 8061, OUT 8367, OUT 8368, Smith 243, Smith 978, HankeyB13 deposited with ATCC as *Bacillus subtilis* by (Ehrenberg) Cohn, *Bacillus licheniformis* (Weigmann) Chester ATCC® 9945™ strain NRS 712, NCIB 8062 deposited with ATCC as *Bacillus subtilis* by (Ehrenberg) Cohn, *Bacillus licheniformis* (Weigmann) Chester ATCC® 9945a™ strain CD-2, NCIB 11709, *Bacillus licheniformis* (Weigmann) Chester ATCC® 10716™ strain ATCC 11944, BS 2181, Boots 1343, CCM 2181, FDA BT1, NCIB 8874, NRS 1330, Tracy I, DSM 603, IFO 12199, NBRC 12199, *Bacillus licheniformis* (Weigmann) Chester ATCC® 11945™ strain 1331, FDA BT3, *Bacillus licheniformis* (Weigmann) Chester ATCC® 11946™ strain 1333, B-1001, *Bacillus licheniformis* (Weigmann) Chester ATCC® 12139™ strain CSC deposited with ATCC as *Bacillus subtilis* by (Ehrenberg) Cohn, *Bacillus licheniformis* (Weigmann) Chester ATCC® 12713™ strain PRL B479, NRRL B-1001, *Bacillus licheniformis* (Weigmann) Chester ATCC® 12759™ strain ATCC 11560, Damodaron P-8, LMG 7560, NRS 1415, Vitek #200148, NCIB 8549, HankeyB133, P8, *Bacillus licheniformis* (Weigmann) Chester ATCC® 12759-MINI-PACK™ strain ATCC 11560, Damodaron P-8, LMG 7560, NRS 1415, Vitek #200148, *Bacillus licheniformis* (Weigmann) Chester ATCC® 13438™ Strain NCTC 8233, M. II strain, *Bacillus licheniformis* (Weigmann) Chester ATCC® 14409™ strain 620, NRS 1114, NCIB 1042, deposited with ATCC as *Bacillus abysseus* by ZoBell and Upham, *Bacillus licheniformis* (Weigmann) Chester ATCC® 14580™ strain (Gibson) 46, NCIB 9375, NCTC 10341, NRS 1264, DSM 13, CCM 2145, IFO 12200, NBRC 12200, WDCM 00068, *Bacillus licheniformis* (Weigmann) Chester ATCC® 14580D-5™ strain designation: Genomic DNA from *Bacillus licheniformis* Strain 46 [ATCC® 14580™]*Bacillus licheniformis* (Weigmann) Chester ATCC® 14594™, *Bacillus licheniformis* (Weigmann) Chester ATCC® 21038™ strain L-065, *Bacillus licheniformis* (Weigmann) Chester ATCC® 21039™, *Bacillus licheniformis* (Weigmann) Chester ATCC® 21415™ strain NS 1 deposited with ATCC as *Bacillus subtilis* by (Ehrenberg) Cohn, *Bacillus licheniformis* (Weigmann) Chester ATCC® 21417™ strain M deposited with ATCC as *Bacillus subtilis* (Ehrenberg) Cohn, *Bacillus licheniformis* (Weigmann) Chester ATCC® 21418™ deposited with ATCC as *Bacillus subtilis* by (Ehrenberg) Cohn, *Bacillus licheniformis* (Weigmann) Chester ATCC® 21424™ strain DSM 1969, *Bacillus licheniformis* (Weigmann) Chester ATCC® 21610™ strain B-201-7 deposited with ATCC as *Bacillus subtilis* (Ehrenberg) Cohn, *Bacillus licheniformis* (Weigmann) Chester ATCC® 21667™ strain FD 23612, *Bacillus licheniformis* (Weigmann) Chester ATCC® 21733™ strain DSM 1913 deposited with ATCC as *Bacillus subtilis* by (Ehrenberg) Cohn, *Bacillus licheniformis* (Weigmann) Chester ATCC® 25972™ strain 749/C, DSM 8782, DSM 46217, IMET10723, NCIB 9443, *Bacillus licheniformis* (Weigmann) Chester ATCC® 27326™ strain OM-81, *Bacillus licheniformis* (Weigmann) Chester ATCC® 27811™ strain 584, FERM-P 1038, *Bacillus licheniformis* (Weigmann) Chester ATCC® 31667™ strain DG 14, *Bacillus licheniformis* (Weigmann) Chester ATCC® 31972™ strain PM-3, *Bacillus licheniformis* (Weigmann) Chester ATCC® 33632™ strain (IOC) 2390, NCIB 11672, *Bacillus licheniformis* (Weigmann) Chester ATCC® 39326™ *Bacillus licheniformis* (Weigmann) Chester ATCC® 53757™ strain PWD-1, *Bacillus licheniformis* (Weigmann) Chester ATCC® 53926™ strain E312, *Bacillus licheniformis* (Weigmann) Chester ATCC® 55768™ strain O.W.U. 138B [OWU 138B], *Bacillus licheniformis* (Weigmann) Chester strain DSM 15, C, *Bacillus licheniformis* (Weigmann) Chester strain DSM 392, *Bacillus licheniformis* (Weigmann) Chester strain DSM 394, *Bacillus licheniformis* (Weigmann) Chester strain DSM 7259, NRRL-NRS 1263, *Bacillus licheniformis* (Weigmann) Chester strain DSM 7459, *Bacillus licheniformis* (Weigmann) Chester strain DSM 11258, *Bacillus licheniformis* (Weigmann) Chester strain DSM 11259, *Bacillus licheniformis* (Weigmann) Chester strain DSM 12369, *Bacillus licheniformis* (Weigmann) Chester strain DSM 12370, *Bacillus licheniformis* (Weigmann) Chester strain DSM 26543, *Bacillus licheniformis* (Weigmann) Chester strain DSM 28096, *Bacillus licheniformis* (Weigmann) Chester strain DSM 28591, *Bacillus licheniformis* (Weigmann) Chester strain DSM 30523, *Bacillus licheniformis* (Weigmann) Chester strain DSM 30535, *Bacillus licheniformis* (Weigmann) Chester strain DSM 30542, *Bacillus licheniformis* (Weigmann) Chester strain DSM 30585, *Bacillus licheniformis* (Weigmann) Chester strain DSM 30615, *Bacillus licheniformis* (Weigmann) Chester strain DSM 30620, *Bacillus licheniformis* (Weigmann) Chester strain DSM 30624, *Bacillus*

*licheniformis* (Weigmann) Chester strain DSM 30643, *Bacillus licheniformis* (Weigmann) Chester strain DSM 30654, *Bacillus licheniformis* (Weigmann) Chester strain DSM 30724, *Bacillus licheniformis* (Weigmann) Chester strain DSM 30766, *Bacillus licheniformis* (Weigmann) Chester strain DSM 30769, *Bacillus licheniformis* (Weigmann) Chester strain DSM 30778, *Bacillus licheniformis* (Weigmann) Chester strain DSM 30779, *Bacillus licheniformis* (Weigmann) Chester strain DSM 30865, *Bacillus licheniformis* (Weigmann) Chester strain DSM 30926, *Bacillus licheniformis* (Weigmann) Chester strain DSM 30959, *Bacillus licheniformis* (Weigmann) Chester strain DSM 30960, *Bacillus licheniformis* (Weigmann) Chester strain DSM 30961, *Bacillus licheniformis* (Weigmann) Chester strain DSM 30976, *Bacillus licheniformis* (Weigmann) Chester strain DSM 31019, *Bacillus licheniformis* (Weigmann) Chester strain DSM 100653, *Bacillus licheniformis* (Weigmann) Chester strain DSM 100655, *Bacillus licheniformis* (Weigmann) Chester strain DSM 103059, *Bacillus licheniformis* (Weigmann) Chester strain NCIB 1525, 1229, *Bacillus licheniformis* (Weigmann) Chester strain NCIB 6816, Glaxo 417, *Bacillus licheniformis* (Weigmann) Chester strain NCIB 7224, Loos, *Bacillus licheniformis* (Weigmann) Chester strain NCIB 8536, P1, *Bacillus licheniformis* (Weigmann) Chester strain NCIB 8537, Ho, *Bacillus licheniformis* (Weigmann) Chester strain NCIB 9536, Gibson 1319, NRS 1553, *Bacillus licheniformis* (Weigmann) Chester strain NCIB 9667, 1, *Bacillus licheniformis* (Weigmann) Chester strain NCIB 9668, 2, *Bacillus licheniformis* (Weigmann) Chester strain NCIB 9669, 3, *Bacillus licheniformis* (Weigmann) Chester strain NCIB 10689, *Bacillus licheniformis* (Weigmann) Chester strain NCIB 11143, *Bacillus licheniformis* (Weigmann) Chester strain NCIB 11643, YNS7712R, *Bacillus licheniformis* (Weigmann) Chester strain NCIB 13497, *Bacillus licheniformis* (Weigmann) Chester strain NCIB 14014, DA33, *Bacillus licheniformis* B1 (NRRL Deposit Number B-50907), *Bacillus subtilis* B2 (Deposit Number B-50908), *Bacillus licheniformis* RW25 (NRRL Deposit Number B-50911), *Bacillus licheniformis* RW32 (NRRL Deposit Number B-50912), and *Bacillus licheniformis* RW41 (NRRL Deposit Number B-50913), *Bacillus licheniformis* BL21 (NRRL B-50134), *Bacillus licheniformis* 3-12a (NRRL B-50504), *Bacillus licheniformis* 4-2a (NRRL B-50506), *Bacillus licheniformis* 842 (NRRL B-50516), *Bacillus licheniformis* DSM 5749 (BioPlus® 2B, Chr. Hansen Bio Systems), and *Bacillus licheniformis* OBT618 (ATCC PTA-122188).

iii) *Bacillus subtilis* Strains

*Bacillus subtilis* (Ehrenberg) Cohn ATCC® 82™ strain AMC, ATCC 8037, NRS 315, *Bacillus subtilis* (Ehrenberg) Cohn ATCC® 82D-5™ strain designation: Genomic DNA from *Bacillus subtilis* strain AMC [ATCC® 82™], *Bacillus subtilis* (Ehrenberg) Cohn ATCC® 465™ strain NRS 743, *Bacillus subtilis* (Ehrenberg) Cohn ATCC® 4529™ strain 3, ATCC 8013, NCTC 2588, NRS 1004 deposited with ATCC as *Bacillus vulgatus* by Trevisan, *Bacillus subtilis* (Ehrenberg) Cohn ATCC® 4925™ strain NRS 740 deposited with ATCC as *Bacillus* nigrificans by Fabian and Nienhuis, *Bacillus subtilis* (Ehrenberg) Cohn ATCC® 4944™ strain NCTC, NRS 1106 deposited with ATCC as *Bacillus parvus*, *Bacillus subtilis* subspecies *subtilis* (Ehrenberg) Cohn ATCC® 6051™ strain Marburg strain, ATCC 6051-U, CCM 2216, CCRC 10255, CCUG 163B, CFBP 4228, CIP 52.65, DSM 10, IAM 12118, IFO 12210, IFO 13719, IFO 16412, IMET 10758, JCM 1465, LMG 7135, NCAIM B.01095, NCCB 32009, NCCB 53016, NCCB 70064, NCFB 1769, NCIB 3610, NCTC 3610, NRRL B-4219, NRS 1315, NRS 744, VKM B-501, NBRC 13719 deposited with ATCC as *Bacillus subtilis* (Ehrenberg) Cohn, *Bacillus subtilis* (Ehrenberg) Cohn ATCC® 6051a™ strain P31K6, *Bacillus subtilis* bacteriophage phi-e ATCC® 6051-B1™ strain Phi-e deposited with ATCC as phi e, *Bacillus subtilis* (Ehrenberg) Cohn ATCC® 6460™ strain NRS 259 deposited with ATCC as *Bacillus aterrimus* by Lehmann and Neumann, *Bacillus subtilis* (Ehrenberg) Cohn ATCC® 6461™ strain NRS 275, CN 2192, NCIB 8055 deposited with ATCC as *Bacillus aterrimus* by Lehmann and Neumann, *Bacillus subtilis* subspecies *spizizenii* Nakamura et al. ATCC® 6633™ strain NRS 231, DSM 347, CCM 1999, IAM 1069, NCIB 8054, NCTC 10400, WDCM 00003 deposited with ATCC as *Bacillus subtilis* (Ehrenberg) Cohn, *Bacillus subtilis* subspecies *spizizenii* Nakamura et al. ATCC® 6633D-5™ strain designation: Genomic DNA from *Bacillus subtilis* subspecies *spizizenii* strain NRS 231 [ATCC® 6633™] deposited with ATCC as *Bacillus subtilis* (Ehrenberg) Cohn, *Bacillus subtilis* subspecies *spizizenii* Nakamura et al. ATCC® CRM-6633™ strain NRS 231 deposited with ATCC as *Bacillus subtilis* (Ehrenberg) Cohn, *Bacillus subtilis* subspecies *spizizenii* Nakamura et al. ATCC® 6633-MINI-PACK™ strain NRS 231 deposited with ATCC as *Bacillus subtilis* (Ehrenberg) Cohn, *Bacillus subtilis* (Ehrenberg) Cohn ATCC® 6984™ strain NRS 747 deposited with ATCC as *Bacillus vulgatus* subspecies *hydrolyticus*, *Bacillus subtilis* (Ehrenberg) Cohn ATCC® 7003™ strain NRS 730, *Bacillus subtilis* (Ehrenberg) Cohn ATCC® 7058™ strain NRS 351, *Bacillus subtilis* (Ehrenberg) Cohn ATCC® 7059™ strain NRS 352, *Bacillus subtilis* (Ehrenberg) Cohn ATCC® 7060™ strain NRS 659, *Bacillus subtilis* (Ehrenberg) Cohn ATCC® 7067™ strain NRS 238, ATCC 7974, ATCC 8012, *Bacillus subtilis* (Ehrenberg) Cohn ATCC® 7480™ strain NRS 1107 deposited with ATCC as *Bacillus endoparasiticus* by (Benedek) Benedek, *Bacillus subtilis* (Ehrenberg) Cohn ATCC® 8188™ strain ATCC 8450, NRS 773 deposited with ATCC as Tyrothrix minimus, *Bacillus subtilis* (Ehrenberg) Cohn ATCC® 8473™ strain NRS 762, *Bacillus subtilis* (Ehrenberg) Cohn ATCC® 9466™ strain designation: FDA strain PCI 220 [BUCSAV 170, NCIB 8159, NRRL B-558, NRS 1088], *Bacillus subtilis* (Ehrenberg) Cohn ATCC® 9524™ strain 3R9675, NRS 1109, *Bacillus subtilis* (Ehrenberg) Cohn ATCC® 9799™ strain NCTC 6276, NRS 1125, *Bacillus subtilis* (Ehrenberg) Cohn ATCC® 9858™ strain NRS 237, NCIB 8063, *Bacillus subtilis* (Ehrenberg) Cohn ATCC® 9943™ strain NRS 979, *Bacillus subtilis* (Ehrenberg) Cohn ATCC® 10774™ strain BU169, NCIB 8872, *Bacillus subtilis* (Ehrenberg) Cohn ATCC® 10783™ strain NRRL B-543, *Bacillus subtilis* (Ehrenberg) Cohn ATCC® 11774™ strain NCTC 8236, DSM 2109, *Bacillus subtilis* (Ehrenberg) Cohn ATCC® 11838™ strain AMC 46-A-6 (strain I), NCIB 8850, *Bacillus subtilis* (Ehrenberg) Cohn ATCC® 12100™ strain NCA 1558, ND 957, *Bacillus subtilis* (Ehrenberg) Cohn ATCC® 12432™ strain MB 32, 56R188, ATCC 13597, NCIB 8993, *Bacillus subtilis* (Ehrenberg) Cohn ATCC® 12695™ strain 51-52, *Bacillus subtilis* (Ehrenberg) Cohn ATCC® 12711™ strain PRL B92, Ra, *Bacillus subtilis* (Ehrenberg) Cohn ATCC® 13542™, *Bacillus subtilis* (Ehrenberg) Cohn ATCC® 13933™ strain NRRL B-1471, *Bacillus subtilis* (Ehrenberg) Cohn ATCC® 13952™ strain 1346, *Bacillus subtilis* (Ehrenberg) Cohn ATCC® 14410™ strain 625, NRS 1115 deposited with ATCC as *Bacillus borborokoites* by ZoBell and Upham, *Bacillus subtilis* (Ehrenberg) Cohn ATCC® 14415™ strain 569, NRS 1120 deposited with ATCC as *Bacillus submarinus* by ZoBell and Upham, *Bacillus subtilis* (Ehrenberg)

Cohn ATCC® 14416™ strain 576, NRS 1121 deposited with ATCC as *Bacillus thalassokoites* by ZoBell and Upham, *Bacillus subtilis* (Ehrenberg) Cohn ATCC® 14593™ strain IAM 1145, *Bacillus subtilis* (Ehrenberg) Cohn ATCC® 14617™ strain A-1625, *Bacillus subtilis* (Ehrenberg) Cohn ATCC® 14660™ strain C30-1, *Bacillus subtilis* (Ehrenberg) Cohn ATCC® 14662™ strain C30-109, *Bacillus subtilis* (Ehrenberg) Cohn ATCC® 14807™ strain MB-155, *Bacillus subtilis* (Ehrenberg) Cohn ATCC® 15040™ strain SX-67, *Bacillus subtilis* (Ehrenberg) Cohn ATCC® 15041™ strain SX-92, *Bacillus subtilis* (Ehrenberg) Cohn ATCC® 15134™ deposited with ATCC as *Bacillus uniflagellatus* by Mann, *Bacillus subtilis* (Ehrenberg) Cohn ATCC® 15183™ strain 309, *Bacillus subtilis* (Ehrenberg) Cohn ATCC® 15244™ strain 3369, *Bacillus subtilis* (Ehrenberg) Cohn ATCC® 15245™ strain 3349, IAM 1-3 deposited with ATCC as *Bacillus natto* by Sawamura, *Bacillus subtilis* (Ehrenberg) Cohn ATCC® 15476™ strain M-4-45, *Bacillus subtilis* (Ehrenberg) Cohn ATCC® 15477™ strain M-24-1 deposited with ATCC as *Bacillus pumilus* by Meyer and Gottheil, *Bacillus subtilis* (Ehrenberg) Cohn ATCC® 15561™ strain K-X-1, A-1, *Bacillus subtilis* (Ehrenberg) Cohn ATCC® 15563™ strain Marburg, *Bacillus subtilis* bacteriophage SP8 ATCC® 15563-B1™ strain SP8 deposited with ATCC as SP8 bacteriophage, *Bacillus subtilis* (Ehrenberg) Cohn ATCC® 15575™ strain SB 19, *Bacillus subtilis* (Ehrenberg) Cohn ATCC® 15811™ strain 5380, *Bacillus subtilis* (Ehrenberg) Cohn ATCC® 15818™ strain RIA 445, *Bacillus subtilis* (Ehrenberg) Cohn ATCC® 15819™ strain RIA 447, *Bacillus subtilis* (Ehrenberg) Cohn ATCC® 15841™, *Bacillus subtilis* bacteriophage S-a ATCC® 15841-B1™ strain S-a deposited with ATCC as S-a bacteriophage, *Bacillus subtilis* (Ehrenberg) Cohn ATCC® 19659™ strain PRD 66, IFO 13722, *Bacillus subtilis* (Ehrenberg) Cohn ATCC® 19659-MINI-PACK™ strain PRD 66, IFO 13722, *Bacillus subtilis* (Ehrenberg) Cohn ATCC® 21008™ strain 182-H-86 deposited with ATCC as *Bacillus pumilus* by Meyer and Gottheil, *Bacillus subtilis* (Ehrenberg) Cohn ATCC® 21183™ strain 5221, *Bacillus subtilis* (Ehrenberg) Cohn ATCC® 21228™ strain SC 8548, SO-4, DSM 1970, *Bacillus subtilis* (Ehrenberg) Cohn ATCC® 21331™ strain IFO 35, *Bacillus subtilis* (Ehrenberg) Cohn ATCC® 21332™ strain IAM 1213, *Bacillus subtilis* (Ehrenberg) Cohn ATCC® 21394™ strain 4-3-Ky, DSM 1971 deposited with ATCC as *Bacillus subtilis* subspecies *sakainensis*, *Bacillus subtilis* (Ehrenberg) Cohn ATCC® 21555™ strain Y 13, *Bacillus subtilis* (Ehrenberg) Cohn ATCC® 21556™, *Bacillus subtilis* (Ehrenberg) Cohn ATCC® 21742™ strain AHr-5, *Bacillus subtilis* (Ehrenberg) Cohn ATCC® 21770™ strain SP-3 deposited with ATCC as *Bacillus cereus* by Frankland and Frankland, *Bacillus subtilis* (Ehrenberg) Cohn ATCC® 21951™ strain 716, IFO 13322 deposited with ATCC as *Bacillus pumilus* by Meyer and Gottheil, *Bacillus subtilis* (Ehrenberg) Cohn ATCC® 23059™ strain W23, *Bacillus subtilis* (Ehrenberg) Cohn ATCC® 23856™ strain EMG 50, SB19, *Bacillus subtilis* (Ehrenberg) Cohn ATCC® 23857™ strain 168, *Bacillus subtilis* (Ehrenberg) Cohn ATCC® 23857D-5™ strain Designation: Genomic DNA from *Bacillus subtilis* strain 168 [ATCC® 23857™], *Bacillus subtilis* (Ehrenberg) Cohn ATCC® 23858™ strain EMG 52, *Bacillus subtilis* (Ehrenberg) Cohn ATCC® 23859™ strain EMG 53, *Bacillus subtilis* (Ehrenberg) Cohn ATCC® 25369™ strain 24028 deposited with ATCC as *Bacillus pulvifaciens* by Nakamura, *Bacillus subtilis* (Ehrenberg) Cohn ATCC® 27328™ strain C, *Bacillus subtilis* (Ehrenberg) Cohn ATCC® 27370™ strain 168 M, *Bacillus subtilis* bacteriophage SPO1 ATCC® 27370-B1™ strain SPO1 deposited with ATCC as SPO1, *Bacillus subtilis* (Ehrenberg) Cohn ATCC® 27505™ strain K49, HER 1346 deposited with ATCC as *Bacillus subtilis* subspecies *amyloliquefaciens*, *Bacillus subtilis* (Ehrenberg) Cohn ATCC® 27689™ strain SB168 (trp-), *Bacillus subtilis* (Ehrenberg) Cohn ATCC® 29056™ strain SB100, *Bacillus subtilis* (Ehrenberg) Cohn ATCC® 29233™ strain X6, *Bacillus subtilis* (Ehrenberg) Cohn ATCC® 31002™ strain Ahr.AUr-9, FERM-1998, *Bacillus subtilis* (Ehrenberg) Cohn ATCC® 31028™ strain FD 6404 deposited with ATCC as *Bacillus globigii* by Migula, *Bacillus subtilis* (Ehrenberg) Cohn ATCC® 31091™ strain 1054, IFO 13586, *Bacillus subtilis* (Ehrenberg) Cohn ATCC® 31094™ strain 1097, IFO 13621, *Bacillus subtilis* (Ehrenberg) Cohn ATCC® 31098™ strain 1027, IFO 13585 deposited with ATCC as *Bacillus pumilus* by Meyer and Gottheil, *Bacillus subtilis* subspecies *subtilis* (Ehrenberg) Nakamura et al. ATCC® 31578™ strain DSM 6223, RUB 331, *Bacillus subtilis* (Ehrenberg) Cohn ATCC® 31954™ strain MO7S-16/11, *Bacillus subtilis* (Ehrenberg) Cohn ATCC® 33234™ strain NCIB 10106, *Bacillus subtilis* (Ehrenberg) Cohn ATCC® 35021™ strain 5230, NRS 6, *Bacillus subtilis* (Ehrenberg) Cohn ATCC® 35854™ strain NRRL B-3411, *Bacillus subtilis* (Ehrenberg) Cohn ATCC® 35946™ strain OSU 75, *Bacillus subtilis* subspecies *subtilis* (Ehrenberg) Nakamura et al. ATCC® 37014™ strain DSM 6224, BD170, pSA2100, *Bacillus subtilis* subspecies *subtilis* (Ehrenberg) Nakamura et al. ATCC® 37015™ strain DSM 4514, BD170, NCIB 11624, pUB110, *Bacillus subtilis* subspecies *subtilis* (Ehrenberg) Nakamura et al. ATCC® 37108™ strain DSM 4873, BGSC 1E32, BR151, pPL608, *Bacillus subtilis* subspecies *subtilis* (Ehrenberg) Nakamura et al. ATCC® 37128™ strain DSM 4554, BGSC 1E18, pE194, *Bacillus subtilis* subspecies *subtilis* (Ehrenberg) Nakamura et al. ATCC® 39090™ strain DSM 6198, BGSC 1S53, *Bacillus subtilis* (Ehrenberg) Cohn ATCC® 39320™ strain MB 4488, *Bacillus subtilis* (Ehrenberg) Cohn ATCC® 39374™ strain MB 3575, *Bacillus subtilis* (Ehrenberg) Cohn ATCC® 39706™ strain B1-20, *Bacillus subtilis* (Ehrenberg) Cohn ATCC® 43223™ strain ABM261, *Bacillus subtilis* (Ehrenberg) Cohn ATCC® 49343™ strain IMVS 0101, *Bacillus subtilis* (Ehrenberg) Cohn ATCC® 49760™ deposited with ATCC as *Bacillus globigii* by Migula, *Bacillus subtilis* (Ehrenberg) Cohn ATCC® 49822™ deposited with ATCC as *Bacillus globigii* by Migula, *Bacillus subtilis* (Ehrenberg) Cohn ATCC® 55033™ strain SMS274, *Bacillus subtilis* (Ehrenberg) Cohn ATCC® 55060™ strain MB 4974, *Bacillus subtilis* (Ehrenberg) Cohn ATCC® 55405™ strain 300, *Bacillus subtilis* subspecies inaquosorum ATCC® 55406™ strain DA33 deposited with ATCC as *Bacillus licheniformis* (Weigmann) Chester, *Bacillus subtilis* (Ehrenberg) Cohn ATCC® 55422™ strain SC 15257, *Bacillus subtilis* (Ehrenberg) Cohn ATCC® 55614™ strain 1.2, AQ153, *Bacillus subtilis* (Ehrenberg) Cohn ATCC® 55675™ strain BPO1, *Bacillus subtilis* subspecies *subtilis* (Ehrenberg) Nakamura et al. strain DSM 402, BRC 111470, NCIB 10106, *Bacillus subtilis* subspecies *spizenii* Nakamura et al. strain DSM 618, *Bacillus subtilis* subspecies *spizenii* Nakamura et al. strain DSM 1087, *Bacillus subtilis* (Ehrenberg) Cohn strain DSM 1088, IFO 13169, NBRC 13169, OUT 8353, *Bacillus subtilis* (Ehrenberg) Cohn strain DSM 1089, IFO 3026, NBRC 3026, OUT 8350, *Bacillus subtilis* subspecies *subtilis* (Ehrenberg) Nakamura et al. strain DSM 1090, OUT 8424, *Bacillus subtilis* subspecies *subtilis* (Ehrenberg) Nakamura et al. strain DSM 1091, OUT 8425, *Bacillus subtilis* (Ehrenberg) Cohn strain DSM 1092, IFO 3009, NBRC 3009, OUT 8235, *Bacillus subtilis* subspecies *subtilis* (Ehrenberg)

Nakamura et al. strain DSM 3256, IAM 1213, *Bacillus subtilis* subspecies *subtilis* (Ehrenberg) Nakamura et al. strain DSM 3257, IAM 1259, *Bacillus subtilis* (Ehrenberg) Cohn strain DSM 3258, IAM 1260, *Bacillus subtilis* (Ehrenberg) Cohn strain DSM 4181, NCA 72-52, SA 22, *Bacillus subtilis* subspecies *subtilis* (Ehrenberg) Nakamura et al. strain DSM 4393, pC194, SB202, *Bacillus subtilis* (Ehrenberg) Cohn strain DSM 4449, natto 3335 UM4, *Bacillus subtilis* (Ehrenberg) Cohn strain DSM 4450, natto 3335 UM8, pLS20, pBC16, *Bacillus subtilis* (Ehrenberg) Cohn strain DSM 4451 *Bacillus subtilis* (Ehrenberg) Cohn strain DSM 4515, DB163, pGR71, *Bacillus subtilis* (Ehrenberg) Cohn strain DSM 4608, BR157, pMW1, *Bacillus subtilis* subspecies *subtilis* (Ehrenberg) Nakamura et al. strain DSM 4750, 1E7, BGSC 1E7, pE194-cop6, *Bacillus subtilis* subspecies *subtilis* (Ehrenberg) Nakamura et al. strain DSM 4751, 1E34, BGSC 1E34, pAM77, *Bacillus subtilis* subspecies *subtilis* (Ehrenberg) Nakamura et al. strain DSM 4871, BD426, BGSC 1E21, pBD8, *Bacillus subtilis* subspecies *subtilis* (Ehrenberg) Nakamura et al. strain DSM 4872, BD466, BGSC 1E24, pBD10, *Bacillus subtilis* subspecies *subtilis* (Ehrenberg) Nakamura et al. strain DSM 4874, BGSC 1E38, pMK3, YB886, *Bacillus subtilis* subspecies *subtilis* (Ehrenberg) Nakamura et al. strain DSM 5213, BGSC 1A40, BR 151, *Bacillus subtilis* subspecies *subtilis* (Ehrenberg) Nakamura et al. strain DSM 5214, BD 393, BGSC 1A511, *Bacillus subtilis* subspecies *subtilis* (Ehrenberg) Nakamura et al. strain DSM 5545, BGSC 1A459/SU+ III, *Bacillus subtilis* subspecies *subtilis* (Ehrenberg) Nakamura et al. strain DSM 5547, *Bacillus subtilis* (Ehrenberg) Cohn strain DSM 5552, *Bacillus subtilis* (Ehrenberg) Cohn strain DSM 5611, NRRL B-360, *Bacillus subtilis* subspecies *subtilis* (Ehrenberg) Nakamura et al. strain DSM 5660, NRRL B-362, *Bacillus subtilis* subspecies *spizizenii* Nakamura et al. strain DSM 6395, BGSC 2A2, W23 2A2, WB 672, *Bacillus subtilis* (Ehrenberg) Cohn strain DSM 6397, BGSC 1A2, SB 491, *Bacillus subtilis* subspecies *spizizenii* Nakamura et al. strain DSM 6399, BGSC 2A1, SB 623 *Bacillus subtilis* subspecies *spizizenii* Nakamura et al. strain DSM 6405, BGSC 2A3, W23 SR, *Bacillus subtilis* subspecies *subtilis* (Ehrenberg) Nakamura et al. strain DSM 6887, BGSC 1A309, NP40, *Bacillus subtilis* subspecies *subtilis* (Ehrenberg) Nakamura et al. strain DSM 6889, 1A658, BGSC 1A658, DA 65 *Bacillus subtilis* subspecies *spizizenii* Nakamura et al. strain DSM 8439, CCM 2268, IAM 12021, *Bacillus subtilis* (Ehrenberg) Cohn strain DSM 13019, SSI MK1, *Bacillus subtilis* subspecies *spizizenii* Nakamura et al. strain DSM 15029, NRRL B-23049, *Bacillus subtilis* subspecies inaquosorum Rooney et al. strain DSM 21200, *Bacillus subtilis* (Ehrenberg) Cohn strain DSM 21393, *Bacillus subtilis* subspecies inaquosorum Rooney et al. strain DSM 22148, KCTC 13429, *Bacillus subtilis* (Ehrenberg) Cohn strain DSM 23521, *Bacillus subtilis* (Ehrenberg) Cohn strain DSM 23778, *Bacillus subtilis* (Ehrenberg) Cohn strain DSM 25152, *Bacillus subtilis* (Ehrenberg) Cohn strain DSM 28592, *Bacillus subtilis* (Ehrenberg) Cohn strain DSM 30512, *Bacillus subtilis* (Ehrenberg) Cohn strain DSM 30529, *Bacillus subtilis* (Ehrenberg) Cohn strain DSM 30533, *Bacillus subtilis* (Ehrenberg) Cohn strain DSM 30534, *Bacillus subtilis* (Ehrenberg) Cohn strain DSM 30540, *Bacillus subtilis* (Ehrenberg) Cohn strain DSM 30541, *Bacillus subtilis* (Ehrenberg) Cohn strain DSM 30551, *Bacillus subtilis* (Ehrenberg) Cohn strain DSM 30558, *Bacillus subtilis* (Ehrenberg) Cohn strain DSM 30562, *Bacillus subtilis* (Ehrenberg) Cohn strain DSM 30570, *Bacillus subtilis* (Ehrenberg) Cohn strain DSM 30581, *Bacillus subtilis* (Ehrenberg) Cohn strain DSM 30597, *Bacillus subtilis* (Ehrenberg) Cohn strain DSM 30642, *Bacillus subtilis* (Ehrenberg) Cohn strain DSM 30651, *Bacillus subtilis* (Ehrenberg) Cohn strain DSM 30652, *Bacillus subtilis* (Ehrenberg) Cohn strain DSM 30671, *Bacillus subtilis* (Ehrenberg) Cohn strain DSM 30676, *Bacillus subtilis* (Ehrenberg) Cohn strain DSM 30677, *Bacillus subtilis* (Ehrenberg) Cohn strain DSM 30682, *Bacillus subtilis* (Ehrenberg) Cohn strain DSM 30711, *Bacillus subtilis* (Ehrenberg) Cohn strain DSM 30723, *Bacillus subtilis* (Ehrenberg) Cohn strain DSM 30801, *Bacillus subtilis* (Ehrenberg) Cohn strain DSM 30924, *Bacillus subtilis* (Ehrenberg) Cohn strain DSM 30925, *Bacillus subtilis* (Ehrenberg) Cohn strain DSM 30927, *Bacillus subtilis* (Ehrenberg) Cohn strain DSM 30928, *Bacillus subtilis* (Ehrenberg) Cohn strain DSM 30929, *Bacillus subtilis* (Ehrenberg) Cohn strain DSM 30941, D1, *Bacillus subtilis* (Ehrenberg) Cohn strain DSM 30942, D-FC1, *Bacillus subtilis* (Ehrenberg) Cohn strain DSM 31008, *Bacillus subtilis* (Ehrenberg) Cohn strain DSM 31009, *Bacillus subtilis* (Ehrenberg) Cohn strain DSM 31010, *Bacillus subtilis* (Ehrenberg) Cohn strain DSM 31020, *Bacillus subtilis* (Ehrenberg) Cohn strain DSM 31021, *Bacillus subtilis* (Ehrenberg) Cohn strain DSM 31033, *Bacillus subtilis* (Ehrenberg) Cohn strain DSM 100605, *Bacillus subtilis* (Ehrenberg) Cohn strain DSM 100612, *Bacillus subtilis* (Ehrenberg) Cohn strain DSM 100613, *Bacillus subtilis* (Ehrenberg) Cohn strain DSM 100614, *Bacillus subtilis* (Ehrenberg) Cohn strain DSM 103044, *Bacillus subtilis* (Ehrenberg) Cohn strain DSM 103047, *Bacillus subtilis* (Ehrenberg) Cohn strain DSM 103051, *Bacillus subtilis* (Ehrenberg) Cohn strain DSM 103758, *Bacillus subtilis* AM0904 (NRRL Deposit Number B-50914), *Bacillus subtilis* AM0911 (NRRL Deposit Number B-50915), *Bacillus subtilis* NP122 (NRRL Deposit Number B-50910), *Bacillus subtilis* NP119B (NRRL Deposit Number B-50909), *Bacillus subtilis* BS18 (NRRL B-50633), *Bacillus subtilis* BS278 (NRRL 50634), *Bacillus subtilis* 4-7d (NRRL B-50505), *Bacillus subtilis* 3-5 h (NRRL B-50507), *Bacillus subtilis* AGTP BS3BP5 (NRRL B-50510), *Bacillus subtilis* BS918 (NRRL B-50508), *Bacillus subtilis* AGTP BS1013 (NRRL-50509), *Bacillus subtilis* AGTP 944 (NRRL B-50548), *Bacillus subtilis* AGTP BS442 (NRRL B-50542), *Bacillus subtilis* AGTP BS1069 (NRRL B-50544), *Bacillus subtilis* AGTP BS521 (NRRL B-50545), *Bacillus subtilis* B27 (NRRL B-50105), *Bacillus subtilis* 3A-P4 (PTA-6506), *Bacillus subtilis* 22C-P1 (PTA-6508), *Bacillus subtilis* BL21 (NRRL B-50134), *Bacillus subtilis* strain GB03, *Bacillus subtilis* strain QST713, *Bacillus subtilis* DSM 5750 (BioPlus® 2B, Chr. Hansen Bio Systems).

iv) *Bacillus amyloliquefaciens* Strains

*Bacillus amyloliquefaciens* (Fukumoto) Priest et al. (ATCC® 23350™), *Bacillus amyloliquefaciens* (Fukumoto) Priest et al. (ATCC® 23842™), *Bacillus amyloliquefaciens* SB 3296 (PTA-7548), *Bacillus amyloliquefaciens* (Fukumoto) Priest et al. (ATCC® 23843™), *Bacillus amyloliquefaciens* SB3297 (PTA-7549), *Bacillus amyloliquefaciens* (Fukumoto) Priest et al. (ATCC® BAA-390™), *Bacillus amyloliquefaciens* (Fukumoto) Priest et al. (ATCC® 23845™), *Bacillus amyloliquefaciens* (Fukumoto) Priest et al. (ATCC® 23844™), *Bacillus amyloliquefaciens* (Fukumoto) Priest et al. (ATCC® 31592™), *Bacillus amyloliquefaciens* (Fukumoto) Priest et al. (ATCC® 53495™), *Bacillus amyloliquefaciens* (Fukumoto) Priest et al. (ATCC® 49763™), *Bacillus amyloliquefaciens*: SB 3276 (PTA-7541), *Bacillus amyloliquefaciens*: PMBP-M7 (vial labeled BCRC PMBP-M7) (PTA-5819), *Bacillus amyloliquefaciens* SB 3284 (PTA-7545), *Bacillus amyloliquefaciens* SB 3288

(PTA-7546), *Bacillus amyloliquefaciens* MF215 (SB3446) (PTA-7790), *Bacillus amyloliquefaciens* SB 3283 (PTA-7544), *Bacillus amyloliquefaciens* MF 225 (SB 3448) (PTA-7791), *Bacillus* sp. (ATCC® 70038™, deposited as *Bacillus amyloliquefaciens* (Fukumoto) Priest et al.), *Bacillus amyloliquefaciens* OBT712 deposited as ATCC® PTA-122189.

B. Other DFM(s)

The disclosed primary combination and/or composition can also be administered to an animal in combination with one or more other DFMs, either in addition to, or as an alternative to, *Bacillus coagulans, Bacillus subtilis, Bacillus licheniformis* and/or *Bacillus amyloliquefaciens*. The other DFM(s) may be any DFM suitable for administration to the particular animal. In some embodiments, the animal is a bovine, such as a dairy cow. In some embodiments, the animal is an avian, such as a poultry, particularly a chicken or a turkey, and the other DFM is a DFM that provides a benefit to the avian. The other DFM may be, by way of example and without limitation, an additional *Bacillus* species, *Lactobacillus, Enterococcus, Bifidobacterium, Propionibacterium, Streptococcus, Pediococcus,* yeast, or a combination thereof.

Exemplary other DFMs include, but are not limited to, *Bacillus alcalophilus, Bacillus alvei, Bacillus aminovorans, Bacillus aneurinolyticus, Bacillus anthracis, Bacillus aquaemaris, Bacillus atrophaeus, Bacillus boroniphilus, Bacillus brevis, Bacillus caldolyticus, Bacillus centrosporus, Bacillus cereus, Bacillus circulans, Bacillus frmus, Bacillus flavothermus, Bacillus fusiformis, Bacillus galliciensis, Bacillus globigii, Bacillus infernus, Bacillus larvae, Bacillus laterosporus, Bacillus lentus, Bacillus megaterium, Bacillus mesentericus, Bacillus mucilaginosus, Bacillus mycoides, Bacillus natto, Bacillus pantothenticus, Bacillus polymyxa, Bacillus pseudoanthracis, Bacillus pumilus, Bacillus schlegelii, Bacillus sphaericus, Bacillus sporothermodurans, Bacillus stearothermophilus, Bacillus thermoglucosidasius, Bacillus thuringiensis, Bacillus vulgatis, Bacillus weihenstephanensis, Lactobacillus acidophilis, Lactobacillus plantarum, Lactobacillus casei, Lactobacillus gallinarum, Lactobacillus lactis, Lactobacillus salivarius, Lactobacillus reuteri, Lactobacillus bulgaricus, Bifidobacterium pseudolongum, Bifidobacterium thermophilium, Bifidobacterium longum, Bifidobacterium lactis, Bifidobacterium animalis, Bifidobacterium bifidum, Bifidobacterium infantis, Streptococcus bovis, Streptococcus faecium, Enterococcus faecium, Enterococcus faecalis, Enterococcus diacetylactis, Saccharomyces cerevisiae, Saccharomyces boulardii Aspergillus oryzae, Aspergillus niger, Selenomonas ruminantium, Megasphaera elsdenii, Propionibacterium freudenreichii, Propionibacterium shermanii, Propionibacterium acidipropionici, Propionibacterium fensenii, Prevotella bryantii, Pediococcus acidilactici, Pediococcus cerevisiae,* or a combination thereof. In certain embodiments, *Bacillus pumilus* may be administered in combination with the Bacilli combination.

In some embodiments, the probiotic, such as a DFM, is or comprises yeast.

The combination and/or composition may be administered in an amount sufficient to provide a desired amount of the probiotic, such as a DFM, to an animal administered the combination and/or composition. The combination and/or composition may be administered in an amount sufficient to provide the probiotic in an amount of from $10^5$ to $10^{12}$ CFU/gram, such as from $10^8$ to $10^{10}$ CFU/gram.

The probiotic may comprise one or more of the DFMs disclosed herein. In some embodiments, the probiotic is Bacilli combination, such as an ASL combination, an ASLC combination, or a CSL combination, as defined herein. In such embodiments, the relative amounts of *Bacillus coagulans, Bacillus subtilis, Bacillus licheniformis* and/or *Bacillus amyloliquefaciens* present in the Bacilli combination are selected to obtain a desired result. For certain embodiments, the Bacilli combination comprises from $10^5$ to $10^{12}$ CFU/gram, and more typically from $10^8$ to $10^{10}$ CFU/gram of each of the *Bacillus* species in the Bacilli combination.

In some embodiments, the Bacilli combination may be administered to provide different CFU ratios of the *Bacillus* species included therein. In some embodiments, the ratio of *Bacillus subtilis:Bacillus licheniformis* in the Bacilli combination may be from 2:1 to 1:2, and typically is 1:1, relative to each other. And with respect to other *Bacillus* species in the Bacilli combination, the total amount of *Bacillus subtilis* and *Bacillus licheniformis* (BSBL) relative to the other *Bacillus* species may be from greater than zero to 99%, such as from 10% to 90%, from 15% to 85%, from 20% to 80%, from 25% to 75%, from 35% to 65%, from 45% to 55%, or substantially 50%, based on CFU.

In some embodiments, the ASL combination may comprise, consist essentially of, or consist of, in amounts relative to each other, from 25% or less to 75% or more *Bacillus amyloliquefaciens* (BA) and from 75% or more to 25% or less BSBL. In certain embodiments, the ratio of BA to BSBL in the ASL combination is from 25%:75% BA:BSBL to 75%:25% BA:BSBL, and may be 50%:50% BA:BSBL.

In some embodiments, the ASLC combination may comprise, consist essentially of, or consist of, in amounts relative to each other, from 25% or less to 75% or more in total of *Bacillus amyloliquefaciens* (BA) and *Bacillus coagulans* (BC), and from 75% or more to 25% or less BSBL. In certain embodiments, the ratio of BA+BC to BSBL in the ASL combination is from 25%:75% BA+BC:BSBL to 75%:25% BA+BC:BSBL, and may be 50%:50% BA+BC:BSBL. The amounts of BA and BC, relative to each other may be from greater than zero to 99% BA relative to BC, such as from 10% to 90%, from 15% to 85%, from 20% to 80%, from 25% to 75%, from 35% to 65%, from 45% to 55%, or substantially 50% BA relative to BC, based on CFU.

For example, the CSL combination may comprise from $3.5 \times 10^9$ to $10 \times 10^9$ CFU *Bacillus coagulans* per gram of the CSL combination, such as from $4.1 \times 10^9$ to $7.5 \times 10^9$, from $5 \times 10^9$ to $6.4 \times 10^9$ or from $5 \times 10^9$ to $6 \times 10^9$ CFU *Bacillus coagulans*/gram. The CSL combination may comprise from $5 \times 10^8$ to $10 \times 10^8$ CFU *Bacillus subtilis* per gram of the CSL combination, such as from $6 \times 10^8$ to $8.7 \times 10^8$, from $6.9 \times 10^8$ to $9 \times 10^8$, or $7.2 \times 10^8$ to $8 \times 10^8$ CFU *Bacillus subtilis*/per gram. And the CSL combination may comprise from $5 \times 10^8$ to $10 \times 10^8$ CFU *Bacillus licheniformis* per gram of the CSL combination, such as from $6 \times 10^8$ to $8.7 \times 10^8$, from $6.9 \times 10^8$ to $9 \times 10^8$, or $7.2 \times 10^8$ to $8 \times 10^8$ CFU *Bacillus licheniformis* per gram.

In certain embodiments, the CSL combination may be administered to provide different CFU ratios of the three *Bacillus* species. For example, in one embodiment, the CSL combination ratio provides from 6 parts to 10 parts *Bacillus coagulans* to 1 part to 2 parts *Bacillus subtilis*, and from 1 part to 2 parts *Bacillus licheniformis*. The ratio of *Bacillus subtilis:Bacillus licheniformis* in the CSL combination may be from 2:1 to 1:2, and typically is 1:1. In certain embodiments, the CSL combination comprises $5 \times 10^9$ *Bacillus coagulans*, $8 \times 10^8$ *Bacillus subtilis*, and $8 \times 10^8$ *Bacillus licheniformis* per gram of the CSL combination.

Disclosed compositions and/or combinations comprising a probiotic, for example a *Bacillus* species or combination of Bacillus species, may be administered in an amount selected to provide a sufficient amount of the probiotic to provide a desired and/or beneficial result or enhancement in the animal. For example, in poultry the amount of the combination and/or composition may be sufficient to provide an amount of the probiotic of from greater than zero to 5 grams or more per head per day, such as from 0.5 to 2.5 grams per head per day, or from 0.5 grams to 1 gram per head per day. In embodiments concerning cattle, the amount of the combination and/or composition administered to cattle may be sufficient to provide an amount of the probiotic of from greater than zero to 75 grams or more per head per had, such as from 10 to 50 grams per head per day, or from 25 to 40 grams per head per day. And for swine the amount of the combination and/or composition administered may be sufficient to provide an amount of the probiotic of from greater than zero to 20 grams or more per head per day, such as from 2 to 10 grams per head per day, or from 4 to 7 grams per head per day. In some examples, the probiotic may be admixed with feed at from greater than zero to 50 grams or more per ton (2000 pounds) of feed, such as from 0.5 grams to 25 grams per ton, from 1 gram to 10 grams per ton, or from 2 grams to 8 grams per ton of feed.

4. Metal Chelates

Additionally, or alternatively, embodiments of the disclosed combination and/or composition may comprise the primary combination and/or composition and a metal chelate. A metal chelate comprises at least one metal ion and at least one ligand associated with, such as binding to, the metal ion(s). In some embodiments, the ligand(s) can chelate and/or coordinate with one or more biologically-, nutritionally- and/or biocidally-relevant metals to form a metal chelate. As understood by a person of ordinary skill in the art, relevant metals can be used, for example, as part of a nutritional or biological supplement; are known to be beneficial to animals; and/or are substantially non-toxic when administered in the amounts disclosed herein. Additionally, or alternatively, the metal may have a biocidal property, and may be administered as a metal chelate.

Exemplary metals may include, but are not limited to, iron, copper, zinc, manganese, chromium, calcium, potassium, sodium, magnesium, cobalt, nickel, molybdenum, vanadium, strontium, selenium, or a combination thereof. In some disclosed embodiments, the metal is selected to provide a metal ion having a valency of +1, +2, +3, or more. For certain disclosed embodiments, the metal ion has a valency of two or three, and in particular embodiments, the metal ion is, or comprises, iron (II) or iron (III).

In particular embodiments, the combination and/or composition comprises the primary combination and/or composition and one or more metal chelates comprising ferric (+3) ions, particularly, ferric tyrosine, ferric citrate, ferric lactate, ferric proteinate, and/or ferric lysine.

Additionally, or alternatively, metal chelates suitable for use in the disclosed combination and/or composition include, but are not limited to, metal chelates having a formula Formula I $$\left[ \begin{array}{c} (R)_m \\ X \diagdown \diagup Y^{\ominus} \\ Z \end{array} \right]_c [M^{a+}]_b.$$

With reference to Formula I:
m is 0, 1 or 2;
a is from 1 to 6 or more, such as from 2 or 3;
b is 1 or 2;
c is 1, 2 or 3;
X can be selected from —$C(R^1)_3$, OH, $CO_2R^1$, $CO_2H$, $OR^2$, $NH_2$, $NR^2H$, $NR^2R^3$, —$(C(R^1)_2)_nONO_2$, —$(C(R^1)_2)_nNO_2$, SH, $SR^2$ wherein each $R^1$, $R^2$ and $R^3$ independently is selected from hydrogen, aliphatic, haloaliphatic, haloheteroaliphatic, heteroaliphatic, aromatic, aliphatic-aromatic, heteroaliphatic-aromatic or any combination thereof, and n is 1 to 6;
Y can be selected from $NH_2$, $NHR^3$, $NR^3R^4$, SH, $OR^3$, OH wherein $R^3$ and $R^4$ can independently be selected from aliphatic, haloaliphatic, haloheteroaliphatic, heteroaliphatic, aromatic, aliphatic-aromatic, heteroaliphatic-aromatic or any combination thereof;
Z can be selected from O, S, NH, $NR^5$ wherein $R^5$ can be selected from aliphatic, haloaliphatic, haloheteroaliphatic, heteroaliphatic, aromatic, aliphatic-aromatic, heteroaliphatic-aromatic or any combination thereof; and
each R independently is selected from halogen, aliphatic, haloaliphatic, haloheteroaliphatic, heteroaliphatic, aromatic, aliphatic-aromatic, heteroaliphatic-aromatic, or any combination thereof; and
M is a metal ion as previously described.

In some embodiments, m is 1 or 2, i.e. m is not 0. In some embodiments, when X=—$C(R^1)_3$, then X and one $R^1$ together with the atoms to which they are attached form a cyclic ring, such as an aliphatic, heteroaliphatic, aryl, or heteroaryl ring.

In some embodiments of Formula I, the ligand is an acid, such that Z is O and Y is OH. The acid may be an amino acid (X is $NH_2$, $NR^2H$, or $NR^2R^3$) or a hydroxy acid X is OH), such as an α-hydroxy acid, a β-hydroxy acid, or a γ-hydroxy acid.

In particular disclosed embodiments, the metal chelate may have a structure according to any one of the following formulas:

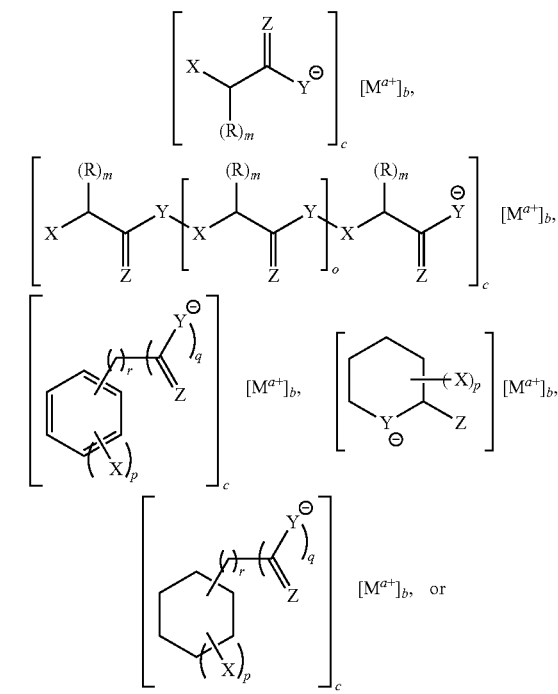

-continued

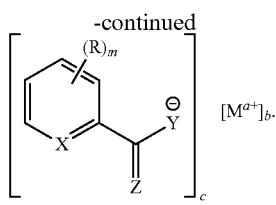

A person of ordinary skill in the art will understand that the above formulas, including Formula I, are stereoambiguous. That is, these formulas do not indicate the relative or absolute stereochemistry of the potential stereoisomers; nevertheless, all such stereoisomers are within the scope of the disclosed metal chelates.

The metal chelate may further comprise one or more counterions. The number and nature of the counterion(s) may be selected to result in a charge-neutral metal chelate. Suitable counterions include, but are not limited to, sodium, potassium, lithium, calcium, magnesium, chloride, bromide, iodine, fluoride, sulfate, carbonate, nitrate, hydroxide, or a combination thereof.

Further, in certain embodiments, a metal chelates disclosed herein may be formed using two or more different ligands. That is, an exemplary metal chelate disclosed herein may comprise a metal atom or its ion that binds with, for example, two lactic acid molecules and one oxalic acid molecule.

In some embodiments, the metal chelates disclosed herein can be metal complexes of aliphatic hydroxy acids, metal complexes of cyclic hydroxy acids (such as cyclic aliphatic hydroxy acids, aromatic hydroxy acids, etc.), metal complexes of carbohydrates, metal complexes of partially hydrolyzed or hydrolyzed proteins (such as, metal proteinates), metal complexes of amino acids, metal complexes of oligopeptides, salts and/or hydrates thereof; and any combinations thereof. In certain embodiments, the metal chelates disclosed herein can be iron (II) complexes of aliphatic hydroxy acids, iron (II) complexes of cyclic hydroxy acids (including, cyclic aliphatic hydroxy acids, aromatic hydroxy acids, etc.), iron (II) complexes of carbohydrates, iron (II) complexes of partially hydrolyzed or hydrolyzed proteins, iron (II) complexes of amino acids, iron (II) complexes of oligopeptides, or any combinations thereof. In certain embodiments, the metal chelates disclosed herein can be iron (III) complexes of aliphatic hydroxy acids, iron (III) complexes of cyclic hydroxy acids (such as, cyclic aliphatic hydroxy acids, aromatic hydroxy acids, etc.), iron (III) complexes of carbohydrates, iron (III) complexes of partially hydrolyzed or hydrolyzed proteins, iron (III) complexes of amino acids, iron (III) complexes of oligopeptides, or any combinations thereof.

In certain embodiments, metal complexes of the aliphatic hydroxy acids may include, but are not limited to, metal complexes of α-hydroxy acids, metal complexes of D-hydroxy acids, metal complexes of γ-hydroxy acids, or any combinations thereof. In particular disclosed embodiments, iron (II) complexes of the aliphatic hydroxy acids may include, but are not limited to, iron (II) complexes of α-hydroxy acids, iron (II) complexes of D-hydroxy acids, iron (II) complexes of γ-hydroxy acids, or any combinations thereof. Exemplary iron (II) complexes of α-hydroxy acids include, but are not limited to, ferrous lactate, ferrous glycolate, ferrous citrate, ferrous mandelate, ferrous tartrate, iron (II) salicylate, iron (II) p-hydroxy benzoate, ferrous complex of isoleucic acid, ferrous valate; salts and/or hydrates thereof. In particular disclosed embodiments, iron (III) complexes of the aliphatic hydroxy acids may include, but are not limited to, iron (III) complexes of α-hydroxy acids, iron (III) complexes of D-hydroxy acids, iron (III) complexes of γ-hydroxy acids, or any combinations thereof. Exemplary iron (III) complexes of α-hydroxy acids include, but are not limited to, ferric lactate, ferric glycolate, ferric citrate, ferric mandelate, ferric tartrate, ferric complex of isoleucic acid, ferric valate; salts and/or hydrates thereof. In certain embodiments, metal complexes of cyclic hydroxy acids (i.e., iron (II) complexes of cyclic hydroxy acids) may include, but are not limited to, ferrous quinate, ferrous complex of o-hydroxy benzoic acid, ferrous complex of m-hydroxy benzoic acid, ferrous complex of p-hydroxy benzoic acid, ferrous complex of pyridine-2-carboxylic acids, or any combinations thereof. Exemplary iron (III) complexes of cyclic hydroxy acids may include, but are not limited to, ferric quinate, ferric complex of o-hydroxy benzoic acid, ferric complex of m-hydroxy benzoic acid, ferric complex of p-hydroxy benzoic acid, iron (III) γ-hydroxy butyrate, ferric β-hydroxy butyrate, iron(III) m-hydroxy benzoate, iron (III) γ-hydroxy pentanoate, iron (III) β-hydroxy pentanoate, ferric β-hydroxy propionate, iron (III) p-hydroxy benzoate, iron (III) salicylate, ferric complex of pyridine-2-carboxylic acids, or any combinations thereof. Exemplary iron (II) complex of carbohydrates may include, but are not limited to, iron (II) complex of amino sugars (e.g., D-glucosamine, etc.), iron (II) complex of monosaccharides (e.g., D-glucose, L-glucose, ribose, arabinose, xylose, lyxose, galactose, gulose, mannose, etc.), iron (II) complex of disaccharides (e.g., sucrose, lactose, etc.) or any combinations thereof. Exemplary iron (III) complex of carbohydrates may include, but are not limited to, iron (III) complex of amino sugars (e.g., D-glucosamine, etc.), iron (III) complex of monosaccharides (e.g., D-glucose, L-glucose, ribose, arabinose, xylose, lyxose, galactose, gulose, mannose, etc.), iron (III) complex of disaccharides (e.g., sucrose, lactose, etc.) or any combinations thereof.

Exemplary iron (II) complex of amino acids may include, but are not limited to, iron (II) complex of alanine, iron (II) complex of arginine, iron (II) complex of asparagine, iron (II) complex of aspartic acid, iron (II) complex of cysteine, iron (II) complex of glutamine, iron (II) complex of glutamic acid, iron (II) complex of glycine, iron (II) complex of histidine, iron (II) complex of isoleucine, iron (II) complex of leucine, iron (II) complex of lysine, iron (II) complex of methionine, iron (II) complex of phenylalanine, iron (II) complex of proline, iron (II) complex of serine, iron (II) complex of threonine, iron (II) complex of tryptophan, iron (II) complex of tyrosine, iron (II) complex of valine, iron (II) complex of selenocysteine and iron (II) complex of pyrrolysine. In some embodiments, the iron (II) complex is not ferrous sulfate and tyrosine to form in-vivo ferrous-tyrosine complex. In some embodiments, the iron (II) complex is not ferrous sulfate and L-DOPA to form in-vivo ferrous-L-DOPA complex. In some embodiments, the iron (II) complex is not ferrous sulfate and L-phenylalanine to form in-vivo ferrous-L-phenylalanine complex. In some embodiments, the iron (II) complex is not ferrous sulfate and quinic acid to form in-vivo ferrous-quinate complex.

Exemplary iron (III) complex of amino acids may include, but are not limited to, iron (III) complex of alanine, iron (III) complex of arginine, iron (III) complex of asparagine, iron (III) complex of aspartic acid, iron (III) complex of cysteine, iron (III) complex of glutamine, iron (III) complex of glutamic acid, iron (III) complex of glycine, iron (III) complex of histidine, iron (III) complex of isoleucine, iron (III) complex of leucine, iron (III) complex of lysine, iron (III) complex of methionine, iron (III) complex of phenylalanine, iron (III) complex of proline, iron (III) complex of serine, iron (III) complex of threonine, iron (III) complex of tryptophan, iron (III) complex of tyrosine, iron (III) complex of valine, iron (III) complex of selenocysteine, and iron (III) complex of pyrrolysine. Although in some embodiments, the disclosed iron (II)/amino acid complexes, or iron (III)/amino acid complexes of the present disclosure comprise L-isoform of the amino acid moieties, D-isoform amino acid moieties, or a combination of both D- and L-isoforms.

In some embodiments, the metal-chelated peptides disclosed herein may be, or may include, metal-chelated oligopeptides which include two or more amino acids linked in a chain, where the carboxylic acid group of one amino acid and the amino group of another amino acid together form a peptide (—OC—NH—) bond. In some embodiments, the metal-chelated oligopeptides disclosed herein may comprise from two amino acids to twenty amino acids. In certain embodiments, the metal-chelated oligopeptides may include, but are not limited to metal-chelated dipeptides, metal-chelated tripeptides, metal-chelated tetrapeptides, metal-chelated pentapeptides, metal-chelated hexapeptides, metal-chelated heptapeptides, metal-chelated octapeptides, metal-chelated nonapeptides, metal-chelated decapeptides, or any combinations thereof. In particular disclosed embodiments, the iron (II)-chelated oligopeptides may include, or may be, iron (II)-chelated dipeptides, iron (II)-chelated tripeptides, iron (II)-chelated tetrapeptides, iron (II)-chelated pentapeptides, iron (II)-chelated hexapeptides, iron (II)-chelated heptapeptides, iron (II)-chelated octapeptides, or any combinations thereof. Exemplary iron (II)-chelated peptides may include, but are not limited to, iron (II)-chelated Gly-Gly, Gly-Leu, iron (II)-chelated Ala-Phe, iron (II)-chelated Phe-Ile-Val, iron (II)-chelated Leu-Pro-Trp, iron (II)-chelated Pro-Leu-Gly, iron (II)-chelated Gly-Gly-Gly, iron (II)-chelated Gly-Lys-Val-Ser, iron (II)-chelated Met-Thr-Cys-Gln, iron (II)-chelated Lys-Gly-Arg-Trp-Phe, iron (II)-chelated Ala-Leu-Pro-Gly-Ala, iron (II)-chelated Gly-Phe-Arg-His-Gly-Gly, iron (II)-chelated Ala-Phe-Phe-Ile-Val-Gly-Gly, iron (II)-chelated Gly-Lys-Val-Ser-Pro-Leu-Gly-Pro.

In particular disclosed embodiments, the iron (III)-chelated oligopeptides may include, or may be, iron (III)-chelated dipeptides, iron (III)-chelated tripeptides, iron (III)-chelated tetrapeptides, iron (III)-chelated pentapeptides, iron (III)-chelated hexapeptides, iron (III)-chelated heptapeptides, iron (III)-chelated octapeptides, or any combinations thereof. Exemplary iron (III)-chelated peptides may include, but are not limited to, iron (III)-chelated Gly-Gly, Gly-Leu, iron (III)-chelated Ala-Phe, iron (III)-chelated Phe-Ile-Val, iron (III)-chelated Leu-Pro-Trp, iron (III)-chelated Pro-Leu-Gly, iron (III)-chelated Gly-Gly-Gly, iron (III)-chelated Gly-Lys-Val-Ser, iron (III)-chelated Met-Thr-Cys-Gln, iron (III)-chelated Lys-Gly-Arg-Trp-Phe, iron (III)-chelated Ala-Leu-Pro-Gly-Ala, iron (III)-chelated Gly-Phe-Arg-His-Gly-Gly, iron (III)-chelated Ala-Phe-Phe-Ile-Val-Gly-Gly, iron (III)-chelated Gly-Lys-Val-Ser-Pro-Leu-Gly-Pro.

The disclosed combination and/or composition may comprise a sufficient amount of metal chelate such that administration of the combination and/or composition to an animal provides the animal with a desired amount of metal chelate. The desired amount of metal chelate may be any effective dose as understood by a person of ordinary skill in the art. For example, the desired amount of metal chelate an amount effective as a food supplement or an amount effective as a biocidal agent. By way of example, the metal chelate may be administered to an animal, such as a human or non-human animal, such that the animal ingests and/or absorbs a total amount of the metal chelate (or an equivalent number of moles of the metal chelate) from 1 mg to 200 g per kg of the average body weight of the animal, such as, 5 mg to 150 g, 10 mg to 100 g, 50 mg to 50 g, 100 mg to 10 g, 500 mg to 50 g, or 1 g to 5 g. Exemplary amount includes, but is not limited to, 1 mg, 2 mg, 3 mg, 4 mg, 5 mg, 10 mg, 50 mg, 100 mg, 500 mg, 1 g, 5 g, 10 g, 50 g, 100 g, 150 g, or 200 g per kg of the average body weight of the animal. Additionally, or alternatively, combination and/or composition comprising the metal chelate may be administered with feed in an amount sufficient to provide from 0.001 to 20 g of the metal chelate per kg of feed, such as 0.002 to 15 g/kg, or at least 0.002 g/kg, 0.005 g/kg, 0.01 g/kg, 0.02 g/kg, 0.05 g/kg, 0.1 g/kg, 0.5 g/kg, 1 g/kg, 2 g/kg, 5 g/kg, 10 g/kg, 15 g/kg of the feed.

5. Chromium Compound

In certain embodiments, the disclosed combination and/or composition may comprise, consist essentially of, or consist of the primary combination and/or composition and one or more chromium compounds. Chromium compounds that can be used in the compositions and/or combinations disclosed herein include any chromium compound suitable for feed, food, pharmaceutical or veterinary use. Without being bound to a particular theory, chromium may help facilitate glucose intake in cells, and therefore may provide a substantial benefit when used in combination with the primary combination and/or composition. In some embodiments, the chromium compound(s) comprise a chromium (III) compound. Exemplary chromium compounds include, but are not limited to, chromium organic acid compounds, such as chromium picolinate, chromium tripicolinate, chromium nicotinate, chromium polynicotinate, chromium acetate, or chromium propionate, or chromium amino acid compounds, such as chromium histidinate, chromium nicotinate-glycinate, chromium glycinate, chromium aspartate, chromium methionine, chromium trimethionine, or chromium phenylalanine; chromium halides, such as chromium chloride, chromium bromide, chromium iodine or chromium fluoride; chromium yeast; chromium carbonate; chromium nitrate; chromium sulfate; chromium phosphate; chromium nitrite; or a combination thereof. Additional information concerning chromium compounds can be found in U.S. Patent Publication No. 2010/0178362, which is incorporated herein by reference. The amount of chromium compound may be sufficient to provide a daily dose of from 0.001 milligram to 5000 milligrams of a total chromium compound per kilogram body weight, such as from 0.01 milligram total chromium compound to 1000 milligrams per kilogram body weight, from 0.1 milligram to 100 milligrams per kilogram body weight, from 0.5 milligram to 25 milligrams per kilogram body weight, or from 1 milligram to 10 milligrams per kilogram body weight.

In some embodiments, the amount of chromium compound in the combination is selected to provide a sufficient amount of chromium to the subject. The sufficient amount of chromium may be from 0.5 µg per day to 10,000 µg per day or more, such as from 5 µg to 10,000 µg/day, from 25 µg to 10,000 µg per day, from 50 µg to 10,000 µg per day, from 100 µg to 10,000 µg per day, from 200 µg to 10,000 µg per day, from 300 µg to 10,000 µg per day, from 400 µg to 10,000 µg per day, from 500 µg to 10,000 µg per day, from 750 µg to 10,000 µg per day, from 1,000 µg to 10,000 µg per day, from 1500 µg to 10,000 µg per day, from 2,000 µg to 10,000 µg per day, from 2500 µg to 10,000 µg per day, from 3000 µg to 10,000 µg per day, from 3500 µg to 10,000 µg per day, from 4000 µg to 10,000 µg per day, from 4500 µg to 10,000 µg per day, from 5,000 µg to 10,000 µg per day, from 6000 µg to 10,000 µg per day, from 7000 µg to 10,000 µg per day, from 8000 µg to 10,000 µg per day, from 9000 µg to 10,000 µg per day or more chromium/day.

6. Other Components

Additionally, or alternatively, the combination and/or composition may comprise, in combination with the primary combination and/or composition, components such as, but not limited to, a copper species, vitamin, allicin, alliin, alliinase, yeast, polyphenol, preservative, antimicrobial, vaccine, growth promotant, growth factor, difructose anhydride III, or combinations thereof.

I. Copper Species

Disclosed compositions and/or combinations comprising the primary combination and/or composition may also be mixed with a copper species such as a copper species that provides a copper ion. The copper species may be a copper salt. Exemplary copper species include, but are not limited to, copper chloride, copper bromide, copper iodide, copper sulfate, copper sulfite, copper bisulfite, copper thiosulfate, copper phosphate, monobasic copper phosphate, dibasic copper phosphate, copper hypophosphite, copper dihydrogen pyrophosphate, copper tetraborate, copper borate, copper carbonate, copper bicarbonate, copper metasilicate, copper citrate, copper malate, copper methionate, copper succinate, copper lactate, copper formate, copper acetate, copper butyrate, copper propionate, copper benzoate, copper tartrate, copper ascorbate, copper gluconate, or a combination thereof, preferably copper sulfate, copper acetate, copper citrate, copper methionate, or a combination thereof. A copper species, such as a copper salt, may be provided separately, or individually, or it may be provided as part of a composition, such as a feed or a feed supplement.

II. Vitamins

Compositions and/or combinations comprising the primary combination and/or composition may also be used in combination with or administered as a composition with one or more additional vitamins. Exemplary vitamins include, but are not limited to, one or more of Vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (including folic acid), Vitamin B12 (various cobalamins; commonly cyanocobalamin in vitamin supplements), Vitamin C (ascorbic acid or a salt thereof, such as sodium ascorbate or calcium sorbate), Vitamin D (vitamin $D_1$, vitamin $D_2$, vitamin $D_3$, vitamin $D_4$, vitamin $D_5$, or combinations thereof), Vitamin E, Vitamin K (K1 and K2 (i.e. MK-4, MK-7)), and biotin, and derivatives, salts and/or analogs thereof. The vitamin(s) may be provided separately, or individually, or it may be provided as part of a composition, such as a feed or a feed supplement.

III. Allicin, Alliin and/or Alliinase

Additionally, or alterative, a combination and/or a composition comprising the primary combination and/or composition can be administered in combination with allicin, alliin, alliinase, or any combination thereof. Allicin (diallyl thiosulfate; 2-Propene-1-sulfinothioic acid S-2-propenyl ester) is a compound found in garlic, such as raw garlic.

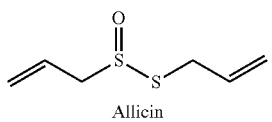
Allicin

When extracted, it may be an oily, yellowish liquid. Allicin may have medicinal and/or health benefits when consumed by animals. Benefits of allicin include, but are not limited to, an immunity booster; a blood thinner; an anti-oxidant; an anti-bacterial agent, such as against *E. coli*; an anti-inflammatory; an anti-viral; an anti-fungal; or may alleviate symptoms of bacterial, viral or fungal infections. Allicin is typically produced from alliin ((2R)-2-amino-3-[S]-prop-2-enylsulfinyl]propanoic acid) in damaged garlic cells by the action of the enzyme alliinase.

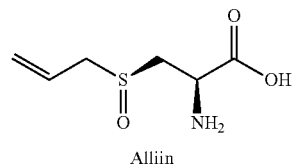
Alliin

When the garlic cells are damaged, such as by chopping, crushing, or cooking the garlic, the alliinase enzyme converts the alliin into allicin. Allicin, alliin, and/or alliinase may be provided as whole garlic cloves or bulbs; crushed, mashed, or chopped garlic; a garlic extract; and/or as a synthesized or isolated compound.

IV. Yeast

Additionally, or alternatively, a combination and/or composition comprising the primary combination and/or composition can be administered in combination with a microorganism, such as yeast. The yeast may be a yeast culture, a live yeast, a dead yeast, yeast extract, or a combination thereof. The yeast may be a baker's yeast, a brewer's yeast, a distiller's yeast, a probiotic yeast or a combination thereof. Exemplary yeast's include, but are not limited to, *Saccharomyces cerevisiae, Saccharomyces boulardii, Saccharomyces pastorianus, Brettanomyces bruxellensis, Brettanomyces anomalus, Brettanomyces custersianus, Brettanomyces naardenensis*, and *Brettanomyces nanus, Candida stellata, Schizosaccharomyces pombe, Torulaspora delbrueckii*, or *Zygosaccharomyces bailii*.

V. Polyphenols

In some embodiments, a combination and/or composition comprising the primary combination and/or composition may comprise an additive, such as, a polyphenol, that is useful for the prevention and inhibition of inflammatory processes, thereby improving animal gut health which, in turn, improves both animal health and performance. The polyphenol may be provided by a plant extract from a polyphenol-containing plant material. The plant material also may include non-polyphenol compounds, including polyphenol degradation products, such as gallic acid and trans-caftaric acid. Degradation can occur, for example, through oxidative and/or biological processes. Both the polyphenols and the non-polyphenol compounds may have biological activity. The plant extract may be prepared from a single plant material or from a combination of plant materials. Suitable plant materials from which a plant extract can be obtained include, but are not limited to, apples, blackberries, black chokeberries, black currants, black elderberries, blueberries, cherries, cranberries, grapes, green tea, hops, onions, quillaja, plums, pomegranates, raspberries, strawberries, and yucca.

In some embodiments, the plant extract is prepared from a pressed plant material, such as grape pomace, a dried plant material, such as tea, or a combination thereof. Pomace may be obtained substantially immediately post-pressing or as an ensiled product, i.e., pomace collected and stored for up to several months post-pressing. Suitable plants have a plurality of polyphenols and/or other non-polyphenolic compounds including, but not limited to, non-polyphenolic organic acids (such as gallic acid and/or trans-caftaric acid), flavanols, gallate esters, flavanodiols, phloroglucinol, pyrogallol, and catechol. In some embodiments, the plant extract is prepared from Pinot noir pomace, Pinot gris pomace, or green tea.

In some embodiments, pressed or dried plant material is ground to a fine powder prior to, or during, extraction. Pressed plant materials may be frozen to facilitate grinding. Polyphenols and other non-polyphenolic compounds may be extracted for administration. For example, polyphenols and other non-polyphenolic compounds may be extracted from the powder using a solution comprising a polar solvent, such as water, an alcohol, an ester, or a combination thereof. In some embodiments, the solution comprises a water-miscible alcohol, ester, or combination thereof, such as a lower alkyl alcohol, lower alkyl ester, or a combination thereof. In some embodiments, the solution is water or an aqueous solution comprising 25-99% solvent, such as 25-95% solvent, 30-80% solvent, or 50-75% solvent, and water. In certain embodiments, the solution is an aqueous solution comprising methanol, ethanol, isopropanol, ethyl acetate, or a combination thereof. The solution may be acidified by addition of an acid. The acid may prevent or minimize oxidative degradation of biologically-active polyphenols and other non-polyphenolic compounds in the extract. The acid may be any suitable acid, such as a mineral acid (e.g., hydrochloric acid), or an organic acid such as citric acid or acetic acid. In some embodiments, the solution comprises from 0.01% to 1% acid, such as 0.02-0.5%, 0.025-0.25%, or 0.05-0.15%. In some examples, the solution includes 0.1% hydrochloric acid.

Extraction may be performed at a temperature ranging from 0-100° C. In some embodiments, extraction is performed at a temperature ranging from 20-70° C., or at ambient temperature. Extraction may be performed for a duration ranging from several minutes to several days. To increase extraction efficiency, the plant material and solution may be mixed or agitated during extraction, such as by grinding the plant material during extraction, stirring the mixture, shaking the mixture, or homogenizing the mixture. In some embodiments, the extraction may be repeated one or more times with fresh solution to increase recovery of polyphenols and other non-polyphenolic compounds from the plant material. The liquid phases from each extraction cycle are then combined for further processing.

The liquid phase can be recovered, and the residual solids, or pulp, are discarded. Recovering the liquid phase may comprise decanting the liquid from the remaining solids and/or filtering the liquid phase to remove residual solids. The solvent (alcohol, ester, or combination thereof) can be removed from the liquid solution by any suitable means, such as evaporation (e.g., roto-evaporation), to produce an aqueous extract containing the biologically-active components in a mildly acidic solution.

In certain embodiments where the plant material includes a significant amount of oils, or lipids, an initial extraction of nonpolar components may be performed before extracting the polyphenols and other polar, non-polyphenolic compounds. Nonpolar components may be extracted by homogenizing the plant material in a nonpolar solvent, e.g., hexanes, heptanes, or a combination thereof. The solvent layer including the extracted nonpolar components is separated from the plant material and discarded.

The aqueous plant extract may be further purified by suitable means, e.g., extraction, chromatographic methods, distillation, etc., to remove non-polyphenolic compounds and/or to increase the concentration of polyphenols relative to other compounds in the extract.

The aqueous plant extract may be dried, for example by freeze-drying or other low-temperature drying methods, and ground to a powder to provide a dried plant extract. In some embodiments, the dried plant extract comprises 0.01 wt % to 25 wt % total polyphenols, such as 0.01 wt % to 10 wt %, 0.01 wt % to 5 wt %, 0.01 wt % to 2.5 wt %, 0.01 wt % to 1 wt %, 0.01 wt % to 0.5 wt %, 0.02 to 0.25 wt %, or 0.03-0.1 wt % total polyphenols. In certain embodiments, the dried plant extract further comprises non-polyphenolic compounds. For example, the dried plant extract may comprise 0.01-1 mg/g gallic acid, such as 0.05-0.5 mg/g or 0.09-0.25 mg/g gallic acid, and/or 0.001-0.1 mg/g trans-caftaric acid, such as 0.005-0.05 mg/g or 0.01-0.025 mg/g trans-caftaric acid.

The aqueous plant extract may be concentrated to a smaller volume, e.g., by evaporation, and used as an aqueous plant extract. In other embodiments, the aqueous plant extract is mixed with a carrier before drying and grinding. Suitable carriers include, for example, diatomaceous earth, silica, maltodextrin, ground grain (e.g., corn), meals (e.g., soybean or cottonseed meal) by-products (e.g., distiller's dried grains, rice hulls, wheat mill run), clays (e.g., bentonite), and combination thereof. The plant extract may be combined with a carrier in a ratio ranging from 10:1 to 1:10 by weight, such as from 5:1 to 1:5. For example, the plant extract may be mixed with diatomaceous earth in a ratio of 3:1 by weight.

Additionally, or alternatively, the additional components may comprise corn, soybean meal, wheat, wheat fiber, barley, rye, rice hulls, canola, limestone, salt, distillers dried grains with solubles (DDGS), dicalcium phosphate, sodium sesquicarbonate, methionine source, lysine source, L-threonine, biotin, folic acid, kelp, menadione dimethylpyrimidinol bisulfite, calcium aluminosilicate, or any combination thereof.

Additional information concerning feed supplement and/or additional components can be found in PCT application No. PCT/US2015/053439, and U.S. application Ser. Nos. 15/359,342, 14/699,740, 14/606,862, and 62/449,959 each of which is incorporated herein by reference in its entirety.

VI. Preservatives

The preservative may be benzoic acid or a salt thereof, e.g. sodium benzoate; lactic acid or a salt thereof, e.g. sodium lactate, potassium lactate or calcium lactate; propionic acid or a salt thereof, e.g. sodium propionate; ascorbic acid or a salt thereof, e.g. sodium ascorbate; gallic acid or a salt thereof e.g. sodium gallate; sulfur dioxide and/or sulfites; nitrites; nitrates; choline, or a salt thereof, such as an anion salt of choline, e.g. choline halide, such as chloride, bromide, iodide, fluoride, or choline hydroxide; or any combination thereof.

Additionally, or alternatively, compositions and/or combinations comprising the primary combination and/or composition may further comprise sorbic acid or a salt thereof. Sorbic acid, or a salt thereof, may act as a preservative, such as by inhibiting mold and/or yeast growth. The salt may be any suitable salt of sorbic acid, and in some embodiments, is a group I, group II, or organic salt of sorbic acid. Suitable salts include, but are not limited to, potassium sorbate, sodium sorbate, or ammonium sorbate.

VII. Antimicrobial

Disclosed compositions and/or combinations comprising the primary combination and/or composition may, additionally or alternatively, comprise an antimicrobial. The antimicrobial may be an antibiotic, an antifungal, an antiparasitic, an antiviral, or a combination thereof. An antibiotic may be a tetracycline, a penicillin, a cephalosporin, a polyether antibiotic, a glycopeptide, an orthosomycin, or a combination thereof. The antibiotic may be selected from, by way of example, and without limitation, virginiamycin, Bacitracin MD, Zinc Bacitracin, Tylosin, Lincomycin, Flavomycin, bambermycins, Terramycin, Neo-Terramycin, florfenicol, oxolinic acid, oxytetracycline, hydrogen peroxide (Perox-Aid® 35%), bronopol (2-bromo-2-nitro-1,3-propanediol, Pyceze®), sulfadimethozine, ormetoprim, Sulfadiazine, Trimethoprim, or a combination thereof. In some embodiments, the antibiotic is not, or does not comprise, hydrogen peroxide. In some embodiments, the antibiotic is virginiamycin, Bacitracin MD, Zinc Bacitracin, Tylosin, Lincomycin, Flavomycin, bambermycins, Terramycin, Neo-Terramycin, florfenicol, oxolinic acid, oxytetracycline, bronopol (2-bromo-2-nitro-1,3-propanediol, Pyceze®), sulfadimethozine, ormetoprim, Sulfadiazine, Trimethoprim, or a combination thereof.

An antifungal may be selected from, by way of example, formalin, formalin-F, bronopol (2-bromo-2-nitro-1,3-propanediol, Pyceze®), or a combination thereof. Exemplary antiparasitics may be selected from an anticoccidal, copper sulfate, fenbendazole, formalin, formalin-F, hyposalinity, hadaclean A, praziquantel, emamectin benzoate (SLICE®), or a combination thereof.

Suitable anticoccidial agents include, but are not limited to, ionophores and chemical anticoccidial products. Ionophores can include, but are not limited to, Monensin, Salinomycin, Lasalocid, Narasin, Maduramicin, Semduramicin, or combinations thereof.

Chemical anticoccidial products can include, but are not limited to, Nicarbazin, Maxiban, Diclazuril, Toltrazuril, Robenidine, Stenorol, Clopidol, Decoquinate, DOT (zoalene), Amprolium, or combinations thereof.

The disclosed combination and/or composition may be administered in an amount sufficient to provide a desired amount of the antimicrobial. The desired amount may depend on the particular antimicrobial or antibiotic used as will be understood by a person of ordinary skill in the art. In some embodiments, the amount of the antibiotic or antimicrobial that is used can be a therapeutically effective amount that is at an approved or authorized dosage level for a particular antibiotic. In some embodiments, the amount of antibiotic or antimicrobial administered in the combination and/or composition can range from greater than 0 ppm to 100,000 ppm, such as 0.25 ppm to 5,000 ppm, or 0.5 ppm to 2,500 ppm, or 0.75 ppm to 2,000 ppm, or 1 ppm to 1,500 ppm, or 5 ppm to 1,000 ppm, or 10 ppm to 500 ppm, or 25 ppm to 300 ppm. In yet additional embodiments, the amount of antibiotic or antimicrobial used can range from greater than 0 mg/kg of body weight to 100,000 mg/kg of body weight, such as 0.5 mg/kg to 2,500 mg/kg, or 1 mg/kg to 1,500 mg/kg, or 5 mg/kg to 1,000 mg/kg, or 10 mg/kg to 500 mg/kg m, or 25 mg/kg to 300 mg/kg, or 10-20 mg/kg.

In some embodiments, the amount of the antimicrobial or antibiotic that is included in the combination and/or composition can range from at least 1 g/ton of feed to 230 g/ton of feed (or at least 1.1 ppm to 256 ppm), such as at least 1 g/ton of feed to 220 g/ton of feed (or at least 1.1 ppm to 243 ppm), at least 1 g/ton of feed to 100 g/ton of feed (or at least 1.1 ppm to 110 ppm), at least 1 g/ton of feed to 50 g/ton of feed (or at least 1.1 ppm to 55 ppm), or at least 1 g/ton of feed to 10 g/ton of feed (or at least 1.1 ppm to 11 ppm). Particular antimicrobials or antibiotics that can be used, and dosage amounts of such antimicrobials and antibiotics include, but are not limited to, the following: Virginiamycin in an amount ranging from 5 g/ton of feed to 25 g/ton of feed (or 5 ppm to 27 ppm, such as 22 ppm); Bacitracin MD in an amount ranging from 40 g/ton of feed to 220 g/ton of feed (or 44 ppm to 242 ppm, or 50 ppm to 250 ppm in some other embodiments); Zinc Bacitracin in an amount ranging from 40 g/ton of feed to 220 g/ton of feed (or 44 ppm to 242 ppm); Tylosin in an amount ranging from 1 g/ton of feed to 1000 g/ton of feed (or 1 ppm to 1100 ppm); Lincomycin in an amount ranging from 1 g/ton of feed to 5 g/ton of feed (or 1 ppm to 6 ppm); Flavomycin in an amount ranging from 1 g/ton of feed to 5 g/ton of feed (or 1 ppm to 6 ppm); or combinations thereof.

The amount of an anticoccidial agent, as will be understood by a person of ordinary skill in the art (e.g., a veterinarian), can be selected depending on the particular anticoccidial agent used. In some embodiments, the amount of anticoccidial agent administered as part of the disclosed combination and/or composition may be a therapeutically effective amount for a particular animal species. In some embodiments, the amount of anticoccidial agent used can range from greater than 0 ppm to 100,000 ppm, such as 0.25 ppm to 5,000 ppm, or 0.5 ppm to 2,500 ppm, or 0.75 ppm to 2,000 ppm, or 1 ppm to 1,500 ppm, or 5 ppm to 1,000 ppm, or 10 ppm to 500 ppm, or 25 ppm to 300 ppm. In yet additional embodiments, the amount of antibiotic or antimicrobial used can range from greater than 0 mg/kg of body weight to 100,000 mg/kg of body weight, such as 0.5 mg/kg to 2,500 mg/kg, or 1 mg/kg to 1,500 mg/kg, or 5 mg/kg to 1,000 mg/kg, or 10 mg/kg to 500 mg/kg m, or 25 mg/kg to 300 mg/kg, or 10-20 mg/kg.

VIII. Vaccines

Disclosed compositions and/or combinations comprising the primary combination and/or composition may, additionally or alternatively, comprise a vaccine. Suitable vaccines can be selected from live coccidiosis vaccines, such as COCCIVAC (e.g., a composition comprising live oocysts of *Eimeria acervulina, Eimeria mivati, Eimeria maxima, Eimeria mitis, Eimeria tenella, Eimeria necatrix, Eimeria praecox, Eimeria brunetti, Eimeria hagani*, or combinations thereof), LivaCox (a composition comprising 300-500 live sporulated oocysts of each attenuated line of *Eimeria acervulina, E. maxima* and *E. tenella* in a 1% w/v aqueous solution of Chloramine B); ParaCox (a composition comprising live sporulated oocysts derived from *E. acervulina* HP, *E. brunetti* HP, *E. maxima* CP, *E. maxima* MFP, *E. mitis* HP, *E. necatrix* HP, *E. praecox* HP, *E. tenella* HP, and combinations thereof); Hatch Pack Cocci III (a composition comprising oocysts derived from *Eimeria acervulina, Eimeria maxima, Eimeria tenella*, or combinations thereof); INOVOCOX (a composition comprising oocysts derived from *Eimeria acervulina, Eimeria maxima, Eimeria tenella*, and a sodium chloride solution); IMMUCOX (a composition comprising live oocysts derived from *Eimeria acervulina, Eimeria maxima, Eimeria necatrix, Eimeria tenella*, and combinations thereof), Advent, or combinations thereof. Vaccines may also comprise live oocysts of the *Eimeria* genus, for example, *Eimeria aurati, Eimeria baueri, Eimeria lepidosirenis, Eimeria leucisci, Eimeria rutile, Eimeria carpelli, Eimeria subepithelialis, Eimeria funduli* and/or *Eimeria vanasi*. Vaccines may also comprise oocysts from the genus *Epeimeria*, a new genus of coccidia infecting fishes.

Other suitable vaccines include, but are not limited to, ALPHA DIP® 2000, ALPHA DIP® *Vibrio*, ALPHA MARINE® *Vibrio*, ALPHA DIP® ERM Salar, ALPHA JECT Micro® 1 ILA, ALPHA JECT Micro® 7ILA, ALPHA JECT® Panga, ALPHA JECT® 1000, ALHPA JECT® 2000, ALPHA JECT® 3000, ALPHA JECT® 3-3, ALPHA JECT® 4000, ALPHA JECT® 4-1, ALPHA JECT® 5-1, ALPHA JECT® 5-3, ALPHA JECT® 6-2, ALPHA JECT® micro 1 ISA, ALPHA JECT® micro 2, ALPHA JECT® micro 4, Apex®-IHN, AQUAVAC® ERM Oral, AQUAVAC® ERM immersion, AQUAVAC® FNM Injectable, AQUAVAC® IPN Oral, AQUAVAC® RELERA™, AQUAVAC® *Vibrio* Oral, AQUAVAC® *Vibrio Pasteurella* injection, AQUAVAC® *Vibrio* immersion and injectable, AQUAVAC-COL™ immersion, AQUAVAC-ESC™ immersion, Birnagen Forte 2, Ermogen, Forte Micro, Forte V II, Forte V1, Fry Vacc 1, Furogen Dip, ICTHIOVAC JG injection, ICTHIOVAC® PD immersion, Lipogen DUO, Lipogen Forte, Microvib, Norvax® Compact PD injection, Norvax® Minova 4WD, Norvax® Minova 6 injection, Norvax® STREP Si immersion and injection, Premium Forte Plus, Premium Forte Plus ILA, Renogen, Vibrogen 2, or a combination thereof.

IX. Growth Promotants

Disclosed compositions and/or combinations comprising the primary combination and/or composition may, additionally or alternatively, further comprise a growth promotant that can, for example, help increase the efficiency of animal production, such as by increasing the rate of weight gain, improved feed efficiency and/or product output. A growth promotant may also increase the quality of a product, such as increase the quality of meat produced. Growth promotants can include, but are not limited to, β-agonists, antibiotics, antimicrobials, steroids and hormones. In some embodiments, a growth promotant may be a compound that has one or more other uses and is used as a growth promotant at a lower dose than the dose for the primary application. For example, an antibiotic or antimicrobial compound may also be useful as a growth promotant when used at a subtherapeutic dose. Exemplary growth promotants include, but are not limited to, β-agonists such as ractopamine and zilpaterol; somatotropin such as bovine somatotropin (bST) and recombinant bovine somatotropin (rbST); ionophores such as monesin, lasalocid, laidlomycin, salinomycin and narasin; hormones such as oestrogen, progesterone, testosterone and analogs thereof, estradiol benzoate; tetracyclines, such as oxytetracycline, chlortetracycline, tetracycline, demeclocycline, doxycycline, lymecycline, meclocycline, methacycline, minocycline, rolitetracycline, and salts thereof, for example, hydrochloride, hydrobromide, hydroiodide, calcium, sodium, potassium, magnesium, or lithium salts; arsanilic acid; 4-hydroxy-3-nitrobenzenearsonic acid, erythromycin thiocyanate, tylosin phosphate, melengestrol acetate, iodinated casein, ethopabate, oleandomycin, penicillin G procaine, chlortetracycline, sulfathiazole, bambermycins, bacitracin, virginiamycin, chlortetracycline calcium complex, or salt and/or combinations thereof.

X. Growth Factors

Growth factors belong to a complex family of biological compounds, such as peptide hormones, that include transforming growth factors, insulin-like growth factors, epithelial growth factors, and placental growth factors. Growth factors may be useful for therapeutic applications and/or as feed supplements.

Insulin-like growth factors (IGFs) are polypeptides that have a high sequence similarity to insulin. IGFs are part of a system that enables cells to communicate with their environment. IGFs are useful for regulation of normal physiology and have a role in cell proliferation and inhibition of cell death. IGFs can be obtained from biological sources, such as milk or blood, by methods known to persons of ordinary skill in the art. The methods include adding anti-coagulants to whole blood, centrifuging and separating the plasma. Alternatively, IGFs can be extracted from milk, such as by chromatography, including cation exchange chromatography, as described in European patent No. EP 0 313 515, incorporated herein by reference. IGF also can be produced by recombinant techniques, such as by using yeast, as in the methods described in U.S. Pat. Nos. 6,117,983, 7,071,313 and 7,193,042, or bacteria, as described in U.S. Pat. Nos. 5,084,384, 5,489,517, and 5,958,754, all of which are incorporated herein by reference.

Insulin-like growth factor-1 (IGF-1 or IGF-I) is typically secreted by the liver and is important for achieving maximal growth, such as childhood growth, but also continues to have an effect in adults. Insulin-like growth factor-2 (IGF-2 or IGF-II) is thought to be a major growth factor for fetal growth and early development. As such, it is typically important during gestation.

Transforming growth factors (TGFs), such as transforming growth factor beta (TGF-beta), are polypeptides that are important for several functions within a cell, such as proliferation and cellular differentiation. They also may have a role in immunity and wound healing.

Although growth factors, such as IGFs and TGFs often are obtained from animal sources, such as milk or blood, they are usually bound to a binding protein that causes the IGF to be inactive. An IGF bound to a binding protein is referred to as an inactive IGF. For example, it is estimated that more than 99% of IGF-1 in plasma is bound to a binding protein. To form an active IGF, the binding protein is separated from the IGF polypeptide. During activation, the amount of IGF typically remains the same, but the ratio of active IGF to inactive IGF increases. Methods to form active IGF from inactive IGF are known in the art. For example, methods for increasing the ratio of active IGF to inactive IGF include processes routinely used to activate functional proteins obtained from a biological material. Such processes include, but are not limited to, exposing the biological material to heat shock, temperature adjustment, alcohol extraction, pH adjustment, enzyme addition, ionic changes, other chemical additions, and pressure, or combinations thereof. Without being bound to a particular theory, such methods typically cause the dissociation of the binding protein from the IGF protein. Also, methods for measuring the concentration of active IGF are known to persons of ordinary skill in the art. For example, suitable assays are commercially available, including solid phase sandwich ELISA assays that specifically measure IGF that is not bound to a binding protein (e.g., R&D Systems, catalog number DFG100). Additional information concerning growth factors can be found in international publication No. WO 2020/142305, which is incorporated herein by reference in its entirety.

XI. Additional Components

Disclosed embodiments of a combination and/or composition comprising the primary combination and/or composition may further comprise one or more additional components. Additional components may be used for any desired purpose, such as a substantially biologically inert material added, for example, as a filler, or to provide a desired beneficial effect. For example, the combination and/or composition may include a carbonate (including a metal carbonate such as calcium carbonate); a trace mineral, such as, but not limited to, chloride, fluoride, iodide, chromium, copper, zinc, iron, magnesium, manganese, molybdenum, phosphorus, potassium, sodium, sulfur, selenium, or a combination thereof, a bulking agent; a micro tracer, such as iron particles coated with a dye; algae; a carrier; a colorant; a taste enhancer; an oil, such as mineral oil, corn oil, soybean oil, or a combination thereof, lycopene; astaxanthin; cryptoxanthin; beta-carotene; lutein; zeaxanthin; canthaxanthin; vitamin E; ascorbic acid; Vitamin D; Vitamin B2; Biotin; Vitamin B6; Niacin; Pantothenic Acid; Folic Acid; or any combination thereof.

In some embodiments, the combination and/or composition does not comprise such additional components. In other embodiments, the combination and/or composition comprises from greater than zero to 40% or more by weight additional components, such as from 0.1% to 40% by weight, or from 0.2% to 35% by weight additional components. In certain embodiments, the combination and/or composition comprises from 0.1% to 5% by weight additional components, such as from 0.2% to 3% by weight. In other embodiments, the combination and/or composition comprises from 5% to 20% by weight additional components, such as from 10% to 15% by weight. And in further embodiments, the combination and/or composition comprises from 20% to 40% by weight additional components, such as from 30% to 35% by weight additional components.

Such additional components typically do not materially affect the basic and novel characteristics of the disclosed combination and/or composition and/or the beneficial results obtained by administration of the same.

V. Method of Use

The primary combination and/or composition may be administered to an animal, for example, a ruminant, such as a bovine. In some embodiments, the ruminant, such as a bovine, may be in transition or may be a lactating ruminant. And in some embodiments, the primary combination and/or composition is administered to improve a milk yield in the ruminant, for example, increasing milk yield in dairy cows.

The primary combination and/or composition may be administered prior to calving, such as throughout the dry period, and/or from 65 days prior to calving, 60 days, 56 days, 45 days, 30 days, 28 days, or 21 days prior to calving, and may be administered up to calving, or through calving to 150 days or more post calving, such as 100 days, 75 days, 50 days, 42 days, 35 days, 28 days, 21 days, 14 days, or 7 days post calving.

In some embodiments, the primary combination and/or composition is administered in combination with an additional calcium source such that the minimum dietary level of calcium administered to the animal including the primary combination and/or composition is 1.6% or 180 g/head. The additional calcium source may be administered in an amount sufficient to raise the level of dietary calcium to 1.6% including any calcium provided by the primary combination and/or composition. Suitable calcium sources include, but are not limited to, any calcium sources suitable for administration to bovines, such as calcium carbonate, bone ash, bone meal, calcite, limestone, calcium gluconate, calcium hydroxide, calcium sulfate, calcium chloride, calcium butyrate, chalk, clam shells, oyster shells, dolemite, calcium chelates, monocalcium phosphate, dicalcium phosphate, calcium propionate, or any combination thereof.

Administering the primary combination and/or composition may improve milk yield in the ruminant, such as in a dairy cow. In some embodiments, administering the primary combination and/or composition to a ruminant during the period before calving results in an increase in milk yield post calving, compared the milk yield of an animal that is not administered the primary combination and/or composition during the same period. The increase in milk yield may be determined during the first 4 weeks after calving.

In some embodiments, the milk yield of cows that are administered the disclosed combination and/or composition, as determined during the first four weeks post calving, is at least 20% higher, such as 20% to 30% or 20% to 27% higher, than the milk yield of cows that are not administered either the anionic dietary supplement, the 25-hydroxy vitamin D, or a combination thereof. Additionally, the milk yield of cows that are administered the disclosed combination and/or composition is at least 5% higher, such as from 5% to 15%, or from 5% to 10% higher, than the milk yield of cows that are administered the anionic dietary supplement but not 25-hydroxy vitamin D. Furthermore, administration of 25-hydroxy vitamin D pre- or post-calving is understood to have no effect on milk yield. See, for example, Guo, et al., "Effect of dietary vitamin $D_3$ and 25-hydroxy vitamin $D_3$ supplementation on plasma and milk 25-hydroxy vitamin $D_3$ concentration in dairy cows," Journal of Dairy Science (2018), vol. 101, pages 3545-3553, which states that no effect on milk yield was observed with 25-hydrocyvitamin $D_3$ supplementation.

In other embodiments, administering the primary combination and/or composition throughout the transition period results in an improved milk yield, compared to the milk yield of an animal that is not administered the primary combination and/or composition during the transition period.

Additionally, or alternatively, administering the primary combination and/or composition may result in a urine pH level of below 6, such as from pH 5 or lower to below 6, or from pH 5.5 to below 6.

Administering the primary combination and/or composition also may improve serum calcium levels, compared to cows that are not administered the combination and/or composition. Additionally or alternatively, administration of the primary combination and/or composition may prevent or substantially reduce periparturient hypocalcemia and/or incidents of metritis, retained placenta, and/or other infectious and/or metabolic diseases, for example, postpartum metabolic diseases. And/or in some embodiments, administering the primary combination and/or composition to an animal, such as a bovine, improves the immune function of the animal, compared to an animal that is not administered the primary combination and/or composition. The immune function improvement may be identified by an improvement in one or more immune markers, such as, but not limited to, IL-6.

The primary combination and/or composition may be administered in any form or formulation suitable for administration to an animal. In some embodiments, the primary combination and/or composition is a composition comprising the first composition and the second composition. In some embodiments, the first and second compositions are both solid compositions, and the primary combination and/or composition is an admixture of the first and second compositions, optionally with one or more additional components, and optionally with a solid feed.

In some embodiments, the second composition is mixed with a suitable carrier, such as an oil, for example, a mineral oil, and applied to the first composition to form the primary combination and/or composition. For example, the second composition/carrier mixture may be sprayed onto particles of the first composition, or mixed with such particles, such that the second composition forms a layer that covers at least part of the surface of the first composition particle. In some embodiments, such a coated composition that also comprises a carrier, such as a mineral oil, may improve the shelf life of the primary combination and/or composition compared to an embodiment of the primary combination and/or composition where the first and second compositions are intimately mixed without a carrier. In other embodiments, the second composition is formulated as a emulsion. The emulsion form of the second composition may be mixed with the first composition in a manner similar to embodiments comprising a carrier to form the primary combination and/or composition. In any embodiments, the primary combination and/or composition comprising the carrier and/or the emulsion form of the second composition may have a shelf file of 6 months or more, whereas an embodiment without a carrier or an emulsion form of the second composition, may have a shelf life of less than 6 months. Additionally, or alternatively, the primary combination and/or composition comprising the carrier and/or the emulsion form of the second composition may demonstrate reduced segregation of components, compared to an embodiment without a carrier or an emulsion form of the second composition. The shelf life may be determined by monitoring degradation of the second composition when in the presence of the first composition.

In other embodiments, the primary combination and/or composition is administered as a combination comprising separate administration of the first and second compositions, although the separate administration may be sequential in any order or substantially simultaneous. In certain embodiments, the second composition may be administered in a liquid form by any suitable route, such as orally or by injection. The first composition typically is a solid and may be administered orally, optionally as a mixture with a solid feed.

A. Animals

Embodiments of the disclosed combination and/or composition are administered, for example, fed, to an animal, such as a human or non-human animal. The non-human animal may be a land animal, such as a mammal, and in some embodiments, the animal is a ruminant. The non-human animal can be an animal raised for human consumption or a domesticated animal. Examples of animals that can be fed and/or otherwise administered the disclosed combination include, but are not limited to, ruminant species, such as a sheep, goat, bovine (such as a cow, bull, steer, heifer, calf, bison, or buffalo), deer, bison, buffalo, elk, alpaca, camel or llama. In certain embodiments, the combination and/or composition is fed to a bovine, and may be fed to a dairy cow.

VI. Other Compositions

Also disclosed are the following combinations.

A combination comprising 25-hydroxy vitamin D, such as Hy-D®, and a composition comprising dried, extracted glutamic acid fermentation product, corn fermentation solubles, and grain byproducts, (available as Anion Booster®).

A combination comprising 25-hydroxy vitamin D, such as Hy-D®, and a composition comprising extracted glutamic acid fermentation product, corn fermentation solubles, magnesium chloride, processed grain byproducts (available as Bio-Chlor®)

A combination comprising 25-hydroxy vitamin D, such as Hy-D®, and a composition comprising magnesium sulfate, ammonium chloride, hydrochloric acid, and plant protein products (available as MegAnion®)

A combination comprising 25-hydroxy vitamin D, such as Hy-D®, and a composition comprising magnesium chloride, calcium chloride, calcium carbonate, magnesium oxide, grain byproducts, roughage products, plant protein products (available as Soychlor®)

A combination comprising 25-hydroxy vitamin D, such as Hy-D®, and a composition comprising magnesium sulfate, ammonium chloride, hydrochloric acid and processed grain byproducts (available as Ultrachlor)

A combination comprising 25-hydroxy vitamin D, such as Hy-D®, and a composition comprising dried Condensed Molasses Fermentation Soluble (available as Real Close)

VII. EXAMPLES

Example 1

Effect of Vitamin D Source on Serum Calcium and Production in Transition Cows Fed a Positive or Negative DCAD Diet The objective of this study was to investigate the potential synergistic effects of Animate® and Hy-D® for improving peripartum sera calcium concentrations, DMI and milk production in transition dairy cows.

Fifteen far off dry cows blocked by Parity, Breed, and ME Milk (5 cows/treatment (3 Holstein, 2 Jersey)) were fed 4.4 pounds of the pelleted dry cow supplement to get them familiar with the feed as they would need to eat it during the close-up period. They were also trained to the Insentec System to eat Ad-libitum hay.

Measurements made during the study included: Pre-Partum dry matter intake (DMI) (−28 days to calving); Post-Partum DMI (Week 1-Week 4); body weight (BW) at dry-off, −28, −14, +7, +14, +28, +35, +42 days; and body condition score (BCS) at dry-off, −28, −14, +7, +14, +28 days; milk components—fat, protein, somatic cell count (SCC) (3 times/week for weeks 1 and 2); milk yield—daily and weekly (weeks 1 to 4); health events—mastitis, ketosis, metritis, milk fever (MF), displaced abomasum (DA), and retained fetal membrane (RFM) through 28 days in milk (DIM).

Additionally, physiological and metabolic measurements included urine pH during prepartum period day −28 to calving (2 consecutive days/week) with a target pH of 5.5-6.0. Blood serum samples were obtained on the following days: dry off (−60), −45, −28, −14, −7, +1.5 (36 hours), +2 (48 hours), and +3 (72 hours) to be analyzed for serum calcium, phosphorus, magnesium, sodium, potassium, and chloride.

The close up treatment groups included:

Group C (Control)—individual feeding of 4.4 pounds of the dry cow ration in pellet form and 4.4 pounds of ground corn, and a total of 80,000 IU of vitamin D3;

Group D—(Control diet plus vitamin D3) the control diet from group C with the addition of 0.93 pounds of Animate® and 80,000 IU Vitamin D3;

Group H (Control diet plus Animate® and Hy-D®) the control diet from group C with the addition of 0.93 pounds of Animate® and 80,000 IU of 25-hydroxy vitamin D3, administered as the commercial product Hy-D® (DSM Nutritional Products)

Cows were allowed to eat ad-libitum Coastal Bermudagrass hay measured individually though the Smart-Feed system.

Statistical analysis of the trial was done using the mixed procedure of SAS 9.4 with fixed effects of treatment, time, and treatment×time, with breed as a covariate and time as a repeated measure.

Results

Health Events: One animal from treatment group H developed mastitis and was removed from the trial postpartum, but all measurements to that time, including production measurements, were used in the study. No other animals showed clinical signs of metritis, DA, RFM, MF, ketosis or mastitis.

Prepartum: Hay intake did not differ (P=0.47) within treatment groups C, D or H (16.59, 17.91 and 15.64 pounds, respectively). Pre-partum urine pH was lower in groups D and H than for group C. This is to be expected as negative DCAD diets decrease the alkalinity of blood.

Cows in treatment groups D and H had higher (P=0.02) prepartum serum calcium and higher (P=0.02) urinary calcium urine excretion than those in treatment group C, indicating that the calcium flux or pool of available calcium to meet their needs were present when needed.

Postpartum: Total mixed ration (TMR) intake was significantly different (P=0.02) within treatment groups with cows in group C consuming more than cows in groups D or H (40.61, 36.59 and 38.19 pounds, respectively) and day and week were significant (P=0.001) increasing linearly each time period, as expected.

Postpartum serum calcium mg/dL tended (P=0.06) to be higher in treatment groups D and H (8.8 and 8.4) than group C (7.8) as expected by following the fully acidified Animate® program.

Milk yield was significantly different (P<0.0001) within treatment groups C, D, or H (66.22, 75.28 and 82.30 pounds, respectively) and different (P<0.0001) each day of lactation, increasing linearly. Milk fat percentage was significantly different (P=0.01) within treatment groups C, D, or H (5.87, 5.22 and 4.14% respectively). Milk protein percentage was significantly different (P=0.02) within treatment groups C, D, or H (4.17, 3.83, and 3.70 respectively).

Example 2

The effects of various DCAD diet supplements has been investigated. One such study had the following protocol.

The purpose of Project 1 is to determine the adequate level of DCAD mineral supplement to provide to the OSU dairy herd to achieve the proper physiological outcomes, namely a urine pH of 5.5. For this project 4 non-lactating pregnant late pregnant primi- and multiparous Holstein (n=2) and Jersey (n=2) cows are used. Each receives a DCAD supplement (5 pounds/day) beginning approximately 28 days prior to calving. The treatment supplement is hand fed once daily, top-dressed on each cow's individual TMR. Individual cow dry matter intake (DMI) is measured using SmartFeed Trailers (C-Lock Inc.). Following parturition health events and milk production are recorded through 28 DIM.

Parameter Measurements:

1. Prepartum dry matter intakes and orts: recorded on 3 consecutive days per week during the pre-partum period (−28 days to calving),
2. Postpartum dry matter intakes and orts: recorded on 3 consecutive days per week (DMI, week 1 through week 4) using the Insentec system.
3. Body weight (days relative to calving): dry-off, −28, −14, +7, +14, +28
4. Body condition score (days relative to calving): dry-off, −28, −14, +7, +14, +28
5. Milk components: fat, protein (3 times per week during week 1 and 2), sampled at each milking (AM & PM) to account for diurnal variation
6. Somatic cell counts: 2 consecutive test-days
7. Milk: daily, weekly average (weeks 1 to 4)
8. Health events (MF, DA, ketosis, mastitis, RFM, metritis) through 28 DIM Physiological and Metabolic Measurements:

1. Urine pH (relative to calving) sampling schedule.
    a. On −28 days to expected calving and then on 2 consecutive days per week. Target urine pH range 5.5 to 6.0. Adjust urine pH by adding or subtracting Animate® to the negative DCAD mineral supplement until cows remain in target pH range of 5.5 to 6.0.
2. Serum blood (days/times relative to calving) sampling schedule: −60 (dry-off), −45, −28, −14, −7, +1.5 (36 hours), +2 (48 hours), +3 (72 hours). Serum total calcium, phosphorus, serum NEFAs and BUNs are analyzed.

Example 3

Project 2: Transition Cow—Animate Supplementation Study

The purpose of this study is to determine the effect of an additional (Confidential) supplement in a negative DCAD diet in transition dairy cows on health and production in early lactation.

Fifteen non-lactating, late pregnant primi- and multiparous Holstein (n=10) and Jersey (n=5) cows are assigned to one of three treatments (5 cows/treatment) 28 days priorto predicted calving date. Treatments are blocked and balanced for parity, previous ME milk and predicted calving date. Cows remain on their respective treatment diets until they calve. Following parturition health events and milk production are recorded through 28 DIM.

Treatments Consist of:

1. Control (positive DCAD mineral supplement)
2. Treatment (negative DCAD mineral supplement No. 1)
3. Treatment (negative DCAD mineral supplement No. 2)

Feeding:

The treatment mineral supplements are fed as described for the experiment I (Example 2) above. Animals will be managed as described above as well.

Production Measurements:

1. Prepartum dry matter intakes and orts: recorded on 3 consecutive days per week during the pre-partum period (−28 days to calving).
2. Postpartum dry matter intakes and arts: recorded on 3 consecutive days per week (DMI, week 1 through week 4) using the Insentec system.
3. Body weight (days relative to calving): dry-off, −28, −14, +7, +14, +28, +35, +42,
4. Body condition score (days relative to calving): dry-off, −28, −14, +7, +14, +28
5. Milk components: fat, protein (3 times per week, during weeks 1 and 2) sampled at each milking (AM & PM)
6. Somatic cell counts: 2 consecutive test-days
7. Milk: daily, weekly average (weeks 1 to 4)
8. Health events (MF, DA, ketosis, mastitis, RFM, metritis) through 28 DIM Physiological and Metabolic Measurements:

1. Urine pH (relative to calving) sampling schedule.
    a. Negative D AD diet: on −28 days to expected calving and then on 2 consecutive days per week. Target urine pH range 5.5 to 6.0. Adjust urine pH by adding or subtracting Animate® to the negative DCAD mineral supplement until cows remain in target pH range of 5.5 to 6.0.

b. Positive DCAD diet: on −28 days to expected calving and then on 2 consecutive days per week.

B. Study Results

The effects of dietary vitamin D source on serum calcium (Ca), urinary Ca excretion and milk yield when fed in combination with a prepartum fully acidogenic negative DCAD diet. Non-lactating, pregnant multiparous cows (n=15), balanced for breed (Holstein n=9 and Jersey n=6) and previous ME milk, were assigned to 1 of 3 treatments (Trt, 5 cows/Trt), consisting of a control (CON, positive DCAD, 8.9 mEq/100 g DM) and two negative DCAD diets (−15.4 mEq/100 g DM), one with vitamin $D_3$ (D3), and one with 25-hydroxy vitamin $D_3$ (Hy-D®; DSM Nutritional Products). Pelleted trt were formulated to provide 36.37 KIU/d of vitamin $D_3$ and began 28 d prior to expected calving date. Cows were individually fed a mixture of the trt and 2 kg of ground corn daily at 0800 to assure intake. Negative DCAD trt were formulated to provide 0.46 kg/d of Animate® (Phibro Animal Health) and if needed additional Animate was top-dressed at each feeding to achieve a urine pH between 5.5-6.0. Close-up cows had ad-lib access to chopped Bermudagrass hay and DMI was measured using SmartFeed Pro systems (C-Lock Inc.). Urine and serum samples were collected weekly prepartum and serum was collected 36, 48, and 72 hr post-calving. Postpartum DMI and milk yields (MY) was measured to 28 DIM. Data were analyzed using Proc MIXED (SAS 9.4) for fixed effects of Trt, Time, and Trt×Time with breed as covariate and time as repeated measure. No health events were observed related to parturition.

Prepartum DMI among treatments did not differ (P=0.66). Cows fed D3 and Hy-D® had greater (P=0.02) prepartum serum Ca than CON and greater urinary Ca excretions (P=0.02). Average postpartum serum Ca (mg/dL) tended (P=0.06) to be greater in D3 (8.8) and Hy-D® (8.4) cows than CON (7.8). Postpartum DMI was affected by trt (P<0.02), with CON consuming more than D3 and Hy-D® not differing from either trt. Daily MY (kg/d) was greatest (P<0.01) for Hy-D® (37.4) compared to D3 (34.2) and CON (30.1). These results suggest a fully acidogenic diet prepartum with vitamin D was effective in maintaining peripartum serum calcium and Hy-D® improved MY in early lactation.

Conclusion

A fully acidogenic diet prepartum with vitamin D was effective in maintaining peripartum serum calcium and the combination of Animate® and Hy-D® improved milk yield in early lactation, with Animate® being the sole anion source.

Example 4

Transition Cow Calcium Homeostasis and Vitamin D Status

Experimental Design

Animals and Treatments

Sixty early dry first-parous and multiparous Holstein cows are trained to the Bio-Control feeding system and randomly assigned to one of three negative DCAD prefresh dry cow treatment diets (5 first-parous, and 15 miltiparous cows/treatment) blocked for parity, age at first calving, previous ME305 milk, SCC, BW and predicted calving date. Cows begin treatment diets between 24 to 28 days prior to expected calving date and remain on treatment to calving. After calving, cows are move into lactation pens and fed the same lactation diet, and followed through 30 DIM.

Treatments consist of:
  1. Control diet: Negative DCAD diet containing 40,000 IU vitamin D3/cow/d from Cholecalciferol
  2. Control diet+40,000 IU vitamin D/cow/d from 25-OH Vitamin D3 from Rovimix
  3. Control diet+80,000 IU vitamin D/cow/d from 25-OH Vitamin D3 from Rovimix Rations, Feeding and Cow Movement Dry period (Bio-Controlpens): The treatment diets are formulated to the same level of negative DCAD with Animate (sole source of anions), and dietary calcium (≥180 grams/cow/d).

Treatment diets differ only on the amount of vitamin D supplied daily. While on the DCAD diet urine pH values are maintained from 5.5 and 6.0. Urine pH values above 6.0 are adjusted by feeding additional Animate until urine pH falls within the acceptable range. All DCAD diets conform to specified pre-fresh cow negative DCAD diet recommendations. Each treatment diet is fed to a 10% feed refusal rate and individual DMI and orts recorded daily.

Lactation (group pens): After calving all cows switch to a common lactation diet containing 40,000 IU/d of vitamin D. The lactation ration is fed to a 10% feed refusal rate and pen DMI and orts recorded daily.

Cow movement: Training of early dry cows to the Bio-Control system starts prior to negative DCAD diet assignment. Prior to calving (visual indications) cows move to a maternity pen to calve. After calving cows are switched to a lactation ration. Cows move from maternity to lactation group pens and remain on the study until 30 DIM. During each phase of the study, dry and lactation, there are approximately an equal number of cows represented from each negative DCAD diet.

Measurements

Sample Collection:
  1. Urine pH (pre-fresh dry cows):
    a. Urine collection for creatinine, Ca, P, and Mg commences when Animate close up diets are fed (day 0, prior to start) and then on days (relative to calving) −21, −14, −7, −5, −3, −1, 0, +0.5 (12-24 hours), +1 (24-36 hours), +3 (36-48 hours), +4 (48-72 hours), +7 and +14.
    b. Urine pH is determined on urine collected 4 to 6 hours post-feeding (DCAD diets only) from samples collected on three consecutive days per week. The target pH range is 5.5 to 6.0.
  2 Blood Prepartum:
    a. Serum and whole blood samples collection for ionized calcium, total Ca, P, and Mg commences when negative DCAD diets are fed and then on days (relative to calving) −21, −14, −7, −5, −3, −1, 0, +0.5 (12-24 hours), +1 (24-36 hours), +3 (36-48 hours), +4 (48-72 hours), +7 and +14.

FIGS. 2 and 3 provide tables with the sample collection schedule and illustrating which variables are measured at each time point.

Production:
  1. Absolute milk, ECM (daily, weekly avg.)
  2. Milk components (composite from 3× milk/day): BF, MP, lactose, SNF, lactose (1×/week @ DIM 7, 14, 28)
  3. Somatic cell count (1×/week, from 3× milk/day)
  4. Dry matter intake/orts (individual prepartum daily/weekly, avg. pen post-partum 3-day avg)

5. Body weight: dry off (covariate), treatment assignment (day 0), days relative to calving −14, −7, +3, +14, and +28.
6. Body condition score: dry-off, treatment assignment (day 0), −14, −7, +3, +14, and +28

Behavior and Health:
1. Rumination (Cow Manager)
2. Activity (Cow Manager)
3. Feeding bouts: per day, weekly (Bio-Control System)
4. Hi/Lo temperature, THI calculation (daily, weekly avg)
5. Monitor and record health disorders (ketosis, DA, retained placenta, metritis, mastitis, milk fever, etc.)

Cow Exclusion Criteria and Replacement:
The following require removing a cow from the study and replacing with another cow.
1. Cows that calve twins
2. Cows that calve 15 days earlier than expected calving date. Cows must spend a minimum of 21 days on experimental diets before calving.
3. Cows that are injured, or become injured, or develop a health condition unrelated to nutritional causes (severe laminitis, etc.).
4. Cows that become chronically ill with periparturient health problems.
5. Cows that do not reach 28 DIM.

Figure 4:
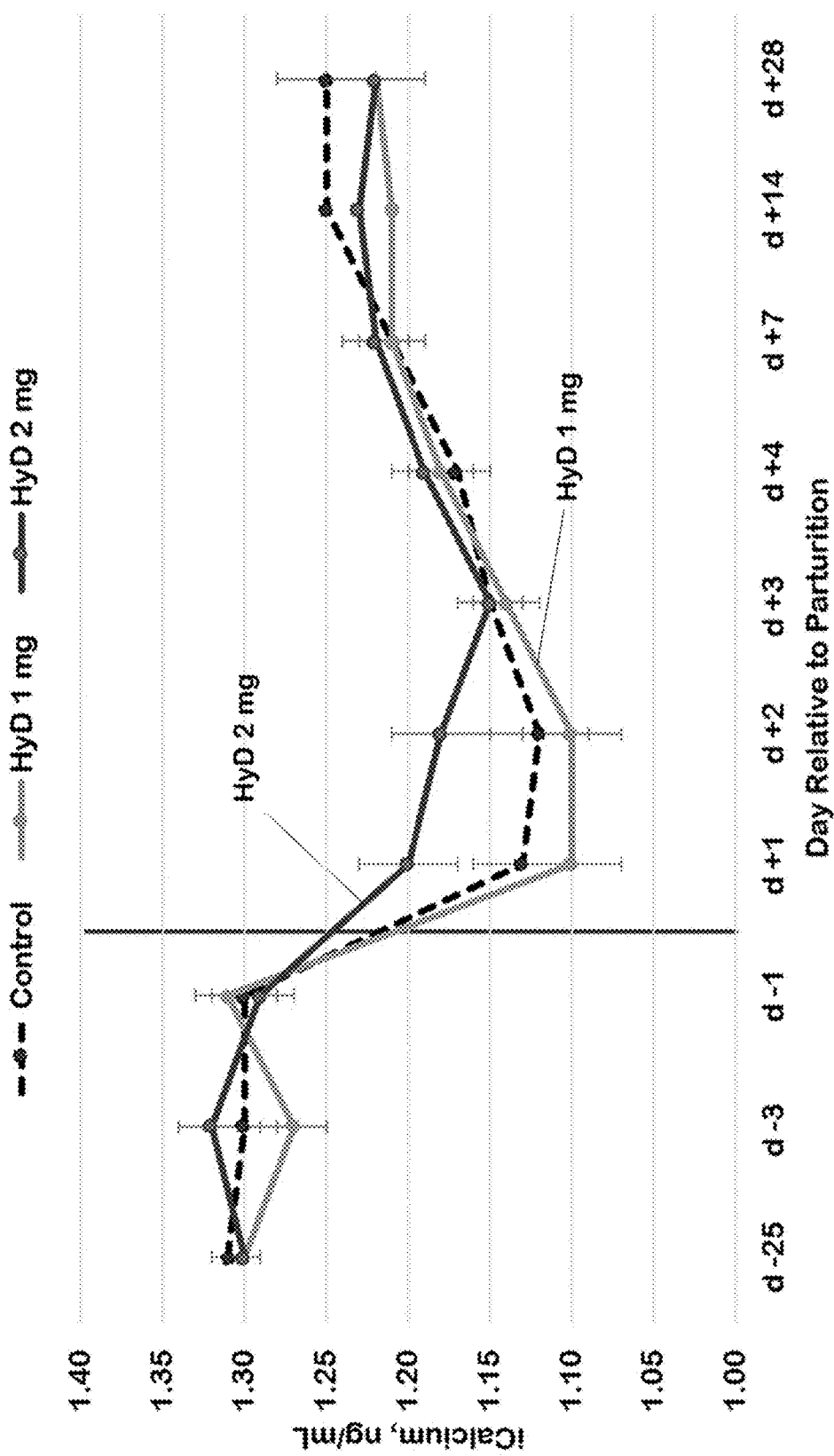
FIG. 4 is a graph of ionized calcium versus day relative to parturition, illustrating the levels of ionized calcium in whole blood at various days pre- and post-partum.
Figure 6:
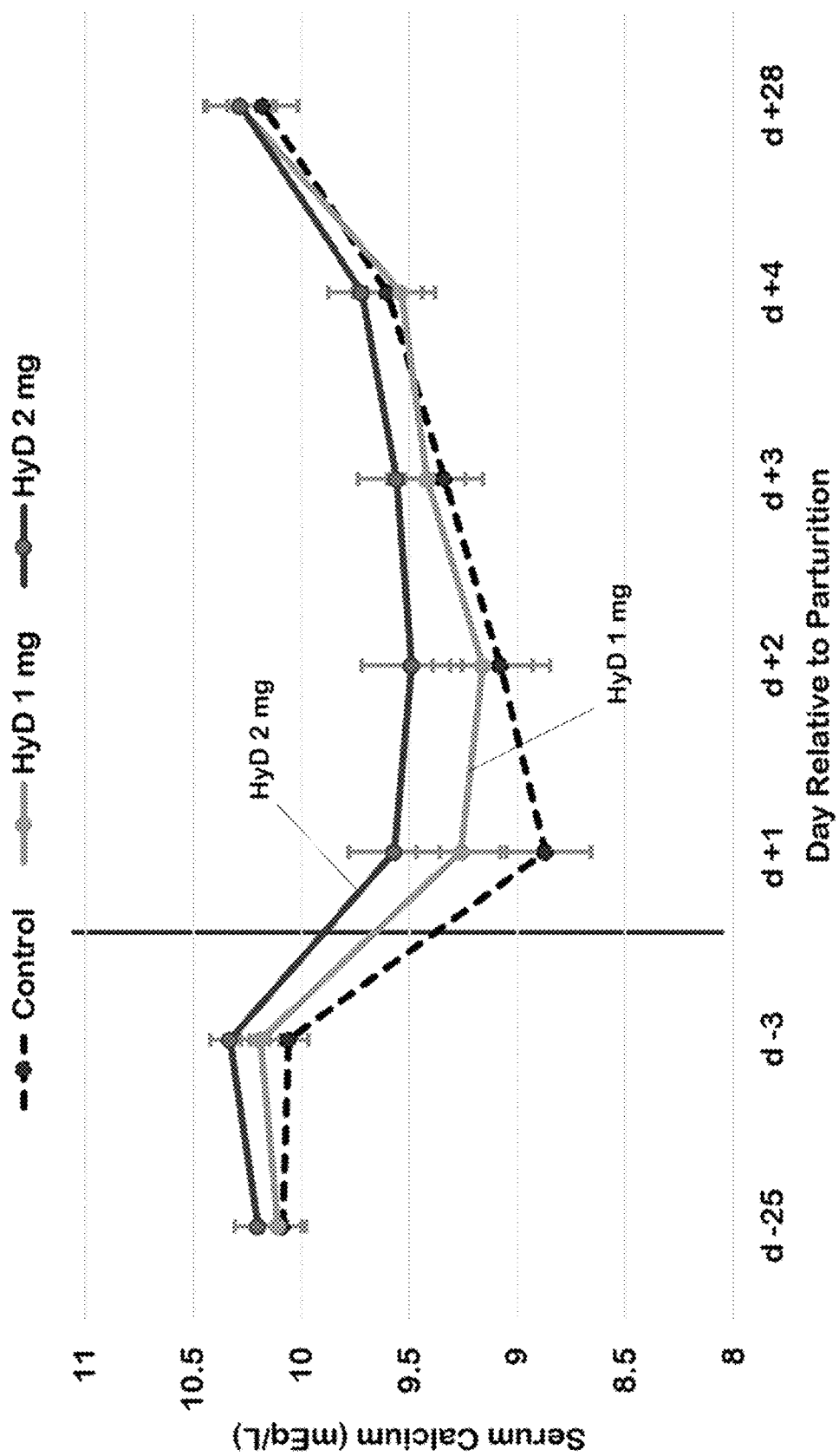
FIG. 6 is a graph of total calcium versus day relative to parturition, illustrating the levels of total calcium in serum at various days pre- and post-partum.

Certain results from the trial are provided in FIGS. 4-7. The data demonstrates at least a significant difference in calcium levels at day one of lactation, denoted as +1 in the figures.

VIII. Exemplary Embodiments

The following numbered paragraphs illustrate exemplary embodiments of the disclosed technology.

Paragraph 1. A composition comprising:
magnesium chloride, magnesium sulfate, ammonium chloride, ammonium sulfate, and calcium sulfate, and/or complexes thereof, and
a 25-hydroxy vitamin D species.

Paragraph 2. The composition of paragraph 1, wherein the composition further comprises magnesium oxide, phosphoric acid, molasses or silica, dried distillers grains and solubles (DDGS), corn gluten feed, mineral clay, water, or a combination thereof.

Paragraph 3. The composition of paragraph 1 or paragraph 2, wherein the composition comprises one or more of magnesium oxide, phosphoric acid, molasses or silica.

Paragraph 4. The composition of any one of paragraphs 1-3, wherein the composition comprises one or more of dried distillers grains and solubles (DDGS), corn gluten feed, mineral clay, or water.

Paragraph 5. The composition of any one of paragraphs 1-4, wherein the composition comprises from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, and/or complexes thereof.

Paragraph 6. The composition of any one of paragraphs 1-5, wherein the composition comprises from greater than zero to 1% w/w phosphoric acid.

Paragraph 7. The composition of any one of paragraphs 1-6, wherein the composition comprises from greater than zero to 5% w/w molasses, from greater than zero to 1% w/w silica, from greater than zero to 10% water, or a combination thereof.

Paragraph 8. The composition of any one of paragraphs 1-7, wherein the composition comprises from 20% to 60% or more of w/w dried distillers grains and solubles (DDGS), corn gluten feed, mineral clay, or a combination thereof.

Paragraph 9. The composition of any one of paragraphs 1-8, wherein the composition comprises magnesium chloride, magnesium sulfate, ammonium chloride, ammonium sulfate, and calcium sulfate, or complexes thereof, and further comprises phosphoric acid, silica, molasses, DDGS, and water.

Paragraph 10. The composition of paragraph 9, wherein the composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 1% w/w silica, from greater than zero to 5% w/w molasses, from 30% to 60% w/w DDGS, and from greater than zero to 10% water.

Paragraph 11. The composition of any one of paragraphs 1-8, wherein the composition comprises magnesium chloride, magnesium sulfate, ammonium chloride, ammonium sulfate, and calcium sulfate, or complexes thereof, and further comprises phosphoric acid, magnesium oxide, mineral clay, and water.

Paragraph 12. The composition of paragraph 11, wherein the composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from 1% to 5% w/w magnesium oxide, from 20% to 40% w/w mineral clay, and from greater than zero to 10% water.

Paragraph 13. The composition of any one of paragraphs 1-8, wherein the composition comprises magnesium chloride, magnesium sulfate, ammonium chloride, ammonium sulfate, and calcium sulfate, or complexes thereof, and further comprises phosphoric acid, molasses, corn gluten feed, and water.

Paragraph 14. The composition of paragraph 13, wherein the composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 5% w/w molasses, from 30% to 60% w/w corn gluten feed, and from greater than zero to 10% water.

Paragraph 15. The composition of any one of paragraphs 1-14, wherein the composition comprises:
a first composition comprising magnesium chloride, magnesium sulfate, ammonium chloride, ammonium sulfate, and calcium sulfate, and/or complexes thereof and optionally one or more of magnesium oxide, phosphoric acid, molasses or silica, dried distillers grains and solubles (DDGS), corn gluten feed, mineral clay, or water; and
a second composition comprising the 25 hydroxy vitamin D species.

Paragraph 16. The composition of paragraph 15, wherein the composition is an admixture of the first and second compositions.

Paragraph 17. The composition of paragraph 15, wherein the first and second compositions are formulated together to form single particles, where each particle comprises both the first and second compositions.

Paragraph 18. The composition of paragraph 17, wherein the composition comprises particles of the first composition that are at least partially coated with the second composition.

Paragraph 19. The composition of paragraph 18, wherein the composition further comprises a carrier that facilitates the second composition at least partially coating the particles of the first composition.

Paragraph 20. The composition of paragraph 19, wherein the carrier is a mineral oil.

Paragraph 21. The composition of any one of paragraphs 1-20, wherein the composition further comprises a calcium source.

Paragraph 22. The composition of paragraph 21, wherein the calcium source is calcium carbonate, bone ash, bone meal, calcite, limestone, calcium gluconate, calcium hydroxide, calcium sulfate, calcium chloride, calcium butyrate, chalk, clam shells, oyster shells, dolemite, calcium chelates, monocalcium phosphate, dicalcium phosphate, calcium propionate, or any combination thereof.

Paragraph 23. The composition of any one of paragraphs 1-22, wherein the composition comprises from 20,000 IU to 200,000 IU of the 25-hydroxy vitamin D species.

Paragraph 24. The composition of paragraph 23, wherein the composition comprises from 50,000 IU to 120,000 IU of the 25-hydroxy vitamin D species.

Paragraph 25. The composition of any one of paragraphs 1-24, further comprising a feed.

Paragraph 26. The composition of any one of paragraphs 1-25, further comprising one or more of yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride III, or combinations thereof.

Paragraph 27. The composition of paragraph 26, wherein the composition further comprises silica, mineral clay, glucan, mannans, and an endoglucanohydrolase.

Paragraph 28. The composition of paragraph 26 or paragraph 27, wherein the composition further comprises a direct fed microbial.

Paragraph 29. The composition of paragraph 28, wherein the direct fed microbial is *Bacillus coagulans, Bacillus subtilis, Bacillus licheniformis, Bacillus amyloliquefaciens*, or a combination thereof.

Paragraph 30. The composition of any one of paragraphs 26-29, wherein the composition further comprises yucca and quillaja.

Paragraph 31. The composition of any one of paragraphs 26-30, wherein the composition further comprises a chromium compound, a metal chelate, a copper species, or a combination thereof.

Paragraph 32. The composition of any one of paragraphs 1-31, wherein the 25-hydroxy vitamin D species is 25-hydroxy vitamin $D_3$.

Paragraph 33. A method, comprising administering to a ruminant a combination and/or composition comprising:
magnesium chloride, magnesium sulfate, ammonium chloride, ammonium sulfate, and calcium sulfate, and/or complexes thereof, and
a 25-hydroxy vitamin D species.

Paragraph 34. The method of paragraph 33, wherein the combination and/or composition further comprises magnesium oxide, phosphoric acid, molasses or silica, dried distillers grains and solubles (DDGS), corn gluten feed, mineral clay, water, or a combination thereof.

Paragraph 35. The method of paragraph 33 or paragraph 34, wherein the combination and/or composition comprises:
a first composition comprising magnesium chloride, magnesium sulfate, ammonium chloride, ammonium sulfate, and calcium sulfate, and/or complexes thereof, and
a second composition comprising the 25-hydroxy vitamin D species.

Paragraph 36. The method of paragraph 35, wherein the first composition comprises from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, and/or complexes thereof.

Paragraph 37. The method of paragraph 35 or paragraph 36, wherein the first composition comprises from greater than zero to 1% w/w phosphoric acid.

Paragraph 38. The method of any one of paragraphs 35-37, wherein the first composition comprises from greater than zero to 5% w/w molasses, from greater than zero to 1% w/w silica, from greater than zero to 10% water, or a combination thereof.

Paragraph 39. The method of any one of paragraphs 35-38, wherein the first composition comprises from 20% to 60% or more w/w of dried distillers grains and solubles (DDGS), corn gluten feed, mineral clay, or a combination thereof.

Paragraph 40. The method of any one of paragraphs 35-39, wherein the first composition comprises magnesium chloride, magnesium sulfate, ammonium chloride, ammonium sulfate, and calcium sulfate, or complexes thereof, and further comprises phosphoric acid, silica, molasses, DDGS, and water.

Paragraph 41. The method of paragraph 40, wherein the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 1% w/w silica, from greater than zero to 5% w/w molasses, from 30% to 60% w/w DDGS, and from greater than zero to 10% water.

Paragraph 42. The method of any one of paragraphs 35-39, wherein the first composition comprises magnesium chloride, magnesium sulfate, ammonium chloride, ammonium sulfate, and calcium sulfate, or complexes thereof, and further comprises phosphoric acid, magnesium oxide, mineral clay, and water.

Paragraph 43. The method of paragraph 42, wherein the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from 1% to 5% w/w magnesium oxide, from 20% to 40% w/w mineral clay, and from greater than zero to 10% water.

Paragraph 44. The method of any one of paragraphs 35-39, wherein the first composition comprises magnesium chloride, magnesium sulfate, ammonium chloride, ammonium sulfate, and calcium sulfate, or complexes thereof, and further comprises phosphoric acid, molasses, corn gluten feed, and water.

Paragraph 45. The composition of paragraph 44, wherein the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 5% w/w molasses, from 30% to 60% w/w corn gluten feed, and from greater than zero to 10% water.

Paragraph 46. The method of any one of paragraphs 33-45, wherein the combination and/or composition comprises from 20,000 IU to 200,000 IU of the 25-hydroxy vitamin D species.

Paragraph 47. The method of paragraph 46, wherein the combination and/or composition comprises from 50,000 IU to 120,000 IU of the 25-hydroxy vitamin D species.

Paragraph 48. The method of any one of paragraphs 33-47, wherein the combination and/or composition is admixed with a calcium source.

Paragraph 49. The method of paragraph 48, wherein the admixture comprises at least 1.6% dietary calcium.

Paragraph 50. The method of any one of paragraphs 33-49 wherein the combination and/or composition comprises particles of the first composition at least partially coated with the second composition.

Paragraph 51. The method of paragraph 50, wherein the combination and/or composition further comprises a carrier.

Paragraph 52. The method of paragraph 51, wherein the carrier is a mineral oil.

Paragraph 53. The method of paragraph 50, wherein the second composition is an emulsion.

Paragraph 54. The method of any one of paragraphs 33-53, wherein the combination and/or composition is admixed with a feed.

Paragraph 55. The method of any one of paragraphs 33-54, wherein the combination and/or composition further comprises yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride III, or combinations thereof.

Paragraph 56. The method of any one of paragraphs 33-55, wherein the method further comprises administering silica, mineral clay, glucan, mannans, and an endoglucanohydrolase.

Paragraph 57. The method of any one of paragraphs 33-56, wherein the method further comprises administering a direct fed microbial.

Paragraph 58. The method of paragraph 57, wherein the direct fed microbial is *Bacillus coagulans, Bacillus subtilis, Bacillus licheniformis, Bacillus amyloliquefaciens*, or a combination thereof.

Paragraph 59. The method of any one of paragraphs 33-58, wherein the method further comprises administering yucca and quillaja.

Paragraph 60. The method of any one of paragraphs 33-59, wherein the method further comprises administering a chromium compound, a metal chelate, a copper species, or a combination thereof.

Paragraph 61. The method of any one of paragraphs 33-60, wherein the 25-hydroxy vitamin D species is 25-hydroxy vitamin $D_3$.

Paragraph 62. The method of any one of paragraphs 33-61, wherein the ruminant is a bovine, sheep, goat, deer, elk, alpaca, camel or llama.

Paragraph 63. The method of paragraph 62, wherein the bovine is a cow, bull, steer, heifer, calf, bison, or buffalo.

Paragraph 64. The method of paragraph 63, wherein the cow is a dairy cow.

Paragraph 65. The method of paragraph 64, wherein the combination and/or composition is administered to the dairy cow for a time period of from the start of the dry period to up to 150 days post calving.

Paragraph 66. The method of paragraph 64, wherein the combination and/or composition is administered to the dairy cow for a time period of from 65 days prior to calving to up to 150 days or more post calving.

Paragraph 67. The method of paragraph 65 or paragraph 66, wherein the time period is from 56 days prior to calving.

Paragraph 68. The method of any one of paragraphs 65-67 wherein the time period is from 28 days prior to calving.

Paragraph 69. The method of any one of paragraphs 65-68, wherein the time period is from 21 days prior to calving.

Paragraph 70. The method of any one of paragraphs 65-69, wherein the time period is up to 100 days post calving.

Paragraph 71. The method of any one of paragraphs 65-70, wherein the time period is up to 75 days post calving.

Paragraph 72. The method of any one of paragraphs 65-71, wherein the time period is up to 48 days post calving.

Paragraph 73. The method of any one of paragraphs 65-72, wherein the time period is up to 28 days post calving.

Paragraph 74. The method of any one of paragraphs 33-73, wherein the combination and/or composition is administered in an amount sufficient to provide from 0.5 pounds per day to 2 pounds per day of the first composition.

Paragraph 75. The method of paragraph 74, wherein the combination and/or composition is administered in an amount sufficient to provide from 1.2 pounds per day to 1.5 pounds per day of the first composition.

Paragraph 76. The method of any one of paragraphs 33-75, wherein the combination and/or composition is administered in an amount sufficient to provide from 20,000 IU to 240,000 IU of the 25-hydroxy vitamin D species.

Paragraph 77. The method of paragraph 76, wherein the combination and/or composition is administered in an amount sufficient to provide from 50,000 IU to 120,000 IU of the 25-hydroxy vitamin D species.

Paragraph 78. The method of any one of paragraphs 33-77, wherein the combination and/or composition is administered in an amount sufficient to provide from 0.5 mg per head per day to 5 mgs per head per day of the 25-hydroxy vitamin D species.

Paragraph 79. The method of paragraph 78, wherein the combination and/or composition is administered in an amount sufficient to provide from 1 mg per head per day to 3 mgs per head per day of the 25-hydroxy vitamin D species.

Paragraph 80. The method of any one of paragraphs 33-79, wherein the first composition and the second composition are administered substantially sequentially.

Paragraph 81. The method of any one of paragraphs 33-79, wherein the first composition and the second composition are administered sequentially in any order.

Paragraph 82. The method of paragraph 81, wherein administering sequentially comprises a first administration comprising administering one of the first and second compositions, and a second administration subsequent to the first administration, the second administration comprising administering the other of the first and second compositions, such that a time period between the first and second administrations is sufficient for the animal to receive an overlapping benefit from the first and second administrations.

Paragraph 83. A method of increasing milk yield in a dairy cow, the method comprising administering to the dairy cow a combination and/or composition comprising 25-hydroxy vitamin $D_3$ and magnesium chloride, magnesium sulfate, ammonium chloride, ammonium sulfate, and calcium sulfate, and/or complexes thereof.

Paragraph 84. The method of paragraph 83, wherein the combination and/or composition further comprises magnesium oxide, phosphoric acid, molasses or silica, dried distillers grains and solubles (DDGS), corn gluten feed, mineral clay, water, or a combination thereof.

Paragraph 85. The method of paragraph 83 or paragraph 84, wherein the combination and/or composition comprises from greater than zero to 30% or more w/w magnesium chloride, from 10% or less to 35% or more w/w magnesium sulfate, from 10% to 30% or more w/w ammonium chloride, from 10% to 40% or more w/w ammonium sulfate, and from 3% to 15% or more w/w calcium sulfate, and/or complexes thereof.

Paragraph 86. The method of any one of paragraphs 83-85, wherein the combination and/or composition comprises magnesium chloride, magnesium sulfate, ammonium chloride, ammonium sulfate, and calcium sulfate, or complexes thereof, and further comprises phosphoric acid, silica, molasses, DDGS, and water.

Paragraph 87. The method of any one of paragraphs 83-85, wherein the combination and/or composition comprises magnesium chloride, magnesium sulfate, ammonium chloride, ammonium sulfate, and calcium sulfate, or complexes thereof, and further comprises phosphoric acid, magnesium oxide, mineral clay, and water.

Paragraph 88. The method of any one of paragraphs 83-85, wherein the combination and/or composition comprises magnesium chloride, magnesium sulfate, ammonium chloride, ammonium sulfate, and calcium sulfate, or complexes thereof, and further comprises phosphoric acid, molasses, corn gluten feed, and water.

Paragraph 89. The method of any one of paragraphs 83-88, wherein the combination and/or composition is administered during the dairy cow's transition period.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition, comprising:
    a 25-hydroxy vitamin D species; and
    from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprising from greater than zero to 1% w/w phosphoric acid, from greater than zero to 1% w/w silica, from greater than zero to 5% w/w molasses, from 30% to 60% w/w dried distillers grains and solubles (DDGS), and from greater than zero to 10% water;
    from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprising from greater than zero to 1% w/w phosphoric acid, from 1% to 5% w/w magnesium oxide, from 20% to 40% w/w mineral clay, and from greater than zero to 10% water; or
    from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprising from greater than zero to 1% w/w phosphoric acid, from greater than zero to 5% w/w molasses, from 30% to 60% w/w corn gluten feed, and from greater than zero to 10% water.

2. The composition of claim 1, wherein the composition is an admixture of a first composition and a second composition, and wherein:
    the first composition comprises the magnesium chloride, the magnesium sulfate, the ammonium chloride, the ammonium sulfate, and the calcium sulfate, and/or complexes thereof, and the phosphoric acid, and the water, and either
    the silica, the molasses and the DDGS, or
    the magnesium oxide, and the mineral clay, or
    the molasses and the corn gluten feed; and
    the second composition comprises the 25 hydroxy vitamin D species.

3. The composition of claim 1, wherein the composition is formulated as particles where each particle comprises all components of the composition.

4. The composition of claim 3, wherein the particles comprise a core of a first composition that is at least partially coated with a second composition, and wherein
    the first composition comprises the magnesium chloride, the magnesium sulfate, the ammonium chloride, the ammonium sulfate, and the calcium sulfate, and/or complexes thereof, and the phosphoric acid, and the water, and either
    the silica, the molasses and the DDGS, or
    the magnesium oxide, and the mineral clay, or
    the molasses and the corn gluten feed; and
    the second composition comprises the 25 hydroxy vitamin D species.

5. The composition of claim 1, wherein the composition comprises from 20,000 IU to 200,000 IU of the 25-hydroxy vitamin D species.

6. The composition of claim 1, further comprising one or more of a calcium source, a feed, yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride III, or combinations thereof.

7. The composition of claim 1, wherein the 25-hydroxy vitamin D species is 25-hydroxy vitamin $D_3$.

8. A method, comprising administering the composition of claim 1 to a ruminant.

9. A method comprising administering to a ruminant a combination of a first composition and a second composition, wherein:
    the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 1% w/w silica, from greater than zero to 5% w/w molasses, from 30% to 60% w/w dried distillers grains and solubles (DDGS), and from greater than zero to 10% water; or the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from 1% to 5% w/w magnesium oxide, from 20% to 40% w/w mineral clay, and from greater than zero to 10% water; or the first composition comprises from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, and further comprises from greater than zero to 1% w/w phosphoric acid, from greater than zero to 5% w/w molasses, from 30% to 60% w/w corn gluten feed, and from greater than zero to 10% water; and the second composition comprises a 25-hydroxy vitamin D species.

10. The method of claim 8, wherein the composition comprises from 20,000 IU to 200,000 IU of the 25-hydroxy vitamin D species.

11. The method of claim 8, wherein the composition further comprises yucca, Quillaja, direct fed microbial, chromium compound, silica, mineral clay, glucan, mannans, endoglucanohydrolase, metal chelate, polyphenol, copper species, vitamin, allicin, alliin, alliinase, yeast, growth promotant, preservative, antimicrobial, a growth factor, a vaccine, difructose anhydride III, a feed, a calcium source, or combinations thereof.

12. The method of claim 11, wherein the calcium source is calcium carbonate, bone ash, bone meal, calcite, limestone, calcium gluconate, calcium hydroxide, calcium sulfate, calcium chloride, calcium butyrate, chalk, clam shells, oyster shells, dolemite, calcium chelates, monocalcium phosphate, dicalcium phosphate, calcium propionate, or any combination thereof.

13. The method of claim 11, wherein the composition comprises at least 1.6% dietary calcium.

14. The method of claim 8, wherein the ruminant is a bovine, sheep, goat, deer, elk, alpaca, camel or llama.

15. The method of claim 8, wherein the composition is administered to a dairy cow for a time period of:
from the start of the dry period to up to 150 days post calving; or
from 65 days prior to calving to up to 150 days or more post calving.

16. The method of claim 9, wherein
the combination is administered in an amount sufficient to provide from 0.5 pounds per day to 2 pounds per day of the first composition;
the combination is administered in an amount sufficient to provide from 20,000 IU to 240,000 IU of the 25-hydroxy vitamin D species;
or a combination thereof.

17. The method of claim 9, wherein the first composition and the second composition are administered sequentially in any order.

18. A method of increasing milk yield in a dairy cow, the method comprising administering to the dairy cow a combination and/or composition comprising 25-hydroxy vitamin $D_3$ and from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 1% w/w silica, from greater than zero to 5% w/w molasses, from 30% to 60% w/w DDGS, and from greater than zero to 10% water; or from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from 1% to 5% w/w magnesium oxide, from 20% to 40% w/w mineral clay, and from greater than zero to 10% water; or from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 5% w/w molasses, from 30% to 60% w/w corn gluten feed, and from greater than zero to 10% water.

19. The method of claim 8, wherein the ruminant is a dairy cow.

20. The composition of claim 1, wherein the composition comprises the 25-hydroxy vitamin D species; and
from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 1% w/w silica, from greater than zero to 5% w/w molasses, from 30% to 60% w/w dried distillers grains and solubles (DDGS), and from greater than zero to 10% water.

21. The composition of claim 1, wherein the composition comprises the 25-hydroxy vitamin D species; and
from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from 1% to 5% w/w magnesium oxide, from 20% to 40% w/w mineral clay, and from greater than zero to 10% water.

22. The composition of claim 1, wherein the composition comprises the 25-hydroxy vitamin D species; and
from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 5% w/w molasses, from 30% to 60% w/w corn gluten feed, and from greater than zero to 10% water.

23. The method of claim 18, the method comprising administering to the dairy cow a combination and/or composition comprising the 25-hydroxy vitamin D3 and
from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 1% w/w silica, from greater than zero to 5% w/w molasses, from 30% to 60% w/w DDGS, and from greater than zero to 10% water.

24. The method of claim 18, the method comprising administering to the dairy cow a combination and/or composition comprising the 25-hydroxy vitamin D3 and from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from 1% to 5% w/w magnesium oxide, from 20% to 40% w/w mineral clay, and from greater than zero to 10% water.

25. The method of claim 18, the method comprising administering to the dairy cow a combination and/or composition comprising the 25-hydroxy vitamin D3 and from greater than zero to 30% w/w magnesium chloride, from 10% or less to 35% w/w magnesium sulfate, from 10% to 30% w/w ammonium chloride, from 10% to 40% w/w ammonium sulfate, from 3% to 15% w/w calcium sulfate, or complexes thereof, from greater than zero to 1% w/w phosphoric acid, from greater than zero to 5% w/w molasses, from 30% to 60% w/w corn gluten feed, and from greater than zero to 10% water.

* * * * *